US012721884B2

(12) United States Patent
Schneider et al.

(10) Patent No.: US 12,721,884 B2
(45) **Date of Patent: *Sep. 1, 2026**

(54) PRODUCTION OF MHC II/CII COMPLEXES

(71) Applicant: FRAUNHOFER-GESELLSCHAFT ZUR FORDERUNG DER ANGEWANDTEN FORSCHUNG E.V., Munich (DE)

(72) Inventors: Nadine Schneider, Frankfurt am Main (DE); Bingze Xu, Uppsala (SE); Sylvia Cienciala, Nidderau (DE); Rikard Holmdahl, Stockholm (SE); Harald Burkhardt, Frankfurt am Main (DE)

( * ) Notice: Subject to any disclaimer, the term of this patent is extended or adjusted under 35 U.S.C. 154(b) by 1214 days.

This patent is subject to a terminal disclaimer.

(21) Appl. No.: 17/633,916

(22) PCT Filed: Aug. 7, 2020

(86) PCT No.: PCT/EP2020/072287

§ 371 (c)(1),
(2) Date: Feb. 8, 2022

(87) PCT Pub. No.: WO2021/028350

PCT Pub. Date: Feb. 18, 2021

(65) Prior Publication Data

US 2022/0288177 A1 Sep. 15, 2022

(30) Foreign Application Priority Data

Aug. 9, 2019 (EP) .................................... 19191094

(51) Int. Cl.

| | |
|---|---|
| ***A61K 39/00*** | (2006.01) |
| ***A61K 39/385*** | (2006.01) |
| ***A61P 19/02*** | (2006.01) |
| ***A61P 37/02*** | (2006.01) |
| ***C12N 5/071*** | (2010.01) |

(52) U.S. Cl.

CPC ........ *A61K 39/0008* (2013.01); *A61K 39/385* (2013.01); *A61P 19/02* (2018.01); *A61P 37/02* (2018.01); *C12N 5/0687* (2013.01); *A61K 2039/577* (2013.01); *A61K 2039/605* (2013.01); *A61K 2039/622* (2013.01); *C12N 2510/02* (2013.01)

(58) Field of Classification Search

None

See application file for complete search history.

(56) References Cited

U.S. PATENT DOCUMENTS

| | | | |
|---|---|---|---|
| 6,106,840 | A | 8/2000 | Clark |
| 6,451,314 | B1 | 9/2002 | Clark |
| 6,632,604 | B2 | 10/2003 | Mach |
| 2007/0161545 | A1 | 7/2007 | Holmdahl |
| 2009/0227516 | A1 | 9/2009 | Holmdahl et al. |
| 2010/0015644 | A1 | 1/2010 | Gerarda Havenith |
| 2010/0168390 | A1 | 7/2010 | Brix et al. |
| 2010/0226854 | A1* | 9/2010 | Scholler ........... G01N 33/56977 530/391.1 |
| 2013/0309229 | A1 | 11/2013 | Yang et al. |

FOREIGN PATENT DOCUMENTS

| | | | |
|---|---|---|---|
| EP | 1332760 | A1 | 8/2003 |
| WO | 08151396 | A | 6/1996 |
| WO | 1996040944 | A2 | 12/1996 |
| WO | 1998005684 | A2 | 2/1998 |
| WO | 2001036448 | A2 | 5/2001 |
| WO | 2003/050542 | A2 | 6/2003 |
| WO | 2007/017556 | A1 | 2/2007 |
| WO | 2007/058587 | A1 | 5/2007 |
| WO | 2007/123976 | A2 | 11/2007 |
| WO | 2008/090360 | A1 | 7/2008 |
| WO | 2012/138294 | A1 | 10/2012 |

OTHER PUBLICATIONS

Kjelle'n et al., Eur. J. Imunol28: 756-767 (Year: 1998).*
Holm et al., ChemBiochem 3: 1209-1222 (Year: 2002).*
Jones et al., Nat Rev. Immunol. 6: 271-282 (Year: 2006).*
Nikolich-Zugich et al., Nature Reviews/Immunology 4: 123-132 (Year: 2004).*
Du Souich et al., "Immunomodulatory and anti-inflammatory effects of chondroitin sulphate," J. Cell. Mol. Med. Vol 13, No. 8A, 2009 pp. 1451-1463, doi:10.1111/j.1582-4934.2009.00826.x.
Malmstrom et al., "T cells that are naturally tolerant to cartilage-derived type II collagen are involved in the : evelopment of collagen-induced arthritis." Arthritis Research. 2000. 2, 315-326.
Michaelsson et al., "Antigen processing and presentation of a naturally glycosylated protein elicits major histocompatibility complex class II-restricted, carbohydrate-specific T cells." European Journal of Immunology_ 1996. 26(8):1906-1910.
Michaelsson et al., "Identification of an immunodominant type-II collagen peptide recognized by T cells in H-2q mice: , self tolerance at the level of determinant selection." European Journal of Immunology_ 1992. 22(7): 1819-1825.
Michaelsson et al., "T cell recognition of carbohydrates on type II collagen." Journal of Experimental Medicine. 1994. 180(2), 745-749.

(Continued)

*Primary Examiner* — Phuong Huynh
(74) *Attorney, Agent, or Firm* — SAFFIRE IP; Daren P Nicholson

(57) ABSTRACT

The present invention relates to in situ glycosylated MHC II/CII peptide complexes, i.e., complexes naturally glycosylated during recombinant protein expression in the host cell. The invention further relates to methods of producing glycosylated MHC II/CII peptide complexes in mammalian cells. Furthermore the invention relates to the use of such post-translationally modified, preferably glycosylated MHC/CII complexed for use in treating rheumatoid arthritis, preferably in humans.

18 Claims, 16 Drawing Sheets

Specification includes a Sequence Listing.

(56) References Cited

OTHER PUBLICATIONS

Myers et al., "Characterization of a tolerogenic T cell epitope of type II collagen and its relevance to collagen-induced arthritis." Journal of Immunology_ 1992. 149: 1439-1443.
Zuo et al., "A single-chain class II MHC-IgG3 fusion protein inhibits autoimmune arthritis by induction of antigen-specific hyporesponsiveness." Journal of Immunology_2002. 168(5):2554-2559.
Broddefalk et al., "Preparation of a diglycosylated hydroxylysine building block used in solid-phase synthesis of a Glycopeptidefrom type II collagen." Journal of Organic Chemistry. 1999. 64, 8948-8953.
Myers,"Peptide-Induced Suppression of Collagen-Induced Arthritis in HLA-DR1 Transgenic Mice," American College of Rheumatology,vol. 46, No. 12, Dec. 2002, pp. 3369-3377.
Ward, Eliot, "Novel fusion protein-expressing lentiviral vectors ameliorate collagen induced arthritis," https://discovery.ucl.ac.uk/id/eprint/20480/, Dec. 31, 2010.
Gregersen PK et al., "The Shared Epitope Hypthesis: An approach to understanding the molecular genetics of susceptibility to rheumatoid arthritis," Arthritis Rheum. 1987;30:1205-1213.
Burkhardt H et al., "Humoral immune response to citrullinated collagen type II determinants in early rheumatoid arthritis," Eur J Immunol. 2005; 35:1643-52.
Backlund et al. "Predominant selection of T cells specific for the glycosylated collagen type II epitope (263-270) in 5 humanized transgenic mice and in rheumatoid arthritis." Proceedings of the National Academy of Sciences of the USA.2002. 99(15) 9960-9965.
Holmdahl R. et al., "The molecular pathogenesis of collagen-induced arthritis in mice—a model for rheumatoid arthritis," Ageing Res Rev. 2002;1: 135-47.
Chin R. K., et al., "Lymphotoxin Pathway-Directed, Autoimmune Regulator-Independent Central Tolerance to Arthritogenic Collagen," J Immunol. 2006;177: 290-7.
Aho, K., Palosuo, T., Raunio, V., Puska, P., Aromaa, A. & Salonen, J.T., "When does rheumatoid arthritis , start?" (1985) Arthritis Rheum 28, 485-489.
Rantapaa-Dahlqvist, S., de Jong, B. A., Berglin, E., Hallmans, G., Wadell, G., Stenlund, H., Sundin, U. & van Venrooij, W. J., "Antibodies against cyclic citrullinated peptide and IgA rheumatoid factor predict the development of rheumatoid arthritis" (2003) Arthritis Rheum 48, 2741-9.
Berglin, E., Padyukov, L., Sundin, U., Hallmans, G., Stenlund, H., Van Venrooij, W. J., Klareskog, L. & Dahlqvist, S. R., A combination of autoantibodies to cyclic citrullinated peptide (CCP) and HLA-DRB1 locus antigens is strongly associated with future onset of rheumatoid arthritis (2004) Arthritis Res Ther 6, R303-8.
Van Gaalen, F. A., van Aken, J., Huizinga, T. W., Schreuder, G. M., Breedveld, F. C., Zanelli, E., van Ven- rooij, W. J., Verweij, C. L., Toes, R. E. & de Vries, R. R., "Association between HLA class II genes and autoantibodies to cyclic citrullinated peptides (CCPs) influences the severity of rheumatoid arthritis," (2004) Arthritis Rheum 50, 2113-21.
Corrigall, V. M. et al., "The Human Endoplasmic Reticulum Molecular Chaperone BiP Is an Autoantigen for Rheumatoid Arthritis and Prevents the Induction of Experimental Arthritis," (2001) J Immunol 166, 1492-8.
Fritsch, R. et al., "Characterization of Autoreactive T Cells to the Autoantigens Heterogeneous Nuclear Ribonucleoprotein A2 (RA33) and Filaggrin in Patients with Rheumatoid Arthritis" (2002) J Immunol 169, 1068-76.
Cook, A. D., Rowley, M. J., Mackay, I. R., Gough, A. & Emery, P., "Antibodies to Type II Collagen in Early Rheumatoid Arthritis" (1996) Arthritis Rheum 39, 1720-1727.
Holm, B., Baquer, S. M., Holm, L, Holmdahl, R. & Kihlberg, J., "Role of the Galactosyl Moiety of Collagen Glycopeptides for T-Cell Stimulation in a Model for Rheumatoid Arthritis," (2003) Bioorganic and Medicinal Chemistry 11, 3981-7.
Scott, C. A., Garcia, K. C, Carbone, F. R., Wilson, I. A. & Teyton, L., "Role of Chain Pairing for the Production of Functional Soluble IA Major Histocompatibility Complex Class II Molecules" (1996) J Exp Med 183, 2087-95.
Bunch, T. A., Grinblat, Y. & Goldstein, L. S., "Characterization and use of the *Drosophila metallothionein* promoter in cultured *Drosophila melanogaster* cells" (1988) Nucleic Acids Res 16, 1043-61.
Andersson, M. & Holmdahl, R., "Analysis of type II collagen-reactive T cells in the mouse. I. Different regulation of autoreactive vs. non-autoreactive anti-type II collagen T cells in the DBA/1 mouse" (1990) Eur J Immunol 20, 1061-1066.
Broddefalk, J., Backlund, J., Almqvist, F., Johansson, M., Holmdahl, R. & Kihlberg, J., "T Cells Recognize a Glycopeptide Derived from Type II Collagen in a Model for Rheumatoid Arthritis" (1998) J Am Chem Soc 120, 7676-7683.
Holmdahl, R., Klareskog, L., Andersson, M. & Hansen, C., "High antibody response to autologous type II collagen is restricted to H-2q" (1986) Immunogenetics 24, 84-89 (Abstract only).
Raposo, Merky, et al., "T cells specific for post-translational modifications escape intrathymic tolerance induction," 2018, Nature Communications 9 (1): 353.
Ponchel et al., "CD4+ T-cell subsets in rheumatoid arthritis," Int. J. Clin. Rheumatol. (2012) 7(1), 37-53.
Van Eden et al., "Cloning of the mycobacterial epitope recognized by T lymphocytes in adjuvant arthritis," Nature 331; 171-172 Jan. 14, 1988.
Van Eden et al., "Arthritis induced by a T-lymphocyte clone that responds to *Mycobacterium tuberculosis* and to cartilage proteoglycan," PNAS 1985; 5117-5120, Abstract.
Vanderlugdt et al., "Epitope spreading in immune-mediated diseases: implications for immunotherapy," Nature Reviews Immunology 2, 85-95 (2002) Abstract.
Vanderlugdt et al., "Epitope Spreading," Current Opinion in Immunology, vol. 8, Issue 6, Dec. 1996, pp. 831-836, Abstract.
Bajtner et al., "Chronic development of collagen-induced arthritis is associated with arthritogenic antibodies against specific epitopes on type II collagen," Arthritis Research & Therapy vol. 7 No. 5 2005.
Bevaart et al., "Evaluation of Therapeutic Targets in Animal Models of Arthritis," Arthritis & Rheumatism. 62, 2192-2205 (2010).
Freysdottir, "Mucosal tolerance to KLH reduces BSA-induced arthritis in rats—an indication of bystander suppression," J Clin Immunol. May 2007;27(3):284-93 Abstract.
Kalandadze et al., "Expression of Recombinant HLA-DR2 Molecules," (J. Biol. Chem. 1996, 271 (33), 20156-20162) (Year: 1996).
Cresswell, P, "Assembly, Transport, and Function of MHC Class II Molecules," (Annual Rev. Immunol. 1994, 12:259-293) (Year: 1994).
Latham et al. "Ex Vivo Characterization of the Autoimmune T Cell Response in the HLA-DRI Mouse Model of Collagen-Induced Arthritis Reveals Long-Term Activation of Type II Collagen-Specific Cells and Their Presence in Arthritic Joints," (J. Immunol. Jan. 4, 2005, 174: 3978-3985) (Year: 2005).
Batsalova et al., "Mice Producing Less Reactive Oxygen Species Are Relatively Resistant to Collagen Glycopeptide Vaccinationagainst Arthritis" J_ Immunol. (2010) 185;2701-2709.
Cecconi,V., et al., "Use of MHC Tetramers to Investigate CD4+ T Cell Responses: Problems and Solutions," Cytometry Part A, 2008; 73A:1010-1018.
Cumberbatch et al., "Chicken major histocompatibility complex class II molecules of the B19 haplotype present self and foreign peptides," Animal Genetics, No. 37, pp. 393-396, 2006.
Krco et al, "Characterization of the Antigenic Structure of Human Type II Collagen," The Journal of Immunology, No. 156, pp. 2761-2768, 1996.
Holmdahl, R. et al., "Genetic Analysis of Mouse Model" (1998) in Human Genome Methods, ed. Adolpho, K. W. (CRC press, New York), pp. 215-238.
Von Delwig et al. "The Impact of Glycosylation on HLA-DRI-Restricted T Cell Recognition of Type II Collagen in a Mouse Model," (Arthritis & Rheumatism, Feb. 1, 2006, 54(2): 482-491) (Year: 2006).
Rammensee et al., ("MHC Ligands and Peptide Motifs," 1997, Landes Bioscience, Austin, Texas, pp. 300-301) (Year: 1997).

(56) References Cited

OTHER PUBLICATIONS

Nelson et al. "Identification of two distinct properties of class II major histocompatibility complex associated peptides," (PNAS, 1993, 90: 1227-1231) (Year 1993).
Holm, el. al., "An Improved Synthesis of a Galactosylaled Hydroxylysine Building Block and its use in Solid-Phase Glycopeptide Synthesis," Tetrahedron, 2000, vol. 56, pp. 1579-1586.
Backlund et al. "Glycosylation of type II collagen is of major importance for T cell tolerance and pathology in collagen-induced arthritis." European Journal of Immunology_2002. 32(12):3776-84.
Broddefalk et al. "Use of acid-labile protective groups for carbohydrate moieties in synthesis of glycopeptides related to type II collagen." Tetrahedron. 1998. 54, 12047-12070.
Corthay et al. "Epitope glycosylation plays a critical role for T cell recognition of type II collagen in collagen-induced Arthritis." European Journal of Immunology_ 1998. 28(8), 2580-2590.
Dzhambazov et al., "The major T cell epitope on type II collagen is glycosylated in normal cartilage but modified by arthritis in both rats and humans." European Journal of Immunology_2005. 35(2), 357-366.
Holm et al., "Glycopeptide specificity of helper T cells obtained in mouse models for rheumatoid arthritis." Chembiochem. 2002 3(12), 1209-1222.
Kjellen et al., "The structural basis of MHC control of collagen-induced arthritis; binding of the immunodominant type II collagen 256-270 glycopeptide to H-2Aq and H-2Ap molecules." European Journal of Immunology_ 1998. 28(2):755-767.
Sareila et al., "Reactive Oxygen Species Regulate Both Priming and Established Arthritis, but with Different Mechanisms," Antioxidants & Redox Signaling, 2017, 27(18):1473-1490.
Huan et al., "MHC Class II Derived Recombinant T Cell Receptor Ligands Protect DBA/1LacJ Mice from Collagen-Induced Arthritis," The Journal of Immunology, 2008, 180: 1249-1257.
Benson et al. "Arthritis in space and time—To boldly go!" FEBS Letters, 2011, vol. 585, No. 23, pp. 3640-3648.
Dzhambazov et al. "Therapeutic Vaccination of Active Arthritis with a Glycosylated Collagen Type II Peptide in Complex with MHC Class II Molecules," The Journal of Immunology, Jan. 2006, vol. 176, pp. 1525-1533.
Sakurai et al. "Analog peptides of type II collagen can suppress arthritis in HLA-DR4 (DRB1*0401) transgenic mice," Arthritis Research & Therapy, Sep. 2006, vol. 8, No. 5, R150, 7 pages.
International Search Report and Written Opinion for International (PCT) Patent Application No. PCT/EP2020/072287, dated Oct. 12, 2020, 12 pages.

* cited by examiner

A)

B)

(A)

(B)

(A)

(B)

(A)

(B)

(C)

(A)

Lysine

Hydroxylysine

Gal-hydroxylysine

Glc-Gal-Hydroxylysine (B)

1 3 4 7 17 18 20 wt ctl 70 kDa

PRODUCTION OF MHC II/CII COMPLEXES

CROSS REFERENCE TO RELATED APPLICATIONS

This application is a national stage application under 35 U.S.C. 371 and claims the benefit of PCT Application No. PCT/EP2020/072287 having an international filing date of 7 Aug. 2020, which designated the United States, and which PCT application claimed the benefit of Europe Patent Application No. 19191094.2 filed 9 Aug. 2019, the contents of each of which are incorporated herein by reference in their entireties.

REFERENCE TO SEQUENCE LISTING

This application contains a Sequence Listing submitted as an electronic text file named "Sequence_listing_AS_FILED.TXT", having a size in bytes of 33,000 bytes, and created on 7 Aug. 2020. The information contained in this electronic file is hereby incorporated by reference in its entirety pursuant to 37 CFR § 1.52(e)(5).

The present invention relates to in situ glycosylated MHC II/CII peptide complexes, i.e., complexes naturally glycosylated during recombinant protein expression in the host cell. The invention further relates to methods of producing glycosylated MHC II/CII peptide complexes in mammalian cells. Furthermore the invention relates to the use of such post-translationally modified, preferably glycosylated MHC II/CII peptide complexed for use in treating arthritis.

SEQUENCE LISTING

The instant application contains a Sequence Listing, which has been submitted electronically in ASCII format and is hereby incorporated by reference in its entirety. Said ASCII copy, created on Nov. 12, 2025, is named 13102-401201_ST25_12Nov2025 and is 35,063 bytes in size.

TECHNOLOGICAL BACKGROUND

Rheumatoid arthritis (RA) is a common, severe disease representing a major health concern with 4-7 million affected people in Europe. It is caused by an aberrant autoimmune inflammation of joints associated with pain, progressive cartilage and bone destruction leading to functional disability and ultimately immobility/invalidity if not adequately treated. Today's pharmaceutical treatment is initiated immediately upon establishment of the clinical diagnosis and is effective in 60-70% of the cases, but does not achieve cure from the disease. Drug treatment predominantly targets common effector pathways of inflammation thereby causing broad immunosuppressive effects associated with an increased risk for infection.

The immunogenetics of RA suggests a key role for aberrant pathways of T-cell activation in the initiation and/or perpetuation of disease. In the T-cell activation process, CD4+ T-cells are engaged by antigenic peptide fragments complexed with human leukocyte antigen (HLA) class II molecules (human major histocompatibility complex (MHC) class II), leading to their activation in the context of co-stimulatory signals provided by professional antigen presenting cells. The strongest evidence supporting a role for CD4+ T cells in disease pathogenesis is the genetic association between RA and certain alleles of the HLA-DRB1 locus coding for an amino acid consensus motif Q/R R/K RA A on the beta-chain of the peptide binding pocket of the MHC class II molecule HLA-DR (amino acid position 70-74, the so called "shared epitope") (Gregersen P K et al., Arthritis Rheum. 1987; 30:1205-1213). Compelling evidence for a pathogenic role of T cells in RA is further provided by their frequent detectability in inflammatory synovial infiltrates of moderate to severe disease indicating their collaboration with B cells in local immune reactions to promote the maturation of specific autoantibody responses. Moreover, an impaired CD4+CD25(hi) regulatory T cell (Treg) function has been suggested to be involved in the pathogenesis of RA. Accordingly, the dysregulated chronically activated T cell compartment in RA represents a key target for therapeutic immunomodulatory intervention.

RA is today believed to start many years before clinical onset. RA as polygenetic disease with the above mentioned shared-epitope encoding alleles at the HLA-DRB1 locus as the strongest risk factor, develops in respectively predisposed individuals. However, yet ill-defined environmental and/or life style factors (smoking) are also involved in triggering an autoimmune response associated with the generation of antibodies to IgG (rheumatoid factors) and to citrullinated proteins (ACPA) that can persist in arthritis prone but still healthy individuals for a preclinical period of up to two decades. Around clinical onset, an immune response to type II collagen (CII) and to citrullinated CII is detectable (Burkhardt H et al., Eur J Immunol. 2005; 35:1643-52). CII is the major protein component in joint cartilage. RA patients that carry the DRB1*0401 allele (50% of Caucasian RA-patients) have been demonstrated to harbor T cells in their repertoire that specifically respond to a major CII epitope corresponding to the amino acid sequence 259-273 of the triple helical CII region. However the T cell determinant critical for activation of the T cell receptor (TCR) is dependent on the physiologically galactosylated hydroxylysine residue at position 264 (Baecklund J. et al., Proc Natl Acad Sci US A. 2002; 99:9960-5).

The most commonly used animal model for RA is collagen-induced arthritis (CIA) in mice. Experimental arthritis is MHC class II dependent, associated with the murine class II allele Aq and dependent on T cell recognition of the galactosylated 259-273 CII-epitope (Holmdahl R. et al. Ageing Res Rev. 2002; 1: 135-47). CIA is used as a standard model for testing the therapeutic efficiency of new compounds with antiarthritic potential in drug development. Thus a variety of protocols have been developed to induce antigen specific tolerance and one of the candidate antigens in preventing and curing arthritis through vaccination has been CII. The most efficient protocol in adult mice, and so far without any observable side effects, is to induce tolerance by intravenous injection of a recombinant protein complex consisting of the extracellular domains of the MHC class II molecule Aq with the major antigen CII peptide in the binding pocket i.e. the galactosylated CII259-273 peptide, or Aq/galCII complex (Dzhambazov B et al. J Immunol 2006; 176: 1525-1533). Injection of the Aq/galCII complex after immunization with CII, but before the onset of arthritis, led to an almost complete prevention of arthritis development and treatment of mice with a chronic relapsing arthritis led to down-regulation of the inflammatory activity. The tolerogenic Aq/galCII effect was dominant as its antiarthritic potential could be transferred with T cells from treated mice to naïve recipients.

Complexes of Aq containing CII peptide without galactosylation at position 264 remained without effect. The reason for this remarkably selective regulatory effect is likely related to the fact that galactosylated CII is expressed only in cartilage (Baecklund J. et al., Proc Natl Acad Sci USA. 2002; 99:9960-5) whereas non-glycosylated CII is expressed also in the thymus (Chin R. K., et al., J Immunol. 2006; 177: 290-7). Thus, the T cell response to unglycosylated CII is regulated by central tolerance whereas the T cell response to the galactosylated antigen is regulated by peripheral tolerance mechanisms. A disturbance of the physiologic peripheral self-tolerance especially to structural components of the diarthrodial joints as being a major driving force in RA pathogenesis has therefore been suggested and its reestablishment is the rationale for the development of a tolerogenic treatment strategy. This approach consists of the parenteral administration of DR4/galCII complexes to biomarker selected human RA-patients identified as carriers of the DRB1*0401 allele by preceding genotyping to induce immune regulatory T cells that down-regulate arthritogenic T cell responses by bystander suppression. By contrast to conventional treatment approaches the mechanism of action consists of a selective immunomodulation of arthritogenic adaptive immune responses while leaving protective immunity unaffected. It is a personalized or HLA-restricted treatment approach that is confined to patients with a certain HLA allele, such as DRB1*0401 positive patients. In addition, preclinical data in CIA treatment suggest that the DR4/galCII complex has the potential to achieve a therapeutic effect in established RA a well as a prophylactic effect in individuals at risk of developing RA, i.e., before disease manifestation. Accordingly, the mode of action is fundamentally different from already established therapies in RA.

WO 2007/058587 A1 relates to a "compound comprising an autoantigenic peptide and a carrier with a MHC binding motif and discloses a compound comprising (a) a peptide and (b) a carrier, wherein said peptide has at least the motif X-X-X-X-X-X-X and wherein at least one amino acid residue X is glycosylated. Furthermore, the peptide is being linked to the peptide binding protein and said carrier comprises at least a MHC binding motif, wherein the linking may be covalently. However, the peptide is not expressed together with the MHC II protein by the same host cell or is linked to the MHC II protein via a linker peptide. The MHC II proteins were initially expressed in SL2 cells with a replacement peptide in the binding groove and then loaded with the peptide in vitro.

Production of MHC II proteins in HEK cells have been described before (Sareila et al., Antioxidants & Redox Signaling, 2017, 27(18):1473-1490), however, again the synthetic glycosylated peptide is not expressed together with the MHC II protein, but is loaded onto the MHC II protein following production and is therefore not linked to the MHC II protein with a linker peptide. Synthesis of the galactosylated CII peptide is both time- and cost consuming. Also, loading of the synthetic peptide to the recombinant MHC class II molecule is not trivial and difficult to upscale, particularly because the peptide needs to be added in excess. Thus, there is a need for a more simple production method that can be up-scaled for the production of relevant amounts for therapeutic use.

SUMMARY OF THE INVENTION

The present invention relates to a composition comprising recombinant MHC II/CII peptide complexes comprising (a) an extracellular region of an MHC class II alpha chain comprising at least an alpha 1 domain; (b) an extracellular region of an MHC class II beta chain comprising at least a beta 1 domain; and (c) a collagen II peptide (CII peptide) fused to the N-terminus of the MHC class II alpha chain or the MHC class II beta chain by a linker peptide, preferably to the MHC class II beta chain; wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), and wherein the MHC II/CII peptide complexes comprise a post-translationally modified CII peptide, preferably wherein the first lysine residue of the CII peptide is hydroxylysine (Hyl) or is O-glycosylated Hyl. In one embodiment the first lysine residue is galactosyl-hydroxylysine.

In certain embodiments the CII peptide comprises the amino acid sequence of AGFKGEQGPKG (SEQ ID NO: 1), AGFKGEQGP$X_1$G (SEQ ID NO: 2), AGFKGE$X_2$GPKG (SEQ ID NO: 3), AGFKG$X_3$QGPKG (SEQ ID NO: 4), AGFK$X_4$EQGPKG (SEQ ID NO: 5), AGFKGE$X_2$GP$X_1$G (SEQ ID NO: 6), AGFKG$X_3$QGP$X_1$G (SEQ ID NO: 7) and AGFK$X_4$EQGP$X_1$G (SEQ ID NO: 8), wherein $X_1$ is any of the proteinogenic amino acids except K, preferably R, A, G or Q, more preferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L. Preferably $X_2$, $X_3$ or $X_4$ are not K, more preferably $X_1$, $X_2$, $X_3$ or $X_4$ are not K. In certain embodiments the CII peptide comprises the amino acid sequence of AGFKGEQGPKG (SEQ ID NO: 1) or AGFKGEQGP$X_1$G (SEQ ID NO: 2), preferably of AGFKGEQGPKGEP (SEQ ID NO: 10) or AGFKGEQGP$X_1$GEP (SEQ ID NO: 11), more preferably of GIAGFKGEQGPKGEP (SEQ ID NO: 13) or GIAGFKGEQGP$X_1$GEP (SEQ ID NO: 14).

Preferably the MHC class II is HLA-DR and at least the alpha 1 domain is DRA*0101 and at least the beta 1 domain is selected from DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401. In certain embodiments the CII peptide comprises only the first lysine residue and any further K is mutated, preferably mutated to R, A, G or Q, more preferably to R.

In invention further relates to a method for producing a MHC II/CII peptide complex comprising a post-translationally modified (e.g. O-glycosylated) CII peptide comprising (a) transfecting a mammalian cell with (i) a polynucleotide encoding an extracellular region of the MHC II alpha chain comprising at least an alpha 1 domain; (ii) a polynucleotide encoding an extracellular region of the MHC II beta chain comprising at least a beta 1 domain; and (iii) a polynucleotide encoding a collagen II peptide (CII peptide) fused to the N-terminus of the MHC class II alpha chain or the MHC class II beta chain by a linker peptide, preferably to the MHC class II beta chain, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6) and AGFKGXQGPXG (SEQ ID NO: 7), AGFKXEQGPXG; (SEQ ID NO: 8) (b) cultivating the mammalian cells under conditions suitable to produce the MHC II/CII peptide complex, and (c) harvesting a cell supernatant and optionally cells comprising the MHC II/CII peptide complex comprising a post-translationally modified CII peptide, preferably wherein the first lysine residue of the CII peptide is hydroxylysine (Hyl) or is O-glycosylated Hyl; optionally further comprising a step of analysing the post-translational modification, preferably the glycosylation profile, of the CII peptide of the MHC II/CII peptide complex. In one embodiment the first lysine residue is galactosyl-hydroxylysine.

In certain embodiments the CII peptide comprises the amino acid sequence of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6) and AGFKGXQGPXG (SEQ ID NO: 7), AGFKXEQGPXG. (SEQ ID NO: 8); wherein $X_1$ is any of the proteinogenic amino acids except K, preferably R, A, G or Q, more preferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L. Preferably $X_2$, $X_3$ or $X_4$ are not K, more preferably $X_1$, $X_2$, $X_3$ or $X_4$ are not K. In certain embodiments the CII peptide comprises the amino acid sequence of AGFKGEQGPKG (SEQ ID NO: 1) or AGFKGEQGP$X_1$G, (SEQ ID NO: 2) preferably of AGFKGEQGPKGEP (SEQ ID NO: 10) or AGFKGEQGP$X_1$GEP (SEQ ID NO: 11), more preferably of GIAGFKGEQGPKGEP (SEQ ID NO: 13) or GIAGFKGEQGP$X_1$GEP (SEQ ID NO: 14).

In certain embodiments the CII peptide comprises only the first lysine residue and any further K is mutated, preferably mutated to R, A, G or Q, more preferably to R. Suitable mammalian cell comprises enzymes to post-translationally modify lysine residues in collagen, comprising hydroxylating lysine to hydroxylysine (Hyl) and galactosylating Hyl to galactosylhydroxylysine (Gal-Hyl), such as a lysylhydroxylase (e.g., lysylhydroxylase 1 (LH1) and/or lysylhydroxylase 2 (LH2)) and a collagen galactosyltransferase (e.g., collagen galactosyltransferase GLT25D1 and/or GLT25D2. In one embodiment the mammalian cell is a kidney cell, a fibroblast cell or an osteoblast cell, preferably a kidney cell, more preferably a HEK 293 cell line. In another embodiment the mammalian cell is a genetically engineered cell recombinantly expressing a lysylhydroxylase and a collagen galactosyltransferase, preferably lysylhydroxylase 1 (LH1) and/or lysylhydroxylase 2 (LH2) and collagen galactosyltransferase GLT25D1 and/or GLT25D2. Preferably the mammalian cell lacks galactosylhydroxylysyl glucosyltransferase activity.

Also provided is a recombinant MHC II/CII peptide complex comprising a post-translationally modified CII peptide, obtained by the method according to the invention. In one embodiment the first lysine residue of the CII peptide is hydroxylysine (Hyl) or is O-glycosylated Hyl. In another aspect the invention relates to a composition comprising a recombinant MHC II/CII peptide complex comprising a post-translationally modified CII peptide, obtained by the method according to the invention. Preferably the first lysine residue of the CII peptide is hydroxylysine (Hyl) or is O-glycosylated Hyl.

Also provided is the composition according to the invention or the recombinant MHC II/CII peptide complex according to the invention for use in treating chronic inflammatory disease, wherein the chronic inflammatory joint disease is preferably selected from the group consisting of rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme disease, Meniere diseases, autoimmune inner ear disease (AIED), or Still's disease.

In yet another aspect the invention relates to a MHC II/CII peptide complex tetramer comprising the recombinant MHC II/CII peptide complex(es) of the composition according to the invention or the recombinant MHC II/CII peptide complex comprising a post-translationally modified CII peptide according to the invention. Preferably the tetramer comprises a multimerisation molecule, such as streptavidin.

In yet another aspect, the invention relates to a method for preparing a MHC II/CII peptide complex tetramer comprising the steps of (a) providing the composition according to the invention or the recombinant MHC II/CII peptide complex comprising the post-translationally modified CII peptide according to the invention, wherein the MHC II/CII peptide complex comprises at least one N-terminal biotinylation; (b) contacting the composition with a multimerisation molecule, preferably streptavidin, and optionally isolating tetramers comprising four MHC II/CII peptide complexes bound to a streptavidin.

In yet another aspect, the invention provides for an in vitro method for detecting and/or quantifying T cells specific for a given antigen, wherein the method comprises the steps of providing the MHC II/CII peptide complex tetramer according to the invention; contacting the MHC II/CII peptide complex tetramer with a sample of a subject, preferably a sample containing peripheral blood cells of said subject; and detecting the label of the MHC II/CII peptide complex tetramer bound to T cells.

DETAILED DESCRIPTION OF PREFERRED EMBODIMENTS

Figure 1:
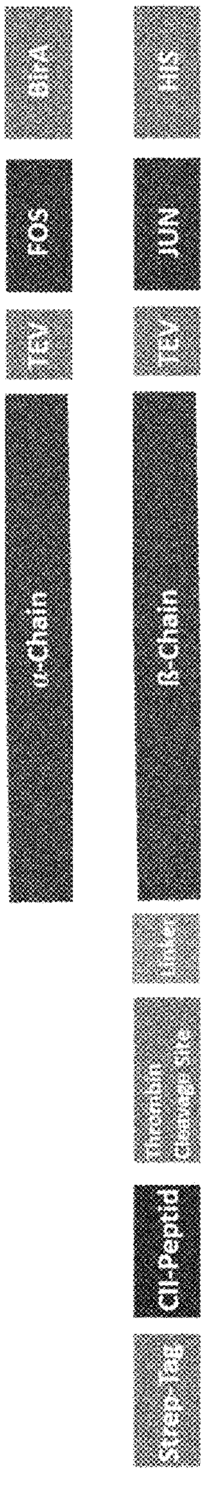
FIG. 1: Schematic drawing of an MHC II/CII peptide complex. MHC II molecule with a covalently bound CII259-273 peptide. BirA: biotinylation site, HIS: poly (6×) histidine tag, JUN/FOS: complementary domains of a leucine zipper (heterodimerisation domain), TEV: Tobacco Etch Virus (TEV) cysteine protease cleavage site, Linker: Gly-Ser linker peptide, thrombin cleavage site, strep-tag, CII peptide 259-273.

The general embodiments "comprising of" or "comprised of" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "protein" is used interchangeably with "amino acid sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties.

The term “polypeptide” typically refers to a sequence of more than 20 amino acids and the term “peptide” means sequences with up to 20 amino acids in length. However, the terms may be used interchangeably. A protein may form multimers such as dimers, wherein the dimer may be a heterodimer or a homodimer. The MHC II/CII peptide complex according to the invention comprise an extracellular region of an MHC class II alpha chain and an extracellular region of an MHC class II beta chain, which typically form a heterodimer which forms the binding groove to harbor the collagen II peptide fused to the N-terminus of one of the chains. However, the person skilled in the art will understand that two proteins forming a heterodimer can also be generated as a fusion protein forming a single polypeptide chain with the domains linked to each other, optionally via a flexible linker, i.e. a single chain heterodimer.

A “fusion protein” is defined as a protein which contains the complete sequences or any parts of the sequences of two or more originally separate natural or modified proteins. Fusion proteins can be constructed by genetic engineering approaches using recombinant DNA techniques by fusing the two or more genes or cDNAs, or parts thereof, that originally encode the two or more originally separate natural or heterologous proteins, or parts thereof. This results in a fusion protein with functional properties derived from each of the original proteins. Thus, a peptide or protein is linked to another protein by a peptide bond or preferably a linker peptide.

The term “genomic DNA”, or “genome” is used interchangeably and refers to the heritable genetic information of a host organism. The genomic DNA comprises the DNA of the nucleus (also referred to as chromosomal DNA) but also of other cellular organelles (e.g., mitochondria).

The term “gene” as used herein refers to a DNA locus of heritable genomic sequence which affects an organism’s traits by being expressed as a functional product or by regulation of gene expression. Genes and polynucleotides may include introns and exons as in a genomic sequence, or just the coding sequences as comprised in a cDNA, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter.

The terms “nucleic acid”, “nucleotide”, and “polynucleotide” as used herein are used interchangeably and refer to a single or double-stranded polymer of deoxyribonucleotide bases or ribonucleotide bases read from the 5' to the 3 end and include double stranded DNA (dsDNA), single stranded DNA (ssDNA), single stranded RNA (ssRNA), double stranded RNA (dsRNA), genomic DNA, cDNA, cRNA, recombinant DNA or recombinant RNA and derivatives thereof, such as those containing modified backbones. Preferably, a polynucleotide, particularly to be stably integrated into the mammalian genome, is a DNA or cDNA. Polynucleotides according to the invention can be prepared in different ways (e.g. by chemical synthesis, by gene cloning etc.) and can take various forms (e.g. linear or branched, single or double stranded, or a hybrid thereof, primers, probes etc.). The term “nucleotide sequence” or “nucleic acid sequence” refers to both the sense and antisense strands of a nucleic acid as either individual single strands or in the duplex.

The term “recombinant polynucleotide” as used herein refers to a polynucleotide derived from a different cell, organism or a different species from the recipient, e.g., a CHO cell or a HEK 293 cell, and introduced into the recipient using recombinant techniques. In the context of the present invention the skilled person would understand that it refers to a DNA or cDNA. A recombinant polynucleotide may also be referred to as transgene or a heterologous polynucleotide. Thus, it may be a gene or an open reading frame (ORF) coding for a recombinant protein. In the context of mammalian cells, such as HEK 293 or CHO cells “recombinant polynucleotide” refers to a polynucleotide derived from a different cell or artificially synthesized. The term “recombinant” refers to molecules such as polypeptides or polynucleic acid molecules formed by laboratory method of genetic recombination, such as molecular cloning. Such methods bring together genetic material from multiple sources or create sequences that do not naturally exist. When used with reference to portions of a nucleic acid, “recombinant” also includes a polynucleotide comprising two or more sequences that are not found in the same relationship to each other in nature or a polypeptide encoded by said polynucleotide. Recombinant may therefore also refer to a polynucleotide sequence, such as a gene or transgene, or a portion thereof, derived from the same cell line, but being inserted into the genome in a location in which it is not typically found, or a gene introduced into a cell of an organism in which it is not typically found.

As used herein a “recombinant polynucleotide”, “recombinant gene” or “recombinant sequences” can be introduced into a target cell or host cell directly or preferably by using an “expression vector”, preferably a mammalian expression vector. Methods used to construct vectors are well known to the person skilled in the art. Vectors may include, but are not limited to, plasmid vectors, cosmids, artificial/mini-chromosomes (e.g. ACE), or viral vectors such as retrovirus, adenovirus, adeno-associated virus and herpes simplex virus. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art. Usually expression vectors also comprise an expression cassette encoding a selectable marker, allowing selection of host cells carrying said expression marker.

The term “cytokine” refers to small proteins, which are released by cells and act as intercellular mediators, for example influencing the behavior of the cells surrounding the secreting cell. Cytokines may be secreted by immune or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

The term “expression” as used herein refers to transcription and/or translation of a nucleic acid sequence within a host cell. The level of expression of a gene product of interest in a host cell may be determined on the basis of either the amount of corresponding RNA that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

The term "gene product" refers to both the RNA polynucleotide and polypeptide that is encoded by a gene or DNA polynucleotide.

The term "proteinogenic amino acid" as used herein refers to all amino acids that are incorporated biosynthetically into proteins during translation. The term "proteinogenic" means protein creating. In eukaryotes there are 21 genetically encoding amino acids, i.e., proteinogenic amino acids, the 20 of the standard genetic code and selenocysteine. The 20 amino acids of the standard genetic code are alanine, arginine, asparagine, aspartic acid, cysteine, glutamic acid, glutamine, glycine, histidine, isoleucine, leucine, lysine, methionine, phenylalanine, praline, serine, threonine, tryptophane, tyrosine and valine.

The term "post-translational modification" or "post-translationally modified" as used herein refers to a naturally occurring modification of a lysine residue in the CII peptide that may occur when produced in cells. The post-translational modification of a lysine residue may result in hydroxylysine (Hyl) or is O-glycosylated Hyl, such as galactosyl-hydroxylysine or glucosylgalactosyl-hydroxylysine, preferably galactosyl-hydroxylysine.

The term "domain" as used herein refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. For example, the alpha 1 domain of the MHC II alpha chain and the beta 1 domain of the MHC II beta chain each are folded polypeptide domains together forming the peptide binding groove of the MHC II molecule.

A Method for Producing a Recombinant MHC II/CII Peptide Complex in Mammalian Cells In one aspect the present invention provides a method for producing a MHC II/CII peptide complex comprising a post-translationally modified CII peptide comprising transfecting a mammalian cell with (i) a polynucleotide encoding an extracellular region of the a MHC II alpha chain comprising at least an alpha 1 domain; (ii) a polynucleotide encoding an extracellular region of the a MHC II beta chain comprising at least a beta 1 domain; and (iii) a polynucleotide encoding a collagen II peptide (CII peptide) fused to the N-terminus of the MHC class II alpha chain or the MHC class II beta chain by a linker peptide, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8) (b) cultivating the mammalian cells under conditions suitable to produce the MHC II/CII peptide complex, and (c) harvesting a cell supernatant and optionally cells comprising the MHC II/CII peptide complex comprising a post-translationally modified CII peptide. Preferable the CII peptide comprises a post-translational modification at a lysine residue, preferably at the first lysine residue of the CII peptide. In one embodiment the first lysine residue of the CII peptide is hydroxylysine (Hyl) or is 0-glycosylated Hyl. Preferably, the first lysine residue is hydroxylysine or galactosyl-hydroxylysine, even more preferably galactosyl-hydroxylysine. The term "the first lysine residue" as used herein refers to K264 of the CII peptide 261-273 (AGFK(264)GEQGPK(270)GEP; SEQ ID NO: 10) or 259-273 (GIAGFK(264)GEQGPK(270)GEP; SEQ ID NO: 13) (corresponding to amino acid position 4 in SEQ ID NOs: 1 to 12 and amino acid position 6 in SEQ ID NOs: 13-15). The method may further comprise a step of analysing the post-translational modification, such as the glycosylation profile, of the CII peptide of the MHC II/CII peptide complex. Methods for analyzing the glycosylation profile are well known in the art and include methods such as mass spectrometry. The method according to the invention is an in vitro method. Further the method comprises the use of mammalian cell lines, rather than primary cells.

In certain embodiments the CII peptide comprises the amino acid sequence of AGFKGEQGPKG (SEQ ID NO: 1), AGFKGEQGP$X_1$G (SEQ ID NO: 2), AGFKGE$X_2$GPKG (SEQ ID NO: 3), AGFKG$X_3$QGPKG (SEQ ID NO: 4), AGFK$X_4$EQGPKG (SEQ ID NO: 5), AGFKGE$X_2$GP$X_1$G (SEQ ID NO: 6), AGFKG$X_3$QGP$X_1$G (SEQ ID NO: 7) and AGFK$X_4$EQGP$X_1$G (SEQ ID NO: 8), wherein $X_1$ is any of the proteinogenic amino acids except K, preferably R, A, G or Q, more preferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L. Preferably $X_2$, $X_3$ or $X_4$ are not K, more preferably $X_1$, $X_2$, $X_3$ or $X_4$ are not K. In certain embodiments the CII peptide comprises the amino acid sequence of AGFKGEQGPKG (SEQ ID NO: 1) or AGFKGEQGP$X_1$G (SEQ ID NO: 2), preferably of AGFKGEQGPKGEP (SEQ ID NO: 10) or AGFKGEQGP$X_1$GEP (SEQ ID NO: 11), more preferably of GIAGFKGEQGPKGEP (SEQ ID NO: 13) or GIAGFKGEQGP$X_1$GEP (SEQ ID NO: 14).

The term "MHC II/CII peptide complex" as used herein refers to a soluble complex comprising the extracellular domains of an MHC II protein or part thereof forming the peptide binding groove and a collagen II peptide (CII peptide), wherein the peptide is fused (i.e., linked via a linker peptide) to the N-terminus of either the alpha or the beta chain. Preferably the CII peptide is fused to the N-terminus of the MHC class II beta chain. A MHC II protein comprises an alpha 1 domain and an alpha 2 domain, which form the extracellular domain of the alpha chain and a beta 1 domain and a beta 2 domain, which form the extracellular domain of the beta chain. The term "extracellular domain" and "extracellular region" are used synonymously herein. The alpha 1 domain and the beta 1 domain form the peptide binding groove, i.e., the site that interacts and binds the peptide, such as the CII peptide. Thus, the MHC II/CII peptide complex comprises at least the alpha 1 domain and the beta 1 domain of the MHC II protein. Preferably the MHC II/CII peptide complex comprises the alpha 1 domain, the alpha 2 domain, the beta 1 domain and the beta 2 domain of the MHC II protein. MHC class II molecules (MHC II protein) are a class of major histocompatibility complex (MHC) molecules normally found only on professional antigen-presenting cells (APCs) such as dendritic cells, mononuclear phagocytes, such as monocytes and macrophages, and B cells. The antigens presented by MHC class II molecules are derived from extracellular proteins, while MHC class I molecules present cytosolic or intracellular peptides. Extracellular proteins are endocytosed, digested and loaded onto MHC II proteins forming an MHC II/peptide complex. The loaded complex is then transferred to the cell surface, where it is presented to effector cells. In humans, the MHC protein is referred to as human leukocyte antigen (HLA). Thus, as used herein MHC II protein encompasses human HLA proteins. HLAs corresponding to MHC class II proteins are HLA-DP, HLA-DM, HLA-DOA, HLA-COB, HLA-DQ and HLA-DR. For RA there is a genetic association with certain alleles of the HLA-DRB1 locus coding for an amino acid consensus motif (Q/R R/K RA A) on the beta-chain of the peptide binding pocket of the MHC class II molecule HLA-DR (amino acid position 70-74, the so called "shared epitope"). Examples for RA associates HLA DRB1 alleles are QKRAA-coding alleles HLA_DRB1*0401 and 0409, QRRAA-coding alleles: HLA_DRB1*0404, 0405, 0408, 0101, 0102 and 1402, RRRAA-coding allele: HLA_DRB1*1001 and DKRAA-coding allele: HLA_DRB1*1303. In one embodiment, the extracellular region of the MHC class II alpha chain and the extracellular region of the MHC class II beta chain are therefore derived from HLA-DR, preferably at least the alpha 1 domain is from DRA*0101 and at least the beta 1 domain is from a HLA-DR allele selected from the group consisting of DRB1*0401, DRB1*0404 and DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404, DRB1*0101 and DRB1*0405, even more preferably DRB1*0401. More preferably the alpha 1 domain and the alpha 2 domain is from DRA*0101 (alpha 1 and 2 domain: amino acids 19-200 of SEQ ID NO: 16) and the beta 1 domain and the beta 2 domain is from a HLA-DR allele selected from the group consisting of DRB1*0401, DRB1*0404 and DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404, DRB1*0101 and DRB1*040, even more preferably DRB1*0401 (beta 1 and 2 domain: amino acids 60-250 of SEQ ID NO: 17). In mice collagen-induced arthritis (CIA) is associated with the mouse MHC II Aq allele (Aq).

The specific MHC II/CII peptide complexes used in the examples are abbreviated as follows: Aq/rCII (naturally glycosylated, rat CII), Aq/nCII (naked or non-modified, rat CII), Aq/galCII (galactosylated (Gal-Hyl at K264)), wherein the rat CII peptide used has the amino acid sequence GIAGFKGEQGPKGET (SEQ ID NO: 29) and DR4/hCII (naturally glycosylated, human), DR4/nCII (naked or non-modified, human), DR4/galCII (galactosylated (Gal-Hyl at K264), human), wherein the CII peptide used has the human amino acid sequence GIAGFKGEQGPKGEP (SEQ ID NO: 13).

The MHC II/CII peptide complex produced according to the method of the invention comprises a post-translationally modified peptide. The CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6) AGFKGXQGPXG (SEQ ID NO: 7) and AGFKXEQGPXG (SEQ ID NO: 8). In certain embodiments the CII peptide comprises the amino acid sequence of AGFKGEQGPKG (SEQ ID NO: 1), AGFKGEQGP$X_1$G (SEQ ID NO: 2), AGFKGE$X_2$GPKG (SEQ ID NO: 3), AGFKG$X_3$QGPKG (SEQ ID NO: 4), AGFK$X_4$EQGPKG (SEQ ID NO: 5), AGFKGE$X_2$GP$X_1$G (SEQ ID NO: 6) and AGFKG$X_3$QGP$X_1$G (SEQ ID NO: 7), AGFK$X_4$EQGP$X_1$G (SEQ ID NO: 8), wherein $X_1$ is any of the proteinogenic amino acids except K, preferably R, A, G or Q, more preferably R; $X_2$ is any of the proteinogenic amino acids except Q; preferably A, R, Hor G; $X_3$ is any of the proteinogenic amino acids except E, preferably A, D, Q or G; and $X_4$ is any of the proteinogenic amino acids except G, more preferably A, S, V or L. Preferably $X_2$, $X_3$ or $X_4$ is not K, more preferably $X_1$, $X_2$, $X_3$ or $X_4$ is not K. In certain embodiments the CII peptide comprises the amino acid sequence of AGFKGEQGPKG (SEQ ID NO: 1) or AGFKGEQGP$X_1$G (SEQ ID NO: 2), preferably of AGFKGEQGPKGEP (SEQ ID NO: 10) or AGFKGEQGP$X_1$GEP (SEQ ID NO: 11), more preferably of GIAGFKGEQGPKGEP (SEQ ID NO: 13) or GIAGFKGEQGP$X_1$GEP (SEQ ID NO: 14). Preferably the CII peptide comprises the amino acid sequence of AGFKGEQGPKG (SEQ ID NO: 1) or AGFKGEQGPXG (SEQ ID NO: 2), preferably of AGFKGEQGPKGEP (SEQ ID NO: 10) or AGFKGEQGPXGEP (SEQ ID NO: 11), more preferably of GIAGFKGEQGPKGEP (SEQ ID NO: 13) or GIAGFKGEQGPXGEP (SEQ ID NO: 14). The CII peptide GIAGFKGEQGPKGEP (SEQ ID NO: 13) corresponds to amino acids 259-273 of the triple helical type II collagen (CII) region. CII peptides suitable for binding into the binding pocket are from 11 to 20 amino acids in length, preferably the CII peptide is 11 to 15 amino acids in length, more preferably the CII peptide is 13 to 15 amino acids in length. In one embodiment the CII peptide comprises the amino acid sequence AGFKGEQGPKG (SEQ ID NO: 1), more preferably AGFKGEQGPKGEP (SEQ ID NO: 10) and even more preferably of GIAGFKGEQGPKGEP (SEQ ID NO: 13). In one embodiment the second K (K270) may be mutated, preferably to R, A, G or Q, more preferably to R. Thus, also encompassed are embodiments, wherein the CII peptide comprises the amino acid sequence AGFKGEQGPXG (SEQ ID NO: 2), AGFKGEQGPXGEP (SEQ ID NO: 11) and GIAGFKGEQGPXGEP (SEQ ID NO: 14), wherein X may be any proteinogenic amino acid other than K, preferably X is R, A, G or Q, more preferably X is R. Thus, in one embodiment the CII peptide comprises the amino acid sequence AGFKGEQGPRG (SEQ ID NO: 9), AGFKGEQGPRGEP (SEQ ID NO: 12) and GIAGFKGEQGPRGEP (SEQ ID NO: 15). CII peptides encompassed by the present invention are disclosed in Table 1:

TABLE 1

| Sequence | SEQ ID NO: |
|---|---|
| AGFKGEQGPKG | SEQ ID NO: 1 |
| AGFKGEQGP**X**$_1$G* | SEQ ID NO: 2 |
| AGFKGE**X**$_2$GPKG* | SEQ ID NO: 3 |
| AGFKG**X**$_3$QGPKG* | SEQ ID NO: 4 |

TABLE 1-continued

| Sequence | SEQ ID NO: |
|---|---|
| AGFK$\mathbf{X}_4$EQGPKG* | SEQ ID NO: 5 |
| AGFKGE$\mathbf{X}_2$GP$\mathbf{X}_1$G* | SEQ ID NO: 6 |
| AGFKG$\mathbf{X}_3$QGP$\mathbf{X}_1$G* | SEQ ID NO: 7 |
| AGFK$\mathbf{X}_4$EQGP$\mathbf{X}_1$G* | SEQ ID NO: 8 |
| AGFKGEQGPRG | SEQ ID NO: 9 |
| AGFKGEQGPKGEP | SEQ ID NO: 10 |
| AGFKGEQGP$\mathbf{X}_1$GEP* | SEQ ID NO: 11 |
| AGFKGEQGPRGEP | SEQ ID NO: 12 |
| GIAGFKGEQGPKGEP | SEQ ID NO: 13 |
| GIAGFKGEQGP$\mathbf{X}_1$GEP* | SEQ ID NO: 14 |
| GIAGFKGEQGPRGEP | SEQ ID NO: 15 |

*wherein $X_1$ is any of the proteinogenic amino acids except K, preferably R, A, G or Q, more preferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L.

The MHC II/CII peptide complexes produced according to the invention comprise MHC II/CII peptide complexes with a post-translationally modified CII peptide. Preferable the CII peptide comprises a post-translational modification at a lysine residue, preferably at the first lysine residue of the CII peptide. In one embodiment the first lysine residue of the CII peptide is hydroxylysine (Hyl) and/or is O-glycosylated hydroxylysine. The first lysine (K) residue in GIAGFKSGEQGPKGEP (SEQ ID NO: 15) is at position 264 of the amino acid sequence of the triple helical CII region (corresponding to amino acid position 4 in SEQ ID NOs: 1 to 12 and amino acid position 6 in SEQ ID NOs: 13-15). Thus, the "first lysine residue" as used herein may also be referred to as K264 or lysine at position 264. The second lysine residue in CII peptide: GIAGFKGEQGPKSGEP (SEQ ID NO: 15) is at position 270 of the amino acid sequence of the triple helical CII region (corresponding to amino acid position 10 in SEQ ID NOs: 1, 3-5 or 10, and amino acid position 12 in SEQ ID NO: 13). Thus, the "second lysine residue" or "further lysine residue" as used herein may also be referred to as K270 or lysine at position 270. In a preferred embodiment the MHC II/CII peptide complexes produced according to the invention comprise MHC II/CII peptide complexes wherein at least the first lysine residue is hydroxylysine and/or galactosyl-hydroxylysine.

The collagen specific post-translational galactosylation of the lysine residues in the CII peptide sequence according to the invention, particularly of the first lysine residue, i.e., lysine residue at position 264, is involved in T cell recognition via the TCR and the resulting pharmacological effects. The lysine residue in position 270 is located at the edge of the binding groove of the DR4 molecule and its galactosyl-hydroxylysine modification is considered to be less important for TCR recognition. Thus, the second or further lysine residue (corresponding to K 270) may be unmodified, hydroxylysine or galactosyl-hydroxylysine. It has been shown that the TCR of a T cell hybridoma recognizing the gal264 epitope is not affected by a K270R mutation. In a preferred embodiment the CII peptide comprises only the first lysine residue and any further K is mutated, preferably mutated to R, A, G or Q, more preferably mutated to R. Therefore CII peptides AGFKGEQGPBG (SEQ ID NO: 9), preferably AGFKGEQGPBGEP (SEQ ID NO: 12) and more preferably GIAGFKGEQGPBGEP (SEQ ID NO: 15) are also encompassed by the present invention. Mutation of the second lysine has the advantage to reduce heterogeneity of the product. Furthermore, galactosyl-hydroxylysine may be glucosylated to form glucosyl-galactosyl-hydroxylysine (Glc-Gal-Hyl), which is likely to have a negative effect on TCR recognition due to the bulkiness of the disaccharide (Glc-Gal), particularly at position K270. Thus a K270 mutation, particularly K270R, further avoids interference with binding as no disaccharide modification can be attached at this position.

The collagen II peptide (CII peptide) is fused to the N-terminus of the MHC class II alpha chain or the MHC class II beta chain by a linker peptide, preferably to the N-terminus of the MHC class II beta chain. The term "linker peptide" refers to a polypeptide consisting of multiple amino acid residues. The linker peptide may be any peptide as long as it is long and flexible enough to allow the peptide to bind to the peptide binding pocket formed by the MHC II complex. An example of a suitable linker is a Gly-Ser linker. According to the invention the CII peptide, the peptide linker and at least one of the extracellular regions of the MHC II alpha chain and the MHC II beta chain are expressed as one polypeptide and encoded by one polynucleotide. The term "fused to" as used herein means "linked to" wherein the linking is via peptide bonds using a linker peptide and therefore a fusion protein is generated. This feature structurally distinguishes the MHC II/CII peptide complex produced by the method according to the present invention from prior art complexes. In previous complexes the MHC II protein is produced with a CLIP peptide as a surrogate peptide, which is linked to one of the MHC II chains via a linker peptide comprising a peptidase cleavage site, such as a thrombin cleavage site. Thus, following production the peptide is enzymatically cleaved off and a synthetically prepared galactosylated peptide (i.e., a CII peptide carrying gal-Hyl at position K264) is loaded in vitro onto the complex. Although this synthetic galactosylated peptide may be covalently linked to the MHC II proteins, this linkage is not via a linker peptide.

While the MHC II/CII peptide complex used in the examples (SEQ ID NO: 16 and SEQ ID NO: 17) and as depicted in FIG. 1 without the signal peptide still contains an enzymatic cleavage site (thrombin cleavage site, FIG. 1) between the linker and the CII peptide, this is not necessary and is preferably removed from a therapeutic product. The linker peptide may improve stability of the product and prevent peptide loss. Thus, preferably the MHC II/CII peptide complex according to the invention does not contain an enzymatic cleavage site in the amino acid sequence between the CII peptide and extracellular region of the MHC II beta chain (or the MHC II alpha chain). Furthermore, for therapeutic purposes the MHC II/CII peptide complex (or the MHC II/CII peptide complex encoded by polynucleotide(s)) does not comprise a (1) streptavidin-tag (SAWSHPQFEK, SEQ ID NO: 30) for purification, (2) a cleavage site (e.g., a TEV cleavage site) between the MHC II a/MHC II β chain and the heterodimerisation domain and/or (3) a recognition site for the *E. coli* biotin ligase (BirA) (e.g., an AviTag) as present in the exemplified complex shown in FIG. 1 and used in the Examples. These elements were shown to have no effect on in vitro and in vivo functionality of the complex (data not shown). Preferably the MHC II/CII complex comprises the His-tag (polyhistidine-tag) or a functionally equivalent tag at the C-terminal end of the polypeptide comprising the HLA-DR alpha chain and/or the HLA-DR beta chain. An exemplary minimal HLA-DR/CII peptide complex according to the present invention may be encoded by the amino acid sequence according to SEQ ID NO:18 and SEQ ID NO:19. The person skilled in the art would understand that the peptide sequence may vary as encompassed by the claims.

Sequences for exemplary complexes as used in the examples below are as follows:

1) DR4-construct:

DR4 construct α-chain (SEQ ID NO: 16), sequence comprising a signal peptide preceding the DRA*0101 extracellular α-chain region (underlined), a TEV cleavage site (bold), a cFos domain (bold and underlined) and a biotinylation site (BirA, italic and underlined):

MKLCILLAVVAFVGLSLGIKEEHVIIQAEFYLNPDQSGEFMFDFDGDEIF

HVDMAKKETVWRLEEFGRFASFEAQGALANIAVDKANLEIMTKRSNYTPI

TNVPPEVTVLTNSPVELREPNVLICFIDKFTPPVVNVTWLRNGKPVTTGV

SETVFLPREDHLFRKFHYLPFLPSTEDVYDCRVEHWGLDEPLLKHWEFDA

-continued

SGGGENLYFQGGGGSLTDTLQAETDQLEDEKSALQTEIANLLKEKEKLEF

ILAAHGGGGSGLNDIFEAQKIEWHE

Minimal DR4 construct α-chain (SEQ ID NO: 18), sequence comprising a signal peptide preceding the DRA*0101 extracellular α-chain region (underlined), and a cFos domain (bold and underlined):

MKLCILLAVVAFVGLSLGIKEEHVIIQAEFYLNPDQSGEFMFDFDGDEIF

HVDMAKKETVWRLEEFGRFASFEAQGALANIAVDKANLEIMTKRSNYTPI

TNVPPEVTVLTNSPVELREPNVLICFIDKFTPPVVNVTWLRNGKPVTTGV

SETVFLPREDHLFRKFHYLPFLPSTEDVYDCRVEHWGLDEPLLKHWEFDA

SGGGGGGSLTDTLQAETDQLEDEKSALQTEIANLLKEKEKLEFILAAH

DR4 construct β-chain with hCII259-273 peptide (SEQ ID NO: 17), sequence comprising a signal peptide immediately preceding a Strep-Tag (bold and double underlined) and the CII peptide259-273 (italic and underline), a thrombin cleavage site (bold and dotted line) framed by a glycine linker on each site, the DRB*0401 extracellular region (underlined), a TEV cleavage site (bold), a cJun domain (bold and underlined) and a His-Tag (italic):

MKLCILLAWAFVGLSLGSAWSHPQFEKGIAGFKGEQGPKGEPSGGGSLVPRGSGGGGSGDTRP
RFLEQVKHECHFFNGTERVRFLDRYFYHQEEYVFRDSDVGEYRAVTELGRPDAEYWNSQKDLLEQ
KRAAVDTYCRHNYGVGESFTVQRRVYPEVTVYPAKTQPLQHHNLLVCSVNGFYPGSIEVRWFRNG
QEEKTGVVSTGLIQNGDWTFQTLVMLETVPRSGEVYTCQVEHPSLTSPLTVEWRARSGGGENLYF
QGGGGSRIARLEEKVKTLKAQNSELASTANMLREQVAQLKQKVMNHHHHHHH (SEQ ID NO: 17).

RFLEQVKHECHFFNGTERVRFLDRYFYHQEEYVRFDSDVGEYRAVTELGRPDAEYWNSQKDLLEQ

KRAAVDTYCRHNYGVGESFTVQRRVYPEVTVYPAKTQPLQHHNLLVCSVNGFYPGSIEVRWFRNG

QEEKTGVVSTGLIQNGDWTFQTLVMLETVPRSGEVYTCQVEHPSLTSPLTVEWRARSGGGENLYF

QGGGGSRIARLEEKVKTLKAQNSELASTANMLREQVAQLKQKVMNHHHHHHH

Minimal DR4 construct β-chain with hCII259-273 peptide (SEQ ID NO: 19), sequence comprising a signal peptide immediately preceding the CII peptide259-273 (italic and underline), the DRB*0401 extracellular region (underlined), a cJun domain (bold and underlined) and a His-Tag (italic):

MKLCILLAVVAFVGLSLGGIAGFKGEQGPKGEPSGGGSGGGGSGDTRPRF

LEQVKHECHFFNGTERVRFLDRYFYHQEEYVRFDSDVGEYRAVTELGRPD

AEYWNSQKDLLEQKRAAVDTYCRHNYGVGESFTVQRRVYPEVTVYPAKTQ

PLQHHNLLVCSVNGFYPGSIEVRWFRNGQEEKTGVVSTGLIQNGDWTFQT

LVMLETVPRSGEVYTCQVEHPSLTSPLTVEWRARSGGGGGGSRIARLEEK

VKTLKAQNSELASTANMLREQVAQLKQKVMNHHHHHHH

2) DR4-hCLIPmut construct:

DR4 construct α-chain as above (SEQ ID NO: 16)

DR4 construct β-chain with hCLIPmut (SEQ ID NO: 20), sequence comprising a signal peptide immediately preceding a Strep-Tag (bold and double underlined) and the mutated hCLIP peptide (italic and underline), a thrombin cleavage site (bold and dotted line) framed by a glycine linker on each site, the DRB*0401 extracellular region (underlined), a TEV cleavage site (bold), a cJun domain (bold and underlined) and a His-Tag (italic):

MKLCILLAVVAFVGLSLGSAWSHPQFEK*PVSKARMATGALAQA*SGGGSLVPRGSGGGGSGDTRP

RFLEQVKHECHFFNGTERVRFLDRYFYHQEEYVRFDSDVGEYRAVTELGRPDAEYWNSQKDLLEQ

KRAAVDTYCRHNYGVGESFTVQRRVYPEVTVYPAKTQPLQHHNLLVCSVNGFYPGSIEVRWFRNG

QEEKTGVVSTGLIQNGDWTFQTLVMLETVPRSGEVYTCQVEHPSLTSPLTVEWRARSGGGENLYF

QGGGGSRIARLEEKVKTLKAQNSELASTANMLREQVAQLKQKVMNH*HHHHHH*

3) Aq-rCII construct:

Aq construct α-chain (SEQ ID NO: 21), sequence comprising a signal peptide preceding the Aq extracellular α-chain region (underlined), a TEV cleavage site (bold), a cFos domain (bold and underlined) and a biotinylation site (BirA, italic and underlined):

MKLCILLAVVAFVGLSLGEDDIEADHVGFYGIVVYQSPGDIGQYTHEFDG

DEWFYVDLDKKETVWMLPEFGQLTSFDPQGGLQNIATGKHNLGGWTKRSN

FTPATNEAPQATVFPKSPVLLGQPNTLICFVDNIFPPVINITWLRNSKSV

TDGVYETSFLVNRDHSFHKLSYLTFIPSDDDIYDCKVEHWGLDEPVLKHW

-continued

EPEIPATMSELTETVSGGGENLYFQGGGGSLTDTLQAETDQLEDEKSALQ

TEIANLLKEKEKLEFILAAHGGGGS*GLNDIFEAQKIEWHE*

Aq construct β-chain with rat CII259-273 peptide (SEQ ID NO: 22), sequence comprising a signal peptide immediately preceding a Strep-Tag (bold and double underlined) and the CII peptide259-273 (italic and underline), a thrombin cleavage site (bold and dotted line) framed by a glycine linker on each site, the Aq extracellular region (underlined), a TEV cleavage site (bold), a cJun domain (bold and underlined) and a His-Tag (italic):

MKLCILLAVVAFVGLSLGSAWSHPQFEK*GIAGFKGEQGPKGET*SGGGSLVPRGSGGGGSERHFVA

QLKGECYFTNGTQRIRSVNRYIYNREEWVRFDSDVGEYRAVTELGRPDAEYWNSQPEILERTRAEV

DTVCRHNYEGVETHTSLRRLEQPNVAISLSRTEALNHHNTLVCSVTDFYPAKIKVRWFRNGQEETV

GVSSTQLIRNGDWTFQVLVMLEMTPHQGEVYTCHVEHPSLKSPITVEWRAQSESARSKSGGGENL

YFQGGGGSRIARLEEKVKTLKAQNSELASTANMLREQVAQLKQKVMNH*HHHHHH*

Aq construct β-chain with rat CII259-273 peptide without His-tag (SEQ ID NO: 23), sequence comprising a signal peptide immediately preceding a Strep-Tag (bold and double underlined) and the CII peptide259-273 (italic and underline), a thrombin cleavage site (bold and dotted line) framed by a glycine linker on each site, the Aq extracellular region (underlined), a TEV cleavage site (bold) and a cJun domain (bold and underlined):

MKLCILLAVVAFVGLSLGSAWSHPQFEK*GIAGFKGEQGPKGET*SGGGSLVPRGSGGGGSERHFVA

QLKGECYFTNGTQRIRSVNRYIYNREEWVRFDSDVGEYRAVTELGRPDAEYWNSQPEILERTRAEV

DTVCRHNYEGVETHTSLRRLEQPNVAISLSRTEALNHHNTLVCSVTDFYPAKIKVRWFRNGQEETV

GVSSTQLIRNGDWTFQVLVMLEMTPHQGEVYTCHVEHPSLKSPITVEWRAQSESARSKSGGGENL

YFQGGGGSRIARLEEKVKTLKAQNSELASTANMLREQVAQLKQKVMNH

4) Aq-mCLIPmt construct:

Aq construct α-chain as above (SEQ ID NO: 21)

Aq construct β-chain with mCLIP peptide (SEQ ID NO: 24), sequence comprising a signal peptide immediately preceding a Strep-Tag (bold and double underlined) and the mouse CLIPmt peptide (italic and underline), a thrombin cleavage site (bold and dotted line) framed by a glycine linker on each site, the Aq extracellular region (underlined), a TEV cleavage site (bold), a cJun domain (bold and underlined) and a His-Tag (italic):

MKLCILLAVVAFVGLSLGSAWSHPQFEKPVSQARMATPLLMRPSGGGSLVPRGSGGGGSERHFV

AQLKGECYFTNGTQRIRSVNRYIYNREEWVRFDSDVGEYRAVTELGRPDAEYWNSQPEILERTRAE

VDTVCRHNYEGVETHTSLRRLEQPNVAISLSRTEALNHHNTLVCSVTDFYPAKIKVRWFRNGQEET

VGVSSTQLIRNGDWTFQVLVMLEMTPHQGEVYTCHVEHPSLKSPITVEWRAQSESARSKSGGGEN

LYFQGGGGSRIARLEEKVKTLKAQNSELASTANMLREQVAQLKQKVMNHHHHHHH

Aq construct β-chain with mCLIP peptide without His-tag (SEQ ID NO: 25), sequence comprising a signal peptide immediately preceding a Strep-Tag (bold and double underlined) and the mouse CLIPmt peptide (italic and underline), a thrombin cleavage site (bold and dotted line) framed by a glycine linker on each site, the Aq extracellular region (underlined), a TEV cleavage site (bold), a cJun domain (bold and underlined):

MKLCILLAVVAFVGLSLGSAWSHPQFEKPVSQARMATPLLMRPSGGGSLVPRGSGGGGSERHFV

AQLKGECYFTNGTQRIRSVNRYIYNREEWVRFDSDVGEYRAVTELGRPDAEYWNSQPEILERTRAE

VDTVCRHNYEGVETHTSLRRLEQPNVAISLSRTEALNHHNTLVCSVTDFYPAKIKVRWFRNGQEET

VGVSSTQLIRNGDWTFQVLVMLEMTPHQGEVYTCHVEHPSLKSPITVEWRAQSESARSKSGGGEN

LYFQGGGGSRIARLEEKVKTLKAQNSELASTANMLREQVAQLKQKVMNH

Further amino acid sequences of individual elements of the constructs disclosed herein are provided below:

cFos domain (SEQ ID NO: 26): LTDTLQAETDQLEDEKSALQTE-IANLLKEKEKLEFILAAH cJun domain (SEQ ID NO: 27): RIAR-LEEKVKTLKAQNSELASTANML-REQVAQLKQKVMNH modified human CLIP-peptide (SEQ ID NO: 28): PVSKARMATGALAQA rat CII-peptide 259-273 (SEQ ID NO: 29): GIAGFKGEQGPKGET streptavidin-tag (SAWSHPQFEK, SEQ ID NO: 30)

Preferably the MHC II/CII peptide complex obtained according to the method of the invention contains at least one His-tag or functionally equivalent tag at the C-terminal end of the polypeptide comprising the HLA-DR alpha chain and/or the HLA-DR beta chain. The His-tag is preferably at least a hexahistidine-tag, more preferably at least a hepta-histidine-tag. Functionally equivalent tags are e.g., chondroitin-binding peptides. Thus, the composition may comprise MHC II/CII peptide complexes comprising chondroitin-binding peptide, preferably a chondroitin- and hyaluronic acid (also referred to as hyaluronan) binding peptide. In one embodiment the MHC II/CII peptide complex comprises at least one C-terminal chondroitin-binding peptide. Chondroitin-binding peptides are known in the art and include without being limited thereto peptides having the amino acid sequences EKRIWFPYRRF (SEQ ID NO: 31), YKTNFRRYYRF (SEQ ID NO: 32) or VLIRHFRKRYY (SEQ ID NO: 33) (Butterfield K C et al., Biochemistry. 2010 Feb. 23; 49(7):1549-55). In one embodiment the chondroitin-binding peptide comprises 5-20 amino acids, preferably 6 to 20 amino acids, more preferably 6 to 20 amino acids. To increase binding to hyaluronan a respective sequence containing the binding consensus motif is defined as follows: B(X7)B, in which B is either R or K and X7 contains no acidic residues and at least one basic amino acid (Yang B et al., EMBO J. 1994 Jan. 15; 13(2):286-96). As disclosed herein the MHC II/CII peptide complex can also bind to chondroitin sulfate via an his-tag. Thus, the chondroitin binding peptide may be a polyhistidine-tag, preferably a hexahistidine-tag, or any other amino acid sequences that increase binding affinity to chondroitin sulfate, such as. EKRIWFPYRRF (SEQ ID NO: 31), YKTNFRRYYRF (SEQ ID NO: 32) or VLIRHFRKRYY (SEQ ID NO: 33). Chondroitin and hyaluronic acid are both important components of cartilage.

The method according to the invention comprises transfecting a mammalian cell with (i) a polynucleotide encoding an extracellular region of the MHC II alpha chain comprising at least an alpha 1 domain, (ii) a polynucleotide encoding an extracellular region of the MHC II beta chain comprising at least a beta 1 domain, wherein the C II peptide is further fused to the N-terminus of either the MHC II alpha chain or the MHC II beta chain, preferably the MHC II beta chain. Transfecting as used herein means introducing the DNA into the mammalian cell using transfection methods known in the art. As used herein the term "transfection" or "transfecting" includes "transduction" and "transducing", which is often used to describe virus-mediated gene transfer into eukaryotic cells. The polynucleotide may be DNA or RNA, preferably DNA. Transfection may be transient transfection or stable transfection. Preferably the polynucleotide is present in a vector, preferably an expression vector.

Methods for stable integration are well known in the art. Briefly, stable integration is commonly achieved by transiently introducing the at least one recombinant polynucleotide or a vector containing the at least one recombinant polynucleotide into the mammalian host cell, which facilitates the stable integration of said recombinant polynucleotide(s) into the mammalian cell genome. Typically the recombinant polynucleotide is flanked by homology arms, i.e., sequences homologous to the region upstream and downstream of the integration site. A vector to introduce the recombinant polynucleotide into the mammalian cell may be chosen from a great variety of suitable vector systems, such as plasmids, retroviruses, cosmids, EBV-derived episomes, and the like. Various shuttle vectors may be used, e.g., vectors which may autonomously replicate in a plurality of host microorganisms such as *E. coli* and *Pseudomonas* sp. Before their introduction into the mammalian host cell, circular vectors may be linearized to facilitate integration into the mammalian cell genome. Methods for the introduction of vectors into mammalian cells are well known in the art and include transfection with biological methods, such as viral delivery, with chemical methods, such as using cationic polymers, calcium phosphate, cationic lipids or cationic amino acids; with physical methods, such as electroporation or microinjection.

In one embodiment the recombinant polynucleotide stably integrated into the genome of the mammalian cell is part of an expression cassette. An expression cassette comprises at least one heterologous polynucleotide coding for a gene product, such as a RNA and/or a protein, operably linked to a promoter and optionally further means controlling the expression of the gene product(s). Such means include, but are not limited to enhancers, termination signals, polyadenylation signals and a 3' untranslated region, typically containing a polyadenylation site. The promoter may be a weak promoter, or a strong promoter supporting high level expression of the gene product of interest. Said promoters include, but are not limited to CMV (cytomegalovirus) promoters, SV40 (Simian vacuolating virus 40) promoters, the RSV (Rous Sarcoma Virus) promoters, adenovirus promoters (e.g., the adenovirus major late promoter (AdMLP), CHEF-1 (CHO-derived elongation factor-1) promotors, polyoma and strong mammalian promoters such as native immunoglobulin and actin promoters or the natural promoter of the at least one heterologous polynucleotide. Preferably, the promoter is a CMV promoter or an SV40 promoter, most preferably a CMV promoter. Examples for polyadenylation signals are BGH polyA, SV40 late or early polyA; alternatively, 3'UTRs of immunoglobulin genes etc. can be used. The skilled person will further understand that the 3' untranslated region may be engineered to support high level expression, e.g., by removing instability elements, such as AREs (adenylate-uridylate rich elements).

In some embodiments, the gene product may be placed under the control of an amplifiable genetic selection marker, such as dihydrofolate reductase (DHFR), glutamine synthetase (GS). The amplifiable selection marker gene can be on the same expression vector as the secreted therapeutic protein expression cassette. Alternatively, the amplifiable selection marker gene and the secreted therapeutic protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of the gene product in the host cell or the producer cell may be achieved, e.g., by cloning multiple copies of a heterologous polynucleotide into an expression vector. Cloning multiple copies of the recombinant polynucleotide into an expression vector and amplifying the secreted therapeutic protein expression cassette (encoding for the MHC II/CII peptide complex) as described above may further be combined.

In one embodiment the polynucleotide encoding an extracellular region of the MHC II alpha chain comprising at least an alpha 1 domain is present in one vector (first polynucleotide) and the polynucleotide encoding an extracellular region of the MHC II beta chain comprising at least a beta 1 domain (second polynucleotide) is present in another vector, wherein the CII peptide is further encoded by either the first or the second polynucleotide to provide a CII peptide fused to the N-terminus of either the MHC II alpha chain or the MHC II beta chain. In an alternative embodiment the first and the second polynucleotide may be part of separate expression cassettes on the same vector.

In a further alternative embodiment the first and the second polynucleotide form a single polynucleotide encoding a single fusion polypeptide comprising the extracellular region of the MHC class II alpha chain comprising at least an alpha 1 domain; the extracellular region of the MHC class II beta chain comprising at least a beta 1 domain; and the collagen II peptide (CII peptide) fused to the N-terminus of the MHC class II alpha chain or the MHC class II beta chain by a linker peptide, preferably to the MHC class II beta chain.

In one embodiment the extracellular region of the MHC class II alpha chain comprising at least an alpha 1 domain and the extracellular region of the MHC class II beta chain comprising at least a beta 1 domain; and the collagen II peptide (CII peptide) fused to the N-terminus of the MHC class II alpha chain or the MHC class II beta chain by a linker peptide, preferably to the MHC class II beta chain; are encoded by a single polynucleotide to express a single fusion polypeptide (single chain heterodimer.

In an alternative embodiment the method comprises a first polynucleotide encoding the extracellular region of the MHC class II alpha chain comprising at least an alpha 1 domain; a second polynucleotide encoding the extracellular region of the MHC class II beta chain comprising at least a beta 1 domain; and a polynucleotide encoding the collagen II peptide (CII peptide) fused to the N-terminus of the MHC class II alpha chain or the MHC class II beta chain by a linker peptide, preferably to the MHC class II beta chain. In one embodiment the MHC class II alpha chain is fused at its C-terminal end (C-terminally) to a first functional domain of a leucine zipper heterodimerization motif and the MHC class II beta chain is fused at its C-terminal end to a second complementary functional domain of a leucine zipper heterodimerization motif. The first functional domain and the second complementary functional domain may be an acidic and a basic leucine zipper heterodimerization domain, preferably a jun-fos leucine zipper motif. In one embodiment the first and/or the second polynucleotide encodes a polyhistidine tag at the C-terminal end of the functional domain of a leucine zipper heterodimerization motif.

According to the method of the present invention the mammalian cell is cultivated under conditions suitable to produce the MHC II/CII peptide complex, and the cell supernatant and/or the cells are harvested, wherein the cell supernatant and/or the cells comprise(s) the MHC II/CII peptide complex comprising a post-translationally modified CII peptide, wherein preferably the first lysine residue of the CII peptide is hydroxylysine (Hyl) or is O-glycosylated hydroxylysine, more preferably the first lysine residue is hydroxylysine or galactosyl-hydroxylysine, more preferably galactosyl-hydroxylysine. The method may further comprise a step of analysing the post-translational modification, such as the glycosylation profile, of the CII peptide of the MHC II/CII peptide complex. Methods for analyzing the posttranslational modifications and glycosylation profile are well known in the art and include methods such as mass spectrometry.

In principle, any mammalian cell suitable for high yield protein production may be used according to the present invention, as long as it comprises enzymes to post-translationally modify lysine residues in collagen, comprising hydroxylating lysine to hydroxylysine (Hyl) and galactosylating Hyl to galactosylhydroxylysine (Gal-Hyl). The term "galactosylated" as used herein in the context of lysine includes that the lysine has been hydroxylated to hydroxylysine prior to galactosylation. The enzymes may be endogenously present in the cell or may be recombinantly expressed in the cell. Preferably the mammalian cell comprises a lysylhydroxylase (EC 1.14.11.4) and a collagen galactosyltransferase (EC 2.4.1.50), preferably lysylhydroxylase 1 (LH1) and/or lysylhydroxylase 2 (LH2) and collagen galactosyltransferase GLT25D1 and/or GLT25D2, preferably GLT25D1. These enzymes post-translationally modify collagen. Thus, these enzymes are likely to be present in cell lines producing collagen, such as kidney cells, fibroblast cells or osteoclast cells, particularly kidney cells, such as HEK 293 cells or derivatives thereof. The HEK 293 cells may be grown as adherent cells or in suspension. An example for a HEK 293 cell suitable for the method according to the invention is the HEK 293 cell or the HEK 293F cell, such as the Expi293F cell (Gibco, Cat. No. A14527, also available as cGMP banked Cat. No. 100044202). Other suitable HEK 293 cells include HEK 293T cells and/or suspension cells thereof. It was surprising that also small peptides presented by MHC II proteins can be post-translationally modified in these cells. Although the peptides are derived from collagen they are present in an entirely different (unnatural) environment within the MHC II complex. We note in this regard that naturally MHC II proteins get loaded with peptides from extracellular (post-translationally modified) proteins that get digested in the APC. Thus, the modification is already present on the endocytosed protein and is not added intracellularly. Furthermore, it has been surprising that the heterogeneous product produced when glycosylated in situ is suitable for therapy. Suitable cells can be easily screened for the enzymes required for post-translational modification of lysine residues in collagen, such as by western blot using suitable antibodies or by RNA expression, or functionally by their ability to glycosylate type II collagen or MHC II/CII peptide complexes. Methods for detecting gene or protein expression or enzyme activity and glycosylation profiles are well known in the art. In one embodiment the mammalian cell is a kidney cell, a fibroblast cell or an osteoblast cell, preferably a HEK 293 cell or cell line. HEK 293 cells have been described previously to express lysylhydroxylases PLOD1 and PLOD2 (encoding for LH1 and LH2, respectively), galactosyltransferases GLT25D1 and GLT25D2 and further PLOD3 (encoding for LH3).

CHO cells commonly used for protein production have been tested and are not able to sufficiently add post-translational modifications at the lysine residues resulting in galactosylhydroxylysine (Gal-Hyl) in collagen or in the MHC II/CII peptide complex described herein. In one embodiment the mammalian cell is a genetically engineered cell recombinantly expressing a lysylhydroxylase and a collagen galactosyltransferase. Preferably the mammalian cell is genetically engineered to recombinantly express lysylhydroxylase 1 (LH1) and/or lysylhydroxylase 2 (LH2) and collagen galactosyltransferase GLT25D1 and/or GLT25D2, preferably GLT25D1. GLT25D2 is expressed in only a few cell types and is therefore less likely to be responsible for normal collagen modification. Any mammalian cell may be genetically engineered to recombinantly express a lysylhydroxylase and a collagen galactosyltransferase, preferably lysylhydroxylase 1 (LH1) and/or lysylhydroxylase 2 (LH2) and collagen galactosyltransferase GLT25D1 and/or GLT25D2. Preferably the genetically engineered mammalian cell as described is a CHO cell, more preferably a CHO-DG44 cell, a CHO-K1 cell, a CHO-DXB11 cell, a CHO—S cell, a CHO glutamine synthetase (GS)-deficient cell or a derivative of any of these cells.

The person skilled in the art will understand that the MHC II/CII peptide complexes produced by the method according to the present invention is a heterogeneous mixture of MHC II/CII peptide complexes comprising different post-translational modifications of the CII peptide, particularly at the first and optional second lysine residue of the CII peptide. The heterogeneous mixture comprises MHC II/CII peptide complexes comprising K, Hyl, G-Hyl or GG-Hyl at the first lysine and independently K, Hyl, G-Hyl or GG-Hyl at the optional second lysine (wherein K=lysine, Hyl=hydroxylysine, G-Hyl=galactosylhydroxylysine, GG-Hyl=glucosylgalactosylhydroxylysine).

Thus, in one embodiment the harvested cell supernatant and optionally harvested cells further comprises MHC II/CII peptide complexes comprising the CII peptide, wherein the first lysine residue of the CII peptide is unmodified or glucosylgalactosyl-hydroxylysine (GG-Hyl), preferably unmodified and the optional second lysine residue of the CII peptide is independently unmodified, hydroxylysine (Hyl), galactosyl-hydroxylysine (G-Hyl) or glucosylgalactosyl-hydroxylysine (GG-Hyl), preferably unmodified, hydroxylysine (Hyl), galactosyl-hydroxylysine (G-Hyl). In one embodiment the harvested cell supernatant and optionally harvested cells do not comprise MHC II/CII peptide complexes, wherein the second lysine residue is glucosylgalactosyl-hydroxylysine. In another embodiment the harvested cell supernatant and optionally harvested cells do not comprise glucosylgalactosyl-hydroxylysine (GG-Hyl) modified MHC II/CII peptide complexes, e.g., MHC II/CII peptide complexes comprising an O-glycosylated CII peptide wherein the first and/or the optional second lysine residue are glucosylgalactosyl-hydroxylysine.

Preferably the heterogeneous mixture of MHC II/CII peptide complexes comprises at least 5%, at least 10%, at least 20% or at least 30% of G-Hyl at the first lysine (K264) of the CII peptide of total MHC II/CII peptide complexes in the mixture or the composition. Further, the heterogeneous mixture of MHC II/CII peptide complexes comprises preferably less than 50%, less than 40% or less than 30% unmodified CII peptides of total MHC II/CII peptide complexes in the mixture or the composition. In certain embodiments, the heterogeneous mixture of MHC II/CII peptides complexes comprises less than 20%, less than 10%, less than 5% and more preferably less than 1% GG-Hyl in the CII peptide of total MHC II/CII peptide complexes in the mixture or the composition. Wherein the percentage refers to percent of CII peptide in the MHC II/CII peptide complexes of total CII peptides in the MHC II/CII peptide complexes. In a particularly preferred embodiment said second lysine residue (K270) is mutated, for example mutated to Arginine (K270R). In a further embodiment the (optional) second lysine is not post-translationally modified to glucosylgalactosyl-hydroxylysine (GG-Hyl) and is present as unmodified lysine, hydroxylysine or galactosyl hydroxylysine.

In order to reduce heterogeneity of the mixture of MHC II/CII peptides complexes and bulky glucosylgalactosylhydroxylysine formation it is further advantageous if the mammalian cell lacks galactosylhydroxylysyl glucosyltransferase (EC 2.4.1.66) activity. In one embodiment t h e mammalian cell therefore lacks galactosylhydroxylysyl glucosyltransferase activity. Preferably the mammalian cell lacks lysylhydroxylase 3 (LH3). LH3 is a multifunctional enzyme comprising lysylhydroxylase (LH), galactosyltransferase (GT) and galactosylhydroxylysyl glucosyltransferase (GGT) activity, wherein the major function of the enzyme seems to be the GGT activity. LH3 activity may be deleted or reduced using knock-down or knock-out approaches. Enzyme expression can, e.g., be reduced using RNA interference, such as siRNA or shRNA.

The term "RNA interference" (RNAi) refers to sequence-specific or gene-specific suppression of gene expression (protein synthesis), without generalized suppression of protein synthesis. RNAi may involve degradation of messenger RNA (mRNA) by an RNA-induced silencing complex (RISC), preventing translation of the transcribed mRNA. The suppression of gene expression caused by RNAi may be transient or it may be more stable, even permanent. RNAi may be mediated by miRNA, siRNA or shRNA. Preferably the RNAi according to the invention is gene-specific (only one gene is targeted). Gene-specific RNAi may be mediated by siRNA or shRNA.

As used herein, the terms "small interfering" or "short interfering RNA" or "siRNA" refer to an RNA duplex of nucleotides that is targeted to a desired gene and is capable of inhibiting the expression of a gene with which it shares homology. It is formed from long double stranded RNA (dsRNA) or shRNA. The RNA duplex typically comprises two complementary single-stranded RNAs of 19, 20, 21, 22, 23, 24, 25, 26, 27, 28 or 29 nucleotides that form 17, 18, 19, 20, 21, 22, 23, 24, 25, 26 or 27 base pairs and possess 3' overhangs of two nucleotides, preferably the RNA duplex comprises two complementary single stranded RNAs of 19-27 nucleotides that form 17-25 base pairs and possess 3' overhangs of two nucleotides. siRNA is "targeted" to a gene, wherein the nucleotide sequence of the duplex portion of the siRNA is complementary to a nucleotide sequence of the mRNA of the targeted gene. The siRNA or a precursor thereof is always exogenously introduced into the cell, e.g., directly or by transfection of a vector having a sequence encoding said siRNA, and the endogenous miRNA pathway is harnessed for correct processing of siRNA and cleavage or degradation of the target mRNA. The duplex RNA can be expressed in a cell from a single construct.

As used herein, the term "shRNA" (small hairpin RNA) refers to an RNA duplex wherein a portion of the siRNA is part of a hairpin structure (shRNA). The shRNA can be processed intracellularly into a functional siRNA. In addition to the duplex portion, the hairpin structure may contain a loop portion positioned between the two sequences that form the duplex. The loop can vary in length. In some embodiments the loop is 4, 5, 6, 7, 8, 9, 10, 11, 12, 13 or 14 nucleotides in length. The hairpin structure can also contain 3' or 5' overhang portions. In some aspects, the overhang is a 3' or a 5' overhang of 0, 1, 2, 3, 4 or 5 nucleotides in length. In one aspect of this invention, a nucleotide sequence comprised in the vector serves as a template for the expression of a small hairpin RNA, comprising a sense region, a loop region and an antisense region. Following expression the sense and antisense regions form a duplex. shRNA is always exogenously introduced, e.g., by transfection of a vector having a sequence encoding said shRNA, and the endogenous miRNA pathway is harnessed for correct processing of the siRNA and cleavage or degradation of the target mRNA. Use of a vector having a sequence encoding a shRNA has the advantage over use of chemically synthesized siRNA in that the suppression of the target gene is typically long-term and stable.

Typically, siRNA and shRNA mediate mRNA repression by complete sequence complementarity (i.e., perfect base paring between the antisense strand of the RNA duplex of the small interfering RNA and the target mRNA) and are therefore specific for their target. The antisense strand of the RNA duplex may also be referred to as active strand of the RNA duplex. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. More preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides.

Alternatively, the enzyme is not expressed or the gene may be mutated or deleted. Thus, in an alternative embodiment the mammalian cell lacks galactosylhydroxylysyl glucosyltransferase activity. In certain embodiments the mammalian cell lacks the multifunctional enzyme LH3. For example the gene may be silenced or not sufficiently expressed. In other certain embodiments the mammalian cell comprises a mutant LH3 enzyme lacking galactosylhydroxylysyl glucosyltransferase activity.

In a further embodiment the mammalian cell is genetically engineered to have reduced or no galactosylhydroxylysyl glucosyltransferase activity. The PLOD3 gene encoding for LH3 may be mutated or deleted; and/or the LH3 enzyme may be a mutated LH3 enzyme lacking galactosylhydrosylysyl glucosyltransferase activity. Methods for deleting or mutating genes are well known in the art and may include the use of sequence specific DNA editing enzymes. A "sequence specific DNA editing enzyme" or a "site specific nuclease" as used herein is a protein that enables the cleavage of DNA at defined nucleotide sequences (recognition sites). Said cleavage may occur on one or both of two complementary DNA strands and thus allow, for example targeted mutagenesis, targeted deletion of specific genomic DNA sequences or result in the site-directed recombination of the cleaved target DNA with a heterologous polynucleotide. The sequence specificity of said editing enzymes may result from one or more sequence specific DNA binding protein domains within the editing enzyme, or from the enzyme binding a guide polynucleotide (e.g. guide RNA) that directs it to a DNA sequence with at least partial complementarity to said guide polynucleotide. The recognition site of said editing enzymes may therefore be altered by engineering the DNA binding protein domains, or using alternative guide polynucleotides. Multiple sequence specific DNA editing enzymes are known in the art, non-limiting examples of which are zinc finger nucleases (ZFNs), meganucleases, transcription activator-like effector nucleases (TALENs) and CRISPR associated nucleases.

Preferably the genetically engineered mammalian cell lacking galactosylhydroxylysyl glucosyltransferase activity is a HEK 293 cell or cell line. An example of a cell line that would benefit from reducing galactosylhydroxylysyl glucosyltransferase for the production of the MHC II/CII complexes according to the invention is the Expi293F cell (Gibco, Cat. No. A14527, also available as cGMP banked Cat. No. 100044202).

Galactosylhydroxylysyl glucosyltransferase activity may also be inhibited using carminic acid. Thus, the method according to the invention may comprise cultivating the mammalian cells according to step (b) in carminic acid.

The mammalian cells are preferably being established, adapted, and completely cultivated under serum free conditions, and optionally in media, which are free of any protein/peptide of animal origin. Commercially available media such as PreproGow™ HEK293 Media (PREPROTECH, USA) Expi293™ Expression Medium (Thermo Fisher, USA), HAM's F12 (Sigma, Deisenhofen, Germany,) RPPMI (Sigma), Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, CA), serum-free CHO Medium (Sigma), and protein-free CHO Medium (Sigma) are exemplary appropriate nutrient solutions. Any of the media may be supplemented as necessary with a variety of compounds, non-limiting examples of which are recombinant hormones and/or other recombinant growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. For the growth and selection of genetically modified cells expressing a selectable gene a suitable selection agent is added to the culture medium.

The Composition Comprising a Recombinant MHC II/CII Peptide Complex

In another aspect the invention provides a composition comprising recombinant MHC II/CII peptide complexes comprising (a) an extracellular region of an MHC class II alpha chain comprising at least an alpha 1 domain; (b) an extracellular region of an MHC class II beta chain comprising at least a beta 1 domain; and (c) a collagen II peptide (CII peptide) fused to the N-terminus of the MHC class II alpha chain or the MHC class II beta chain by a linker peptide, preferably to the MHC class II beta chain; wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), wherein the MHC II/CII peptide complexes comprise a post-translationally modified CII peptide. Preferable the CII peptide comprises a post-translational modification at a lysine residue, preferably at the first lysine residue of the CII peptide. In one embodiment the first lysine residue of the CII peptide is hydroxylysine (Hyl) and/or is O-glycosylated Hyl. Preferably, the first lysine residue is hydroxylysine (Hyl) and/or galactosyl-hydroxylysine, more preferably galactosyl-hydroxylysine.

The term "MHC II/CII peptide complex" refers to a soluble complex comprising the extracellular domains of an MHC II protein or part thereof forming the peptide binding groove and a collagen II peptide (CII peptide), wherein the peptide is fused (i.e., linked) to the N-terminus of either the alpha or the beta chain. Preferably the CII peptide is fused to the N-terminus of the MHC class II beta chain. A MHC II protein comprises an alpha 1 domain and an alpha 2 domain, which form the extracellular domain of the alpha chain and a beta 1 domain and a beta 2 domain, which form the extracellular domain of the beta chain. The alpha 1 domain and the beta 1 domain form the peptide binding groove, i.e., the site that interacts and binds the peptide, such as a CII peptide. Thus, the MHC II/CII peptide complex comprises at least the alpha 1 domain and the beta 1 domain of the MHC II protein. Preferably the MHC II/CII peptide complex comprises the alpha 1 domain, the alpha 2 domain, the beta 1 domain and the beta 2 domain of the MHC II protein.

For RA in humans there is a genetic association with certain alleles of the HLA-DRB1 locus coding for an amino acid consensus motif (Q/R R/K R A A) on the beta-chain of the peptide binding pocket of the MHC class II molecule HLA-DR (amino acid position 70-74, the so called "shared epitope"). Examples for RA associates HLA DRB1 alleles are QKRAA-coding alleles HLA_DRB1*0401 and 0409, QRRAA-coding alleles: HLA_DRB1*0404, 0405, 0408, 0101, 0102 and 1402, RRRAA-coding allele: HLA_DRB1*1001 and DKRAA-coding allele: HLA_DRB1*1303. The extracellular region of the MHC class II alpha chain and the extracellular region of the MHC class II beta chain are therefore derived from HLA-DR, preferably at least the alpha 1 domain is from DRA*0101 and at least the beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404 and DRB1*0405. More preferably the alpha 1 domain and the alpha 2 domain is from DRA*0101 and the beta 1 domain and the beta 2 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404, DRB1*0101 and DRB1*0405. In mice collagen-induced arthritis (CIA) is associated with the mouse MHC II Aq allele. Thus, in one embodiment the MHC II molecule in the complex is derived from the mouse MHC II Aq allele.

The composition comprising the MHC II/CII peptide complexes according to the invention comprises a post-translationally modified peptide. The CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6) and AGFKGXQGPXG (SEQ ID NO: 7), AGFKXEQGPXG (SEQ ID NO: 8). In certain embodiments the CII peptide comprises the amino acid sequence of AGFKGEQGPKG (SEQ ID NO: 1), AGFKGEQGP$X_1$G (SEQ ID NO: 2), AGFKGE$X_2$GPKG (SEQ ID NO: 3), AGFKG$X_3$QGPKG (SEQ ID NO: 4), AGFK$X_4$EQGPKG (SEQ ID NO: 5), AGFKGE$X_2$GP$X_1$G (SEQ ID NO: 6) and AGFKG$X_3$QGP$X_1$G (SEQ ID NO: 7), AGFK$X_4$EQGP$X_1$G (SEQ ID NO: 8), wherein $X_1$ is any of the proteinogenic amino acids except K, preferably R, A, G or Q, more preferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L. Preferably $X_2$, $X_3$ or $X_4$ is not K, more preferably $X_1$, $X_2$, $X_3$ or $X_4$ is not K. In certain embodiments the CII peptide comprises the amino acid sequence of AGFKGEQGPKG (SEQ ID NO: 1) or AGFKGEQGP$X_1$G (SEQ ID NO: 2), preferably of AGFKGEQGPKGEP (SEQ ID NO: 10) or AGFKGEQGP$X_1$GEP (SEQ ID NO: 11), more preferably of GIAGFKGEQGPKGEP (SEQ ID NO: 13) or GIAGFKGEQGP$X_1$GEP (SEQ ID NO: 14). Preferably the CII peptide comprises the amino acid sequence of AGFKGEQGPKG (SEQ ID NO: 1) or AGFKGEQGPXG (SEQ ID NO: 2), preferably of AGFKGEQGPKGEP (SEQ ID NO: 10) or AGFKGEQGPXGEP (SEQ ID NO: 11), more preferably of GIAGFKGEQGPKGEP (SEQ ID NO: 13) or GIAGFKGEQGPXGEP (SEQ ID NO: 14). The CII peptide GIAGFKGEQGPKGEP (SEQ ID NO: 13) corresponds to amino acids 259-273 of the triple helical CII region. CII peptides suitable for binding into the binding pocket of MHC II are from 10 to 20 amino acids in length, preferably the CII peptide is from 11 to 15 amino acids in length, more preferably the CII peptide is from 13 to 15 amino acids in length. In one embodiment the CII peptide comprises the amino acid sequence AGFKGEQGPKG (SEQ ID NO: 1), more preferably AGFKGEQGPKGEP (SEQ ID NO: 10) and even more preferably of GIAGFKGEQGPKGEP (SEQ ID NO: 13). In one embodiment the second K (K270) may be mutated, preferably to R. Thus, also encompassed are embodiments, wherein the CII peptide comprises the amino acid sequence AGFKGEQGPXG (SEQ ID NO: 2), AGFKGEQGPXGEP (SEQ ID NO: 11) and GIAGFKGEQGPXGEP (SEQ ID NO: 14), wherein X may be any proteinogenic amino acid other than K, preferably X is R, A, G or Q, more preferably R). In one embodiment the CII peptide comprises the amino acid sequence AGFKGEQGPRG (SEQ ID NO: 9), AGFKGEQGPRGEP (SEQ ID NO: 12) and GIAGFKGEQGPRGEP (SEQ ID NO: 15).

The composition comprising the MHC II/CII peptide complexes according to the invention comprise MHC II/CII peptide complexes with a CII peptide, wherein preferably at least the first lysine residue of the CII peptide is hydroxylysine (Hyl) and/or is O-glycosylated hydroxylysine. The first lysine (K) residue of the CII peptide corresponds to the first K in GIAGFKSGEQGPKGEP (SEQ ID NO: 13) at position 264 of the amino acid sequence of the triple helical CII region. The optional second lysine (K) residue in the CII peptide corresponds to the second K in GIAGFKGEQGPKSGEP at position 270 of the amino acid sequence of the triple helical CII region. In a preferred embodiment the MHC II/CII peptide complexes according to the invention comprise a post-translationally modified CII peptide, wherein at least the first lysine residue is hydroxylysine and/or galactosyl-hydroxylysine. The term "galactosyl-hydroxylysine" may also be referred to as G-Hyl or Gal-Hyl and excludes a modification to glucosylgalactosyl-hydroxylysine.

The collagen specific post-translational galactosylation of the lysine residues in the CII peptide sequence according to the invention, particularly of the first lysine residue, i.e., lysine residue at position 264, is involved in T cell recognition via the TCR and the resulting pharmacological effects. The lysine residue in position 270 is located at the edge of the binding groove of the DR4 molecule and its galactosyl-hydroxylysine modification is considered to be less important for TCR recognition. Thus, the second or further lysine residue (corresponding to K 270) may be any of unmodified, hydroxylysine or galactosyl-hydroxylysine, preferably unmodified. It has been shown that the TCR of a T cell hybridoma recognizing the gal264 epitope is not affected by a K270R mutation. In a preferred embodiment the CII peptide comprises only the first lysine residue and any further optional K (such as the optional second K) is mutated, preferably mutated to R. Therefore CII peptides comprising the amino acid sequence AGFKGEQGPRG (SEQ ID NO: 9), preferably AGFKGEQGPRGEP (SEQ ID NO: 12) and more preferably GIAGFKGEQGPRGEP (SEQ ID NO: 15) are also encompassed by the present invention. Mutation of the second lysine has the advantage to reduce heterogeneity of the product and hence the percentage of correctly modified peptides is higher. Furthermore, galactosyl-hydroxylysine may be glucosylated to form glucosyl-galactosyl-hydroxylysine (Glc-Gal-Hyl, or GG-Hyl), which is likely to have a negative effect on TCR recognition due to the bulkiness of the disaccharide (Glc-Gal), particularly at position K270. Thus a K270 mutation, particularly K270R, further avoids interference with binding as no disaccharide modification can be attached at this position.

The collagen II peptide (CII peptide) is fused to the N-terminus of the MHC class II alpha chain or the MHC class II beta chain by a linker peptide, preferably to the N-terminus of the MHC class II beta chain. The term "linker peptide" refers to a polypeptide consisting of multiple amino acid residues. The linker peptide may be any peptide as long as it is long and flexible enough to allow the peptide to bind to the peptide binding pocket formed by the MHC II complex. An example of a suitable linker is a Gly-Ser linker. According to the invention the CII peptide, the linker peptide and at least one of the extracellular regions of the MHC 11 alpha chain and the MHC 11 beta chain are expressed as one polypeptide and encoded by one polynucleotide. The term "fused to" as used herein means "linked to" wherein the linking is via peptide bonds, optionally using a linker peptide, and therefore a fusion protein is generated. This feature structurally distinguishes the MHC II/CII peptide complex according to the present invention from prior art complexes. In previous complexes the MHC II protein is produced with a CLIP peptide as a surrogate peptide, which is linked to one of the MHC II chains via a linker peptide comprising a peptidase cleavage site, such as a thrombin cleavage site. Thus, following production the peptide is enzymatically cleaved off and the synthetically prepared galactosylated peptide (i.e., a CII peptide carrying gal-Hyl at position K264) is loaded in vitro onto the complex. Although this synthetic galactosylated peptide may be covalently linked to the MHC II molecule, this linkage is not via a linker peptide. While the MHC II/CII peptide complex used in the examples still contains an enzymatic cleavage site (thrombin cleavage site, FIG. 1) between the linker and the CII peptide, this is not necessary and is preferably removed from a therapeutic product. The linker peptide may improve stability of the product and prevent peptide loss. Thus, preferably the MHC II/CII peptide complex according to the invention does not contain an enzymatic cleavage site in the amino acid sequence between the CII peptide and extracellular region of the MHC II beta chain (or the MHC II alpha chain). Furthermore, for therapeutic purposes the MHC II/CII peptide complexes comprised in the composition do not comprise a (1) streptavidin-tag (such as SAWSHPQFEK; SEQ ID NO: 30) for purification, (2) a cleavage site (e.g., a TEV cleavage site) between the MHC II α/MHC II β chain and the heterodimerisation domain and/or (3) a recognition site for the *E. coli* biotin ligase (BirA) (e.g., an AviTag) as present in the exemplified complex shown in FIG. 1 and used in the Examples. These elements were shown to have no effect on in vitro and in vivo functionality of the complex (data not shown). Preferably the MHC II/CII complex comprises the His-tag (polyhistidine-tag) or a functionally equivalent tag at the C-terminal end of the polypeptide comprising the HLA-DR alpha chain and/or the HLA-DR beta chain. An exemplary minimal HLA-DR/CII peptide complex according to the present invention may be encoded by the amino acid sequence according to SEQ ID NO:18 and SEQ ID NO:19. The person skilled in the art would understand that the peptide sequence may vary as encompassed by the claims.

Preferably the compositions according to the invention comprise MHC II/CII peptide complexes containing a His-tag or a functionally equivalent tag at the C-terminal end of the polypeptide comprising the HLA-DR alpha chain and/or the HLA-DR beta chain. Functionally equivalent tags are e.g., chondroitin-binding peptides. Thus, the composition may comprise MHC II/CII peptide complexes comprising at least one chondroitin-binding peptide, preferably a chondroitin- and hyaluronic acid-(also referred to as hyaluronan) binding peptide. In one embodiment the MHC II/CII peptide complex comprises at least one C-terminal chondroitin-binding peptide. Chondroitin-binding peptides are known in the art and include without being limited thereto peptides having the amino acid sequences EKRIWFPYRRF (SEQ ID NO: 31), YKTNFRRYYRF (SEQ ID NO: 32) or VLIRHFRKRYY (SEQ ID NO: 33) (Butterfield K C et al., Biochemistry. 2010 Feb. 23; 49(7):1549-55). In one embodiment the chondroitin binding peptide comprises 5 to 20 amino acids, preferably 6 to 20 amino acids, more preferably 6 to 12 amino acids. To increase binding to hyaluronan a respective sequence containing the binding consensus motif is defined as follows: $B(X_7)B$, in which B is either R or K and $X_7$ contains no acidic residues and at least one basic amino acid (Yang Bet al., EMBO J. 1994 Jan. 15; 13(2): 286-96). As disclosed herein the MHC II/CII peptide complex can also bind to chondroitin sulfate via the his-tag. Thus, the chondroitin binding peptide may be a polyhistidine-tag, preferably a hexa histidine-tag, or any other amino acid sequences that increase binding affinity to chondroitin sulfate, such as. EKRIWFPYRRF (SEQ ID NO: 31), YKTNFRRYYRF (SEQ ID NO: 32) or VLIRHFRKRYY (SEQ ID NO: 33). Chondroitin and hyaluronic acid are both important components of cartilage.

In one embodiment the extracellular region of the MHC class II alpha chain comprising at least an alpha 1 domain and the extracellular region of the MHC class II beta chain comprising at least a beta 1 domain; and the collagen II peptide (CII peptide) fused to the N-terminus of the MHC class II alpha chain or the MHC class II beta chain by a linker peptide, preferably to the MHC class II beta chain; are expressed as a single fusion polypeptide (single chain heterodimer).

In an alternative embodiment the MHC II/CII peptide complex comprises a first polypeptide comprising the extracellular region of the MHC class II alpha chain comprising at least an alpha 1 domain; a second polypeptide comprising the extracellular region of the MHC class II beta chain comprising at least a beta 1 domain; and the collagen II peptide (CII peptide) fused to the N-terminus of the MHC class II alpha chain or the MHC class II beta chain by a linker peptide, preferably to the MHC class II beta chain. In one embodiment the MHC class II alpha chain is fused at its C-terminal end to a first functional domain of a leucine zipper heterodimerization motif and the MHC class II beta chain is fused at its C-terminal end to a second complementary functional domain of a leucine zipper heterodimerization motif. The first functional domain and the second complementary functional domain may be an acidic and a basic leucine zipper heterodimerization domain, preferably a jun-fos leucine zipper motif. In one embodiment the first and/or the second polypeptide comprises a chondroitin sulfate binding peptide, such as a polyhistidine tag, at the C-terminus of the functional domain of a leucine zipper heterodimerization motif.

The person skilled in the art will understand that the composition according to the invention comprises MHC II/CII peptide complexes in a heterogeneous mixture of MHC II/CII peptide complexes comprising different post-translational modifications of the CII peptide, particularly the first and optional second lysine residue of the CII peptide. The heterogeneous mixture may comprise MHC II/CII peptide complexes comprising K, Hyl, G-Hyl or GG-Hyl at the first lysine and independently K, Hyl, G-Hyl or GG-Hyl at the optional second lysine (wherein K=lysine, Hyl=hydroxylysine, G-Hyl=galactosylhydroxylysine, GG-Hyl=glucosylgalactosylhydroxylysine).

Thus, in one embodiment the composition further comprises MHC II/CII peptide complexes comprising the CII peptide, wherein the first lysine residue of the CII peptide is unmodified, hydroxylysine (Hyl) or glucosylgalactosyl-hydroxylysine (GG-Hyl), preferably unmodified or hydroxylysine (Hyl) and the optional second lysine residue of the CII peptide is independently unmodified, hydroxylysine (Hyl), galactosyl-hydroxylysine (G-Hyl) or glucosylgalactosyl-hydroxylysine (GG-Hyl), preferably unmodified, hydroxylysine (Hyl), galactosyl-hydroxylysine (G-Hyl). In one embodiment the composition does not comprise glucosylgalactosyl-hydroxylysine (GG-Hyl) modified MHC II/CII peptide complexes, e.g., MHC II/CII peptide complexes comprising an O-glycosylated CII peptide wherein the first and the optional second lysine residue are glucosylgalactosyl-hydroxylysine.

Preferably the composition comprises MHC II/CII peptide complexes comprising at least 5%, at least 10%, at least 20% or at least 30% of G-Hyl at the first lysine (K264) of the CII peptide of total MHC II/CII peptide complexes in the mixture or the composition. Further, the composition comprises MHC II/CII peptide complexes comprising preferably less than 50%, less than 40% or less than 30% unmodified CII peptides of total MHC II/CII peptide complexes in the mixture or the composition. Further, the composition comprises MHC II/CII peptides complexes comprising preferably less than 20%, less than 10%, less than 5% and more preferably less than 1% GG-Hyl in the CII peptide of total MHC II/CII peptide complexes in the mixture or the composition. Wherein the percentage refers to percent of CII peptide in the MHC II/CII peptide complexes of total CII peptides in the MHC II/CII peptide complexes. In a particular preferred embodiment said second lysine residue (K270) is mutated, for example mutated to arginine (K270R). In a further embodiment the (optional) second lysine is not post-translationally modified to glucosylgalactosyl-hydroxylysine (GG-Hyl) and is present as unmodified lysine, hydroxylysine or galactosyl hydroxylysine.

In a further aspect the present invention provides a recombinant MHC II/CII peptide complex, obtained or obtainable by the method of the present invention. Particularly encompasses is said recombinant MHC II/CII peptide complex comprising a post-translationally modified CII peptide, wherein the first lysine residue of the CII peptide is hydroxylysine (Hyl) or is O-glycosylated Hyl. Thus, in one embodiment the recombinant MHC II/CII peptide complex comprising an O-glycosylated CII peptide is obtained by the method of the invention.

In yet a further aspect the present invention provides a composition comprising the recombinant MHC II/CII peptide complex comprising a post-translationally modified CII peptide obtained by the method of the present invention.

Also envisages is the use of the composition according to the invention or the MHC II/CII peptide complex tetramer of the invention for detecting antigen-specific T cells, preferably in vitro.

The composition of the invention may be a pharmaceutical composition. Thus the present invention also discloses pharmaceutical compositions comprising the composition comprising recombinant MHC II/CII peptide complexes as described herein and pharmaceutically acceptable excipients. The composition or pharmaceutical composition may be administered by any route of administration, preferably subcutaneously (s.c.) or intravenously (i.v.). In one embodiment the composition or pharmaceutical composition is administered using an osmotic pump implanted subcutaneously. The composition or pharmaceutical composition comprising the recombinant MHC II/CII peptide complexes according to the invention may be lyophilized or in an aqueous solution. Pharmaceutically acceptable excipients may include carriers as well as stabilizers.

In yet another aspect the invention relates to a composition comprising the recombinant MHC II/CII peptide complex according to the invention or to the recombinant MHC II CII peptide complex produced by the method according to the invention for use in treating chronic inflammatory disease. Preferably the composition is a pharmaceutical composition further comprising pharmaceutically acceptable excipients. In one embodiment the composition comprising the recombinant MHC II/CII peptide complex according to the invention or to the recombinant MHC II CII peptide complex produced by the method according to the invention is for use in treating chronic inflammatory disease in a human subject, particularly arthritis or other chronic inflammatory joint disease. In one embodiment the composition is for use in treating chronic inflammatory disease selected from the group consisting of rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme disease, Meniere diseases, autoimmune inner ear disease (AIED), or Still's disease.

The chronic inflammatory disease may be arthritis, preferably selected from the group consisting of rheumatoid arthritis, osteoarthritis, psoriatic arthritis, ankyloses spondylitis, juvenile idiopathic arthritis or Still's disease, more preferably rheumatoid arthritis, osteoarthritis, psoriatic arthritis, more preferably rheumatoid arthritis. In particular embodiments the composition according to the invention is for first line treatment of rheumatoid arthritis, for treatment in subjects inadequately responding to methotrexate and/or conventional synthetic (small molecule) disease modifying antirheumatic drugs (DMARDs), for treatment in subjects inadequately responding to biologic DMARDs (e.g., anti-TNF, anti-CTLA4 (abatacept) anti-IL-6, anti-CD20 (rituximab) antibodies), for treatment in subjects inadequately responding to targeted synthetic DMARDs (e.g., JAK-inhibitors). In alternative embodiments the composition according to the invention is for prophylactic treatment in patients at high risk to develop rheumatoid arthritis, such as anti-ccp antibody positive smokers with new onset of musculoskeletal symptoms.

Preferably the composition is to be administered subcutaneously or intravenously, more preferably subcutaneously. The composition may be administered at single doses of about 10 μg to about 250 μg, preferably 20 to 200 μg, more preferably 50 μg to 100 μg. In one embodiment, treatment comprises a loading and a maintenance phase. The loading phase may comprise 3 to 10, preferably 6 sequential applications on consecutive days. Maintenance doses may be administered weekly or every 3 to 14 days, preferably weekly, biweekly, monthly, every two months or at even higher intervals.

Tetramers Comprising Recombinant MHC II/CII Peptide Complex

In yet another aspect the invention provides a MHC II/CII peptide complex tetramer comprising the recombinant MHC II/CII peptide complex(es) of the composition according to the invention or the recombinant MHC II/CII peptide complex comprising a post-translationally modified CII peptide obtained by the method according to the invention. Preferably the CII peptide comprises a post-translational modification at a lysine residue, preferably at the first lysine residue of the CII peptide. In one embodiment the first lysine residue of the CII peptide is Hyl or is O-glycosylated Hyl. In one embodiment the tetramer comprises a multimerization molecule, preferably streptavidin or avidin, binding the recombinant MHC II/CII peptide complexes. In a preferred embodiment the mulitimerisation molecule is streptavidin. Each of the recombinant MHC II/CII peptide complexes may contain at least one covalently bound, N-terminal biotin. Biotinylation, the process of covalently attaching biotin to a protein, is preferably site specific and may be via chemical linkage or via enzymatic linkage. Preferably, the recombinant MHC II/CII peptide complexes contain a recognition site for a biotin ligase, such as the *E. coli* biotin ligase (BirA). The recognition site for BirA is a 15 amino acid peptide termed AviTag or Acceptor Peptide (e.g., an AviTag). Enzymatic biotinylation can be carried out in vitro or in vivo.

The multimerization molecule, such as streptavidin, may be conjugated to a label, preferably a fluorochrome, in order to allow detection of the tetramers, particularly the bound tetramers. Labels may be any label known in the art, such as horse radish peroxidase to be detected by enzymatic chemiluminescence (ECL) or luciferase. Other examples are fluorochromes such as PE, APC, rhodamine (TRITC), FITC etc.

The tetramers are produced by a method for preparing a MHC II/CII peptide complex tetramer comprising (a) providing the composition according to the invention or the recombinant MHC II/CII peptide complex comprising an O-glycosylated CII peptide according to the invention, wherein the MHC II/CII peptide complex comprises at least one N-terminal biotinylation, (b) contacting the composition with a multimerization molecule, preferably streptavidin, and optionally isolating tetramers comprising four MHC II/CII peptide complexes bound to a streptavidin.

The tetramers according to the invention may be used for detecting antigen-specific T cells and hence for detecting arthritis, particularly rheumatoid arthritis. Thus, in one aspect the invention relates to a method for detecting and/or quantifying T cells specific for a given antigen, wherein the method comprises (a) providing the MHC II/CII peptide complex tetramer according to the invention, wherein the multimerization molecule is conjugated to a label (b) contacting the MHC II/CII peptide complex tetramer with a sample of a subject, preferably a sample containing peripheral blood cells of said subject, and (c) detecting the label of the MHC II/CII peptide complex tetramer bound T cells. Preferably the method is an in vitro detection method. Preferably the label is a fluorochrome. The labelled MHC II/CII peptide complex tetramer bound to T cells may be detected by any suitable methods known to the art, such as flow cytometry. Preferably the method is an in vitro method. In one embodiment the method is a method for diagnosing a patient with arthritis or rheumatoid arthritis comprising (a) providing the MHC II/CII peptide complex tetramer according to the invention, wherein the multimerization molecule is conjugated to a label (b) contacting the MHC II/CII peptide complex tetramer with a sample of a subject, preferably a sample containing peripheral blood cells of said subject, and (c) detecting the label of the MHC II/CII peptide complex tetramer bound to T cells. If labelled MHC II/CII peptide complex tetramer bound to T cells are detected the patient is likely to have or to be at risk of developing arthritis, particularly rheumatoid arthritis.

In view of the above, it will be appreciated that the invention also encompasses the following items:

1. A composition comprising recombinant MHC II/CII peptide complexes comprising
   (a) an extracellular region of an MHC class II alpha chain comprising at least an alpha 1 domain;
   (b) an extracellular region of an MHC class II beta chain comprising at least a beta 1 domain; and
   (c) a collagen II peptide (CII peptide) fused to the N-terminus of the MHC class II alpha chain or the MHC class II beta chain by a linker peptide, preferably to the MHC class II beta chain; wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8),
   wherein the MHC II/CII peptide complexes comprise a post-translationally modified CII peptide, preferably wherein the first lysine residue of the CII peptide is hydroxylysine (Hyl) or is O-glycosylated Hyl.
2. The composition of item 1, wherein
   (a) the extracellular region of the MHC class II alpha chain comprises an alpha 1 and an alpha 2 domain; and/or
   (b) the extracellular region of the MHC class II beta chain comprises a beta 1 and a beta 2 domain.
3. The composition of item 1 or 2, wherein the first lysine residue is galactosyl-hydroxylysine.
4. The composition of any one of items 1 to 3, wherein the CII peptide is fused to the N-terminus of the beta 1 domain by a linker peptide.
5. The composition of any one of items 1 to 4, wherein at least the alpha 1 domain is from DRA*0101 and at least the beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401.
6. The composition of any one of items 1 to 5, wherein the CII peptide comprises the amino acid sequence of AGFKGEQGPKG, preferably of AGFKGEQGPKGEP, more preferably of GIAGFKGEQGPKGEP.
7. The composition of any one of items 1 to 6, wherein the CII peptide comprises only the first lysine residue and any further K is mutated, preferably mutated to R, A, G or Q, more preferably to R.
8. The composition of any one of items 1 to 7, wherein
   (a) the extracellular region of the MHC class II alpha chain comprising at least an alpha 1 domain;
   (b) the extracellular region of the MHC class II beta chain comprising at least a beta 1 domain; and
   (c) the collagen II peptide (CII peptide) fused to the N-terminus ofthe MHC class II alpha chain or the MHC class II beta chain by a linker peptide;
   are expressed as a single fusion polypeptide.
9. The composition of any one of items 1 to 7 comprising
   (a) a first polypeptide comprising the extracellular region of the MHC class 11 alpha chain comprising at least an alpha 1 domain;
   (b) a second polypeptide comprising the extracellular region of the MHC class II beta chain comprising at least a beta 1 domain; and
   (c) the collagen II peptide (CII peptide) fused to the N-terminus of the MHC class II alpha chain or the MHC class II beta chain by a linker peptide.
10. The composition of item 9, wherein the MHC class II alpha chain is fused at its C-terminal end to a first functional domain of a leucine zipper heterodimerisation motif and the MHC class II beta chain is fused at its C-terminal end to a second complementary functional domain of a leucine zipper heterodimerisation motif.
11. The composition of item 10, wherein the first functional domain and the second complementary functional domain are
   (a) an acidic and a basic leucine zipper heterodimerisation domain; and/or
   (b) a jun-fos leucine zipper motif.
12. A composition of any one of items 1 to 11, further comprising MHC II/CII peptide complexes comprising the CII peptide, wherein the first lysine residue of the CII peptide is unmodified.
13. A method for producing a MHC II/CII peptide complex comprising a post translationally modified (e.g. O-glycosylated) CII peptide comprising
   (a) transfecting a mammalian cell with
      (i) a polynucleotide encoding an extracellular region of the MHC II alpha chain comprising at least an alpha 1 domain;
      (ii) a polynucleotide encoding an extracellular region of the MHC II beta chain comprising at least a beta 1 domain; and
      (iii) a polynucleotide encoding a collagen II peptide (CII peptide) fused to the N-terminus of the MHC class II alpha chain or the MHC class II beta chain by a linker peptide, preferably to the MHC class II beta chain, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8);
(b) cultivating the mammalian cells under conditions suitable to produce the MHC II/CII peptide complex, and
(c) harvesting a cell supernatant and optionally cells comprising the MHC II/CII peptide complex comprising a post-translationally modified CII peptide, preferably wherein the first lysine residue of the CII peptide is hydroxylysine (Hyl) or is O-glycosylated Hyl.

14. The method of item 13 further comprising a step of analysing the post-translational modification, preferably the glycosylation profile, of the CII peptide of the MHC II/CII peptide complex.

15. The method of items 13 or 14, wherein the first lysine residue is galactosyl-hydroxylysine.

16. The method of any one of items 13 to 15, wherein the mammalian cell
(a) comprises enzymes to post-translationally modify lysine residues in collagen, comprising hydroxylating lysine to hydroxylysine (Hyl) and galactosylating Hyl to galactosylhydroxylysine
(Gal-Hyl); and/or
(b) comprises a lysylhydroxylase and a collagen galactosyltransferase, preferably lysylhydroxylase 1 (LH1) and/or lysylhydroxylase 2 (LH2) and collagen galactosyltransferase GLT25D1 and/or GLT25D2, preferably GLT25D1.

17. The method of item 16, wherein the cell is
(a) a kidney cell, a fibroblast cell or an osteoblast cell, preferably a kidney cell, more preferably a HEK 293 cell line; or
(b) a genetically engineered cell recombinantly expressing a lysylhydroxylase and a collagen galactosyltransferase, preferably lysylhydroxylase 1 (LH1) and/or lysylhydroxylase 2 (LH2) and collagen galactosyltransferase GLT25D1 and/or GLT25D2.

18. The method of any one of items 13 to 17, wherein the mammalian cell
(a) lacks galactosylhydroxylysyl glucosyltransferase activity;
(b) lacks the multifunctional enzyme LH3; or
(c) comprises a mutant LH3 enzyme lacking galactosylhydroxylysyl glucosyltransferase activity.

19. The method of item 18, wherein the mammalian cell is genetically engineered to have reduced or no galactosylhydroxylysyl glucosyltransferase activity, preferably wherein
(a) the PLOD3 gene encoding for LH3 is mutated or deleted;
(b) the LH3 enzyme is a mutated LH3 enzyme lacking galactosylhydrosylysyl glucosyltransferase activity; or
(c) LH3 expression is suppressed by RNA interference.

20. The method of any one of items 13 to 16, further comprising adding carminic acid during cultivating the mammalian cells according to step (b).

21. The method of any one of items 13 to 20, wherein
(a) the extracellular region of the MHC class II alpha chain comprising an alpha 1 and an alpha 2 domain; and/or
(b) the extracellular region of the MHC class II beta chain comprising a beta 1 and a beta 2 domain.

22. The method of any one of items 13 to 21, wherein the CII peptide is fused to the N-terminus of the beta 1 domain.

23. The method of any one of items 13 to 22, wherein at least the alpha 1 domain is from DRA*0101 and at least the beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401.

24. The method of any one of items 13 to 23, wherein the CII peptide comprises the amino acid sequence of AGFKGEQGPKG (SEQ ID NO: 1), preferably of AGFKGEQGPKGEP (SEQ ID NO: 10), more preferably of GIAGFKGEQGPKGEP (SEQ ID NO: 13).

25. The method of any one of items 13 to 24, wherein the CII peptide comprises only the first lysine residue and any further K is mutated, preferably mutated to R, A, G or Q, more preferably to R.

26. The method of any one of items 13 to 25, wherein
(a) the extracellular region of the MHC class 11 alpha chain comprising at least an alpha 1 domain;
(b) the extracellular region of the MHC class II beta chain comprising at least a beta 1 domain; and
(c) the collagen II peptide (CII peptide) fused to the N-terminus of the MHC class II alpha chain or the MHC class II beta chain by a linker peptide;
are encoded by single polynucleotide to express a single fusion polypeptide.

27. The method of any one of items 13 to 25 comprising
(a) a first polynucleotide encoding the extracellular region of the MHC class II alpha chain comprising at least an alpha 1 domain;
(b) a second polynucleotide encoding the extracellular region of the MHC class 11 beta chain comprising at least a beta 1 domain; and
(c) a polynucleotide encoding the collagen II peptide (CII peptide) fused to the N-terminus of the MHC class II alpha chain or the MHC class II beta chain by a linker peptide.

28. The method of item 27, wherein the MHC class II alpha chain is fused at its C-terminal end to a first functional domain of a leucine zipper heterodimerisation motif and the MHC class II beta chain is fused at its C-terminal end to a second complementary functional domain of a leucine zipper heterodimerisation motif.

29. The method of item 28, wherein the first functional domain and the second complementary functional domain are
(a) an acidic and a basic leucine zipper heterodimerisation domain; and/or
(b) ajun-fos leucine zipper motif.

30. The method of any one of items 13 to 29, wherein the harvested cell supernatant and optionally harvested cells further comprises MHC II/CII peptide complexes comprising the CII peptide, wherein the first lysine residue of the CII peptide is unmodified.

31. A recombinant MHC II/CII peptide complex comprising a post-translationally modified CII peptide obtained by the method of any one of items 13 to 30, preferably wherein the first lysine residue of the CII peptide is hydroxylysine (Hyl) or is O-glycosylated Hyl.

32. A composition comprising the recombinant MHC II/CII peptide complex comprising a post-translationally modified CII peptide obtained by the method of any one of items 13 to 30, preferably wherein the first lysine residue of the CII peptide is hydroxylysine (Hyl) or is 0-glycosylated Hyl.

33. The composition of any one of items 1 to 12 and 32 for use in treating chronic inflammatory disease.
34. The recombinant MHC II/CII peptide complex according to item 31 for use in treating chronic inflammatory disease.
35. The composition for use according to item 33 or the recombinant MHC II/CII peptide complex for use according to item 34, wherein the chronic inflammatory disease is rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme disease, Meniere diseases, autoimmune inner ear disease (AIED), or Still's disease.
36. A MHC II/CII peptide complex tetramer comprising the recombinant MHC II/CII peptide complex(es) of the composition according to any one of items 1 to 12 and 32 or the recombinant MHC II/CII peptide complex comprising a post-translationally modified CII peptide according to item 31.
37. The MHC II/CII peptide complex tetramer according to item 36, wherein the tetramer comprises a multimerisation molecule, preferably streptavidin, binding the recombinant MHC II/CII peptide complexes.
38. The MHC II/CII peptide complex tetramer according to item 37, wherein each of the recombinant MHC II/CII peptide complexes contains at least one covalently bound, N-terminal biotin.
39. The MHC II/CII peptide complex tetramer according to items 37 to 38, wherein the multimerisation molecule is conjugated to a label, preferably a fluorochrome
40. A method for preparing a MHC II/CII peptide complex tetramer comprising
    (a) providing the composition according to items any one of items 1 to 12 and 32 or the recombinant MHC II/CII peptide complex comprising the post-translationally modified CII peptide of item 31, wherein the MHC II/CII peptide complex comprises at least one N-terminal biotinylation,
    (b) contacting the composition with a multimerisation molecule, preferably streptavidin, and
    (c) optionally isolating tetramers comprising four MHC II/CII peptide complexes bound to a streptavidin.
41. The method of item 40 wherein the multimerisation molecule is conjugated to a label, preferably a fluorochrome.
42. An in vitro method for detecting and/or quantifying T cells specific for a given antigen, wherein the method comprises
    (a) providing the MHC II/CII peptide complex tetramer according to item 39,
    (b) contacting the MHC II/CII peptide complex tetramer with a sample of a subject, preferably a sample containing peripheral blood cells of said subject, and
    (c) detecting the label of the MHC II/CII peptide complex tetramer bound to T cells.
43. The in vitro method of item 42, wherein the label is a fluorochrome and the MHC II/CII peptide complex tetramer bound T cells is detected by flow cytometry.
44. Use of the composition according to items 1 to 12 or the MHC II/CII peptide complex tetramer of items 36 to 39 for detecting antigen-specific T cells in vitro.

EXAMPLES

Test Substances and Formulations

Aq/galCII or DR4/galCII (loaded with synthetic Gal-peptide: GIAGFK(Gal-Hyl)GEQGPKGEP; SEQ ID NO: 36) and Aq/nCII or DR4/nCII (loaded with non-modified peptide: GIAGFKGEQGPKGEP; SEQ ID NO: 13): Aq-mCLIPmt protein was expressed in HEK293 cell line (Expi293F cells, Gibco, Cat. No.

Figure 4:
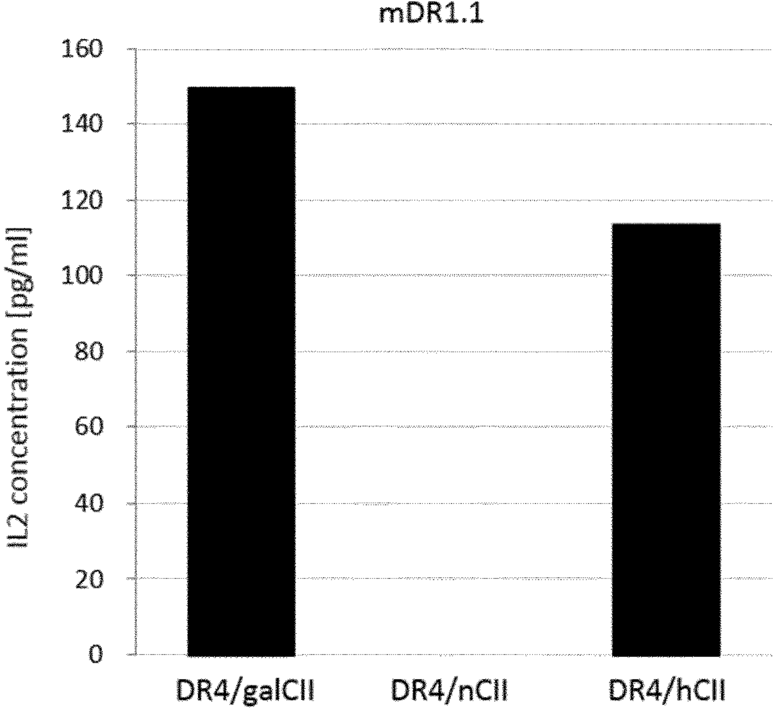
FIG. 4: Activation of glycosylation restrictive human T cell hybridoma. Human T cell hybridoma get activated upon stimulation with the human MHC II/CII peptide complex (DR4/hCII) in an antigen-specific manner. Recognition of human T cell hybridoma mDR1.1 and 3H8 is dependent on the glycosylation profile of the CII peptide. A) The T cell hybridoma clone mDR1.1 gets activated by galactosylated K264 presented by HLA-DR4 B) whereas the T cell hybridoma clone 3H8 gets activated by the non-modified CII epitope presented by HLA-DR4. Reactivity of the two different T cell hybridoma clones were compared by using human MHC II/CII peptide complexes loaded with synthetic galactosylated or non-modified CII peptide (DR4/galCII and DR4/nCII, respectively) and with naturally glycosylated MHC II/CII peptide complex (DR4/hCII). Secretion of IL-2 was measured by ELISA.
Figure 4:
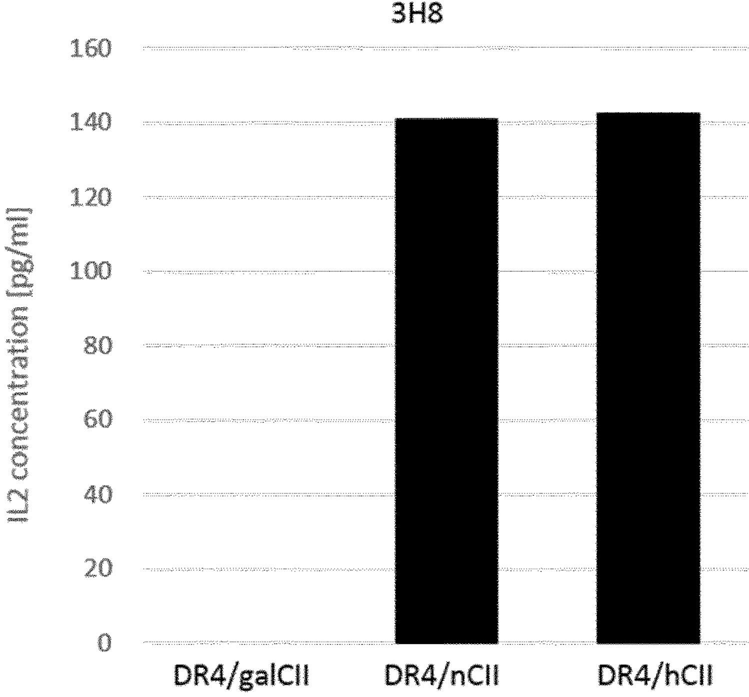

A14527) or CHO cells (FIG. 4) by transient transfection, purified using a combination of immobilized metal ion affinity chromatography (IMAC) using the His-tag and size exclusion chromatography (SEC). Then, the covalently bound pre-peptide was replaced by thrombin cleavage and the addition of excess Gal-peptide or non-modified peptide. Finally, SEC was performed to remove cleaved pre-peptide and excess of Gal-peptide or non-modified peptide. Gal-peptide: GIAGFK(Gal-Hyl)GEQGPKGEP (SEQ ID NO: 36) were synthesized, purified, and characterized, as described in Diogo, D. et al., Curr Opin Rheumatol. 2014; 26: 85-92; Gregersen P K et al., Arthritis Rheum. 1987; 30:1205-1213; Duke O et al., Clin Exp Immunol. 1982; 49:22-30.

Naturally glycosylated mouse Aq/rCII and human DR4/hCII: Naturally glycosylated mouse Aq/rCII and human DR4/hCII protein was expressed in HEK293 cell line (Expi293F cells, Gibco, Cat. No. A14527) by transient transfection and purified using a combination of immobilized metal ion affinity chromatography (IMAC) using the His-tag and size exclusion chromatography (SEC). For in vivo experiments, MHC II-peptide complexes were diluted to desired concentrations in sterile PBS (Gibco), filtered using a DynaGard 0.2 μm syringe tip filter and 100 μl protein solution was filled into LZET micro-osmotic pumps (DURECT corporation, model 1007D, 0.5 μl/h, 7 days) using sterile techniques. The pumps were handled with surgical gloves. To ensure immediate pumping of the substance the prefilled pumps were placed in PBS overnight at 4° C. before implantation.

More specifically cDNAs encoding the two chains of the complex as depicted in FIG. 1 were synthesized at Eurofins with Kpnl and Xhol restriction sites at the 5' and 3' ends. The synthesized cDNAs were digested using restriction enzymes Kpnl and Xhol (FastDigest™, ThermoFisher Scientific). The digested DNA fragments were cloned separately into mammalian expression vector pCEP4 (Life technologies) following digestion with the same restriction enzymes. After sequence verification, the two recombinant plasmids encoding the two chains of the complex were co-transfected into Expi393F™ cells with FectoPRO™ DNA transfection reagent (Polyplus transfection). The supernatants were harvested 6 days post-transfection. The recombinant protein was first captured using a 5 ml HisTrap Excel (GE Healthcare Life Sciences) affinity column followed by size-exclusion chromatography on Superdex 200 pg (GE Healthcare life Sciences). The recombinant protein was purified as a single peak and was concentrated, diafiltrated into biotinylation buffer (20 mM Tris-HCl, 50 mM NaCl, pH 8.0) using an Amicon centrifuge device with MWCO of 10 kDa. Biotinylation using biotin-protein ligase was performed according to the manufacturer's instructions (Avidity), and the reaction was carried out at 30° C. for 2 h. Free biotin were removed by size-exclusion chromatography on a Superdex 200 pg column.

Animals

Male QB mice (B10.Q×BALB/c, n=9) F1, 12-16 week of age, were used in the experiments. The founders of the B10.Q mice were originally provided by J. Klein (Tubingen, Germany), and BALB/c mice were purchased from The Jackson Laboratory. All mice were bred and housed at the animal facility of Medical Inflammation Research (Karolinska Institutet). All animals used were fed a standard rodent chow and given water ad libitum. Different experimental groups were housed together in order to minimize experimental bias. The local ethics committee approved all animal experiments (Stockholms Norra Djurforsoksetiska Namnd, Stockholm, Sweden). All in vivo arthritis experiments were covered by the ethical numbers N213/14 and N35/16. Anesthesia of animals was accomplished by isoflurane inhalation, whereas sacrifice was performed with CO2.

Induction and Clinical Evaluation of Arthritis

Rat type II collagen (rCII) was prepared from Swarm chondrosarcoma (Swarm rat chondrosarcoma, SRC), by limited pepsin digestion, and further purification, as described in Chavele K M and Ehrenstein M R, FEBS Lett. 2011; 585:3603-10. Prepared rCII was stored at 4° C. until used. To induce collagen-induced arthritis (CIA), each mouse was injected with 100 μg of rCII emulsified 1:1 in CFA (Difeo) at the base of the tail in a total volume of 100 μl. Thirty-five days later, the mice were given a booster injection of 50 μg of rat CII emulsified 1:1 in IFA (Difeo) in a total volume of 50 μl. Development of clinical arthritis was followed through visual scoring of the animals based on the number of inflamed joints in each paw, starting 2 weeks post-immunization and continuing until the end of the experiment. An extended scoring protocol as described in Klareskog L et al., Annu Rev Immunol. 2008; 26: 651-75 ranging from 1 to 15 for each paw with a maximum score of 60 per mouse was used. The mice were examined two to four times per week for 90 days following immunization.

Treatment Protocol

The ALZET micro-osmotic pumps diffusing either different amounts of naturally-glycosylated Aq/rCII (n=9) or PBS (control group, n=9) were implanted subcutaneously in QB mice on day 7 post-immunization. Sterile techniques were used during the surgical implantation procedure. For subcutaneous placement, a small incision was made into the skin between the scapulae, a small pocket was formed and the pumps were inserted into the pocket with the flow moderator pointing away from the incision. The skin incisions were closed using wound clips.

A single s.c. injection of 100 μg in mice was nearly equally effective on the treatment of clinical arthritis as the s.c. pump infusion of 15 μg/day for 7 consecutive days. However, the prolonged treatment seemed to be more effective on the induction of regulatory TR1 cells as evidence by FACS analysis of lymph node T cells in the treated mice.

DTH

Q B mice pre-immunized with rat CII/CFA (rCII) were intradermally injected with 10 μg of rCII dissolved in phosphate buffered saline (PBS) into the left ear at day 8 post-immunization. For control the right ears were injected with solvent and the ear swellings measured 24 h later by an investigator blinded for the treatment of the animals using a caliper. Treatment was performed via a 24 h application of 100 μg of Aq/peptide complexes using osmotic pumps implanted at day 4 post immunization with rCII. Groups: Aq/mCLIPmt (n=6), Aq/galCII with (His, n=5) and without His-tag (w/o His, n=5).

T Cell Hybridoma Assay

MHC II/peptide complexes were diluted in sterile PBS and coated onto plates by incubation at 4° C. for overnight or added directly in soluble form to T cell hybridomas. The MHC II/peptide complex-coated plates were then washed twice with sterile PBS to remove unbound complexes, and $5\times10^4$ T-hybridoma cells in 200 μl DMEM supplemented with 5% FCS, 100 IU/ml penicillin, and 100 μg/ml streptomycin were added per well. T cell hybridoma 3H8 and mDR1.1 specific for GalOK264 and for nonmodified CII259-273 (K264), respectively, have been used. After 24 h, IL-2 or IL-10 (in some experiments) was measured in the culture supernatants by sandwich ELISA (Biolegend). Mouse rII-2 or rI-10 respectively served as a positive control and standard.

Stimulation experiments using T-hybridoma cells were performed under different conditions in microtiter wells: 1) pre-coated with recombinant DR4/CII-peptide complexes, 2) coated with hyaluronan (Sigma Aldrich (#H7630)) or chondroitin sulfate (Sigma Aldrich (#C9819)) to which the DR4/CII-peptide complexes were subsequently added in fluid phase. This design was chosen to study the impact of the potential interaction of both components on T cell activation by the DR4/CII-peptide complex and mimics the interplay of the DR4/CII-peptide complexes with connective tissue components physiologically expressed in the extracellular matrix (ECM) in the tissues and the draining lymphatic system, or 3) with a blocked surface to which the solute ECM components hyaluronan, chondroitin sulfate or heparin sulfate as well as the DR4/CII-peptide complexes were added in order to study their impact on the T-hybridoma cells as a model for the modulation of T cell function in body fluids of diseased tissues compartments e.g. joint effusions or the lymph fluid.

Detection of Antigen Specific T Cells by MHC II Tetramer Staining

The MHC II/peptide tetramer complexes were freshly prepared by adding PE-labeled streptavidin and APC-labeled streptavidin (Biolegend) to the recombinant protein at a molar ratio of 1:4, and incubating at +4° C. for 1 h. To identify peptide-specific T lymphocytes, cells were incubated with the DR4/peptide tetramer complexes (20 μg/ml) at +37° C. for 1 h in the presence of 50 nM Dasatinib, a small-molecule protein tyrosine kinase inhibitor, following staining for cell surface markers. Viability staining solution (Zombie NIR; Biolegend) was added just before acquisition to exclude dead cells from the analysis. The samples were acquired by using an LSR Fortessa flow cytometer using FacsDiVa software (BD Biosciences), and the data were analyzed with FlowJo Software (v10, FlowJo LLC).

Activation of Human T Cells Upon CII Peptide Stimulation

PBMCs were thawed and rested overnight in TexMACS (Biolegend) at 1.5×106 cell/well. Cells were stimulated with the respective peptide variants GIAGFKGEQGPKGEP (SEQ ID NO: 13) and GIAGFK(Gal-Hyl)GEQGPKGEP) at a concentration of 50 μg/ml for 7 hours together with anti-CD28 at 1 μg/ml (BioLegend). For positive control and determination of CD154 assay sensitivity, staphylococcal enterotoxin B (SEB) was added to a separate culture at 1 μg/ml (Sigma-Aldrich). Following stimulation, cells were treated with LIVE/DEAD discrimination marker (Biolegend) and then stained for surface expression of CD3 and CD4, for positive gating and for CD19 for exclusion of B cells. Background levels were determined by unstimulated cells (treated with anti-CD28) and further subtracted from the CII-stimulated cultures. The samples were acquired by using an LSR Fortessa flow cytometer using FacsDiVa software (BD Biosciences), and the data were analyzed with FlowJo Software (v10, FlowJo LLC).

In Vitro Stimulation/Differentiation of T Cells from the Peripheral Blood of HLA-DRB1*0401-Positive RA Patients In vitro assays were performed to analyze the induction/differentiation of regulatory T cell functions e.g. the upregulation of the Tr phenotype associated cytokine IL-10 upon stimulation with DR4/CII-monomers for a prolonged incubation period of several days. Accordingly, PBMCs were isolated by dense gradient centrifugation and $1.2\times10^6$ cells/ml cells in TexMACS (Miltenyi Biotec, Cat #130-097-196) were stimulated with 1 μg/ml anti-CD3 (Biolegend, Cat #317304) and 100 ng/ml IL-27 (Peprotech, Cat #200-38B) (positive control, Tr1), 3.6 μg/ml DR4/nCII, 3.6 μg/ml DR4/galCII, 3.6 μg/ml DR4/hCII or left without stimulation (negative control, w/o) for 8 days. Stimulation was done in duplicates. At day 8 the culture supernatants were collected and analyzed for released cytokines using a custom made panel for detection of human cytokines in a multiplex bead-based LEGENDplex™ assay following the manufacture's protocol.

Results:

Example 1: Production of Functionally Active Aq/rCII in HEK 293 Cells

It has been verified in previous experiments that two intravenous injections with Aq molecules loaded with synthetic galactosylated CII259-273 peptides can protect mice from development of arthritis. However, the synthesis of the galactosylated CI259-273 is both time- and cost consuming. In addition, the loading of the synthetic peptide to the recombinant MHC class II molecule is neither trivial nor cost efficient. Accordingly, it would be a significant advantage to establish a biosynthetic process allowing for the single step production of the MHC II molecule containing the covalently bound CII259-273 peptide (FIG. 1) fused to one of the MHC II chains in a host cell that ensures a proper posttranslational modification of the lysine side chain at position 264 in the CII-peptide by hydroxylation and subsequent galactosylation in situ. The posttranslational collagen peptide modifications however depend on the presence of the respective enzyme activities, i.e., lysyl hydroxylase activity and collagen beta galactosyltransferase activity. For example, *E. coli*-produced proteins do not normally display such modifications and while some insect cells have the capacity to hydroxylate lysine residues, they do not produce CII-peptides containing O-linked glycosylation of hydroxylysine. Moreover, it was unknown, whether a host cell providing the required enzyme activities would indeed be capable of providing the required modifications at the selective amino acid position of the CII-peptide within the frame of the non-collagenous MHC II protein sequence.

In the following it is shown for the first time that Aq/rCII (259-273) complexes can be expressed in HEK293 cells and that the purified complexes comprise covalently linked CII peptides (CII259-273) wherein the lysine at position 264 is posttranslationally modified. We analysed type of modifications of the lysine side chains in the CII peptide and whether the purified in situ galactosylated Aq/rCII(259-273) complex are protective in a CIA mouse model in a similar manner as observed for recombinant Aq molecules loaded with galactosylated CII259-273 peptides. To test the therapeutic potential of HEK293-produced Aq/rCII(259-273) complexes we used osmotic pumps that have been implanted subcutaneously one week after immunization. Osmotic pumps are advantageous over intravenous injections, because Aq/rCI1(259-273) complexes remains in the circulation at constant level and are available for tolerance induction in vivo over a longer period of time. When comparing three different types of pumps that releases their content over 24 hours, 7 days or 6 weeks, it was found that all three pumps mediate protection from arthritis when containing with Aq-molecules loaded with synthetic galactosylated CII-peptides (data not shown). However, using the pump with a sustained release for 7 days pumps was found to mediate protection more strongly associated with development of CII-specific T cells with regulatory capacity, compare to 24 hour pumps (data not shown). Without being bound by theory, a slow release rate at a low dose may result in the development of regulatory T cells whereas a faster release of a higher dose may result in depletion of pathogenic T cells. However, the observed difference could also be explained by the prolonged exposure, which increases the likelihood of CII-specific T cells—which would occur at low frequency—to interact with the Aq/rCII(259-273) complex before it is eliminated from the circulation. The experiments described below were done using osmotic pumps that release their content over 7 days.

Figure 2:
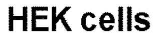
FIG. 2: IL-2 (FU) secretion of Aq-restricted T cell hybridoma clones in response to Aq/rCII(259-273) complexes (recombinant, in situ glycosylated Aq/rCII) produced in HEK293 cells (top) S2 insect cells (middle) and anti-CD3 antibody stimulation (bottom). The used mouse T cell hybridoma clones have the following specificities: HCQ3 (CII, Gal-HK264), HCQ.4 (CII, not modified and HK264), HCQ.11 (Glc-Gal-HK264), HM1R.2 (CII, Gal-HK264 and Gal-HK264+270), HP3 (Aq-restricted, pepsin-peptide), wherein K is the abbreviation for lysine and HK is the abbreviation for hydroxylysine.
Figure 2:
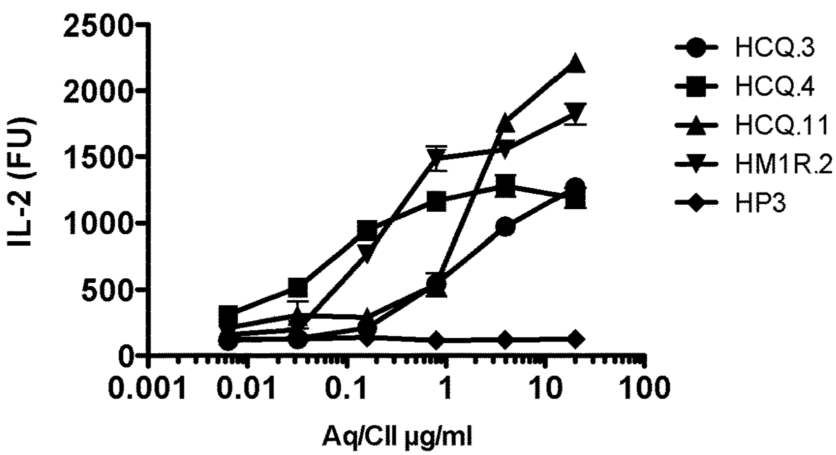
Figure 2:
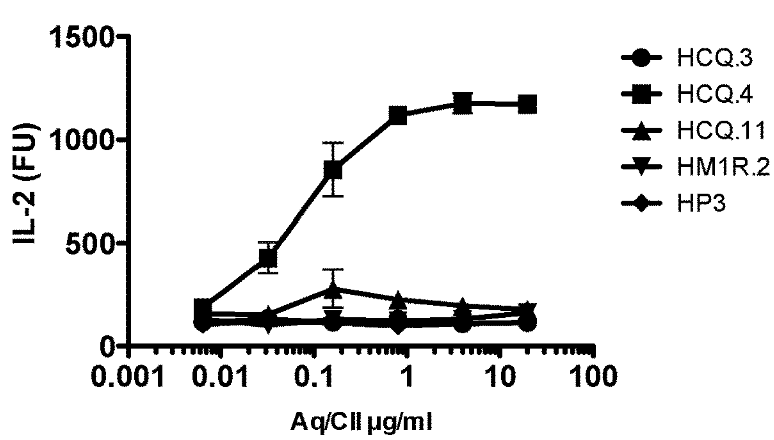
Figure 2:
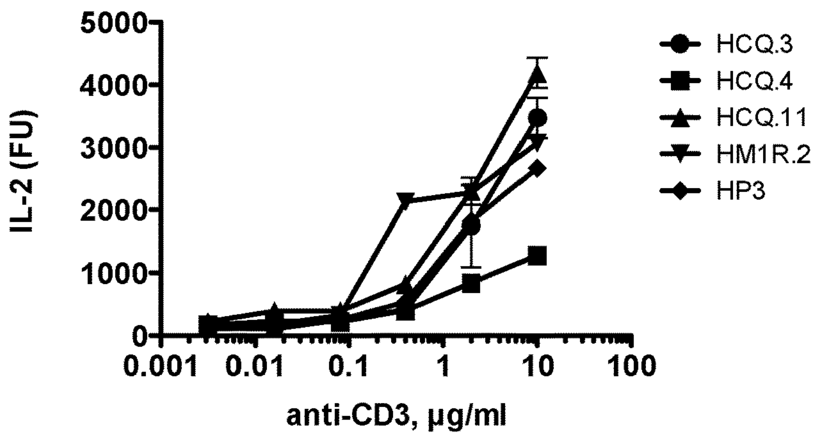

In order to evaluate which posttranslational modifications were present when the Aq/rCII(259-273) complex was produced in HEK293 cells, Aq-restricted T cell hybridoma clones with different specificities for the CII259-273 epitope were stimulated in vitro with the purified complex (FIG. 2).

Control MHC II/CII complexes were produced in S2 insect cells, which have a strongly impaired capacity to produce posttranslational modifications in terms of O-linked glycosylation of lysine side chains. As expected, only the HCQ.4 clone, which recognizes the CII259-273 peptide with a non-modified or hydroxylated lysine at position 264, responded to the Aq/rCII(259-273) complex produced in S2 insect cells. In contrast, all CII-specific clones responded to the Aq/rCII(259-273) complex produced in HEK293 cells. Other specificities of the T cell hybridoma clones used are as follows: HCQ3 (CII, Gal-HK264), HCQ.4 (CII, not modified and HK264), HCQ.11 (Glc-Gal-HK264), HM1R.2 (CII, Gal-HK264 and Gal-HK264+270), HP3 (Aq-restricted, pepsin-peptide). This shows that position 264 can indeed become post-translationally modified when produced in HEK293 cells. Furthermore, the resulting complex is heterogenous where position 264 includes non-modified and/or hydroxylated lysine as well as glycosylated lysines with both mono- and disaccharides. The Aq-restricted clone HP3, which is specific for a pepsin-peptide did not respond to any of the Aq/rCI1(259-273) complexes.

Example 2: In Situ Glycosylated Aa/rCII in a Mouse CIA Model

Figure 3:
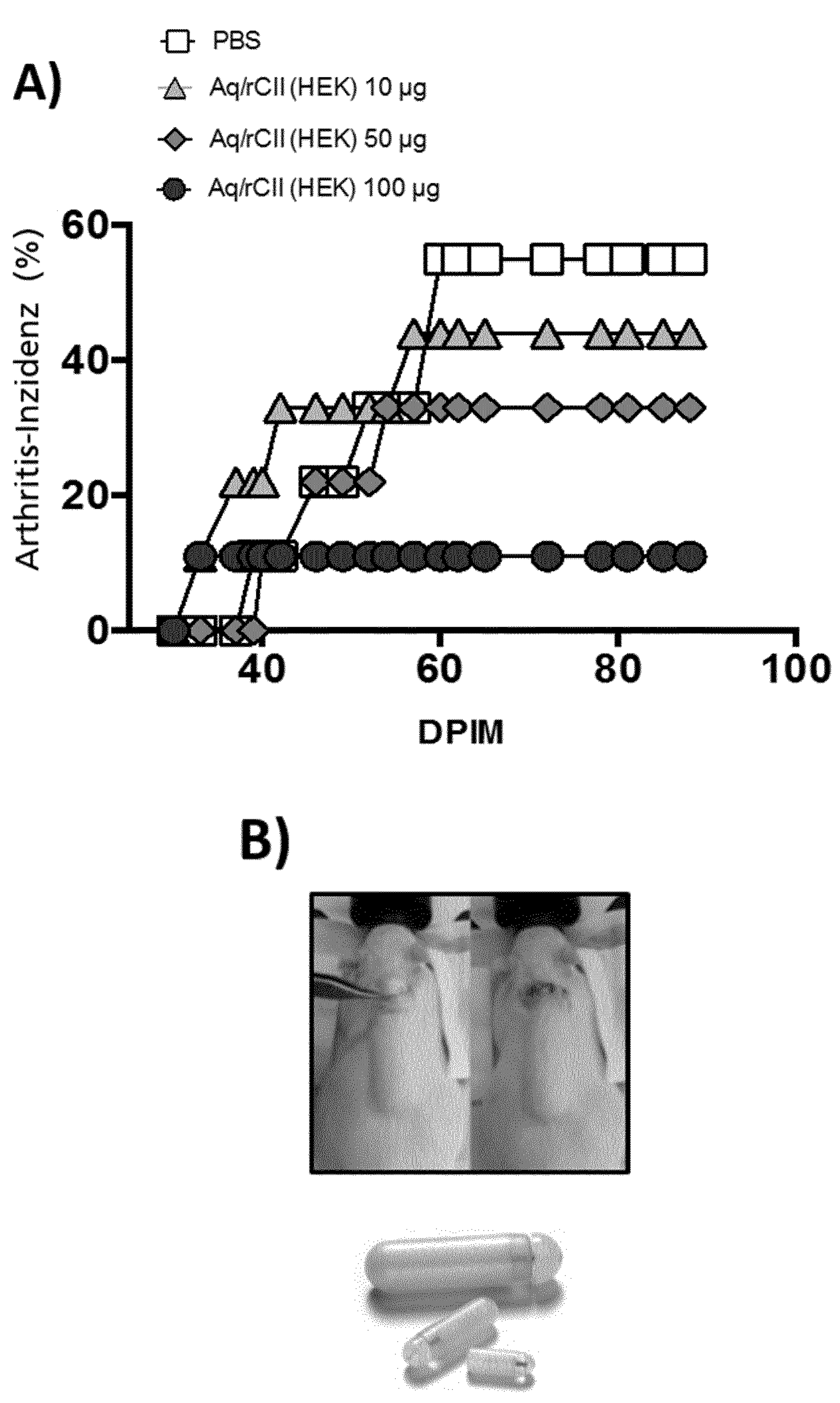
FIG. 3: Therapeutic vaccination using in situ glycosylated Aq/rCII produced in HEK 293 cells in a mouse CIA model. A) dose-response-curve: Naive mice were immunized with CII to induce arthritis and received a boost immunization at day 35. Mice were treated with different dosages of the MHC II/CII peptide complex: 10, 50 or 100 μg (n=9). The number of arthritic mice is significantly lower in the 100 ug treatment group compared to control ($p<0.05$, chi-square) B) To administer the MHC II/CII peptide complex osmotic pumps were implanted 7 days following boost immunization at day 35 to ensure a continually administration of the vaccine (e.g. 100 μg: 15 μg/24 h for 7 days).

Mice immunized with CII in adjuvants were implanted 7 day later (following boost immunization 35 days after the initial immunization) with osmotic pumps loaded with three different amounts of HEK293-produced Aq-rCII(259-273) complex and followed for development of arthritis. Mice were implanted with pumps loaded with PBS only as negative control. As shown in FIG. 3A, Aq-rCII(259-273) complex conferred protection in a dose dependent manner and mice treated with the highest amount of Aq-rCII(259-273) complex (100 μg) completely protected from developing arthritis. Mice treated with the intermediate amount (50 μg) of the Aq-rCII(259-273) complex showed some protection, whereas treatment with the lowest amount (10 μg) resulted in a frequency of arthritis that was comparable to PBS-treated controls.

Example 3: Production of Functionally Active DR4/hCII in HEK 293 Cells

We have proven that functional mouse MHC II/CII complexes (Aq/rCII) can be prepared in HEK293 cells using the in situ glycosylation machinery of the host cell. We next investigated whether human MHC II/CII complexes can be prepared in HEK293 cells using the in situ glycosylation machinery of the cell. The complexes were prepared as described above in HEK293 cells. Control complexes were expressed in CHO cells and loaded with not modified peptide (DR4/nCII) or galactosylated peptide (DR4/galCII). Two activation restricted human T cell hybridomas (3H8: unmodified CII-epitope, mDR1.1: galactosylated CII-epitope) were used to check the galactosylation status of the naturally glycosylated DR4/peptide complex (DR4/hCII) compared a DR4/peptide complex loaded either with not modified peptide or galactosylated peptide. As shown in FIG. 4A, the T cell hybridoma mDR1.1 gets activated upon stimulation with the DR4/galCII complex, whereas stimulation with the DR4/nCII remains almost negative. In comparison to the DR4/galCII and DR4/nCII, the DR4/covalently linked CII (DR4/hCII) is a heterogeneous product with regard to the galactosylation status. That means the composition comprising the DR4/hCII complex contains peptides with galactosylated and unmodified lysine residues in position 264. Activation level of cells stimulated with the DR4/hCII is slightly lower compared to the DR4/galCII complex and very similar to the DR4/nCII complex (FIG. 4B, using 3H8 cells).

Example 4: Detecting CII Peptide Specific T Cells in Humans

The aim was to establish a tetramer based method to directly detect antigen specific T cells in the peripheral blood (PBMCs) of RA patients and healthy donors. Therefore, biotinylated DR4/CII peptide complexes were incubated with either Streptavidin-PE or Streptavidin-APC. To reduce unspecific binding of the tetramers, a double tetramer staining by using two fluorochromes was performed. Antigen specific T cells (CII259-273, K264 gal) using DR4/galCII tetramers can be detected in RA-patients as well as in healthy donors (Figure SA). Moreover, T cells with specificity for the unmodified CII peptide can be detected using DR4/nCII tetramers (Figure SB). The mean frequency of antigen specific T cells is higher using the naturally glycosylated DR4/hCII tetramers compared to DR4/galCII tetramers or DR4/nCII tetramers (Figure SB). Since the frequency of antigen-specific T cells in the peripheral blood is quite low (0.01-0.1%), the observed numbers are as expected.

Figure 5:
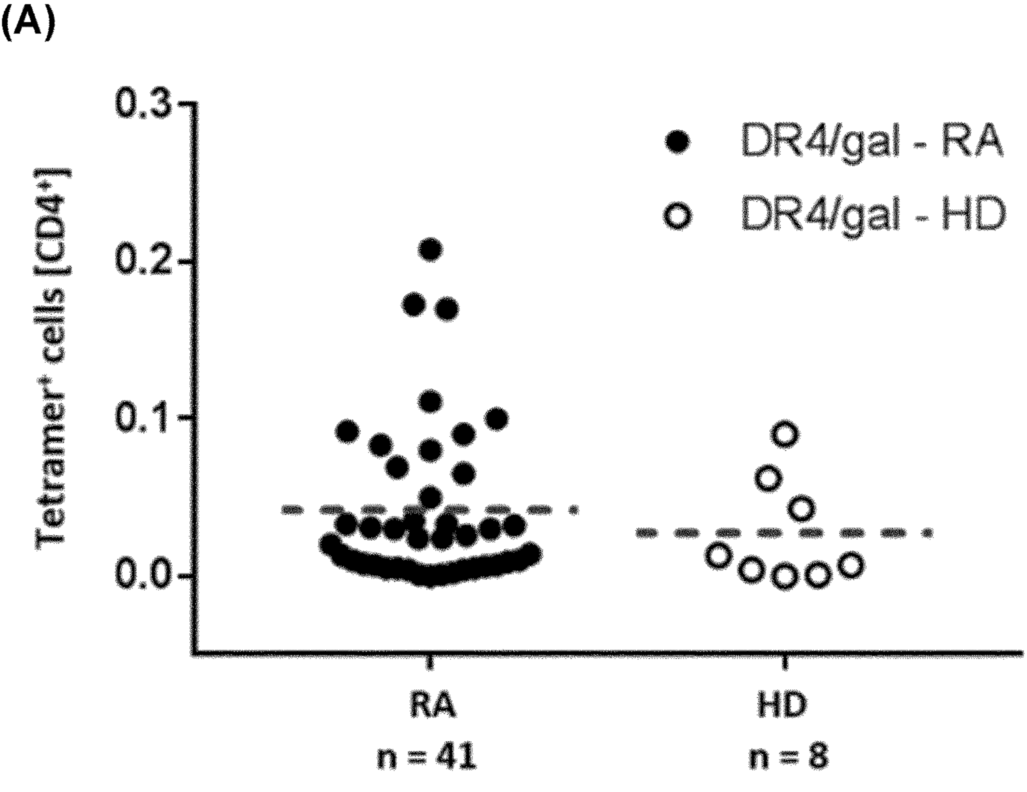
FIG. 5: Detection of antigen specific T cells in the peripheral blood of HLA-DRB1*0401 patients with rheumatoid arthritis. A) Biotinylated DR4/galCII peptide complexes were incubated with fluorochrome (PE, APC) conjugated streptavidin. These tetramers were used to detect T cells specific for the CII259-273 peptide with a galactosylation at K264. Antigen specific (CII259-273, K264 gal) T cells in PBMCs of RA patients and healthy donors were detected using flow cytometry. B) Comparison of frequency of antigen specific T cells using DR4/galCII peptide tetramers, DR4/nCII peptide tetramers or DR4/hCII peptide tetramers for detection. The frequency of tetramer positive T cells within the CD4+ T cell population was measured by flow cytometry.
Figure 5:
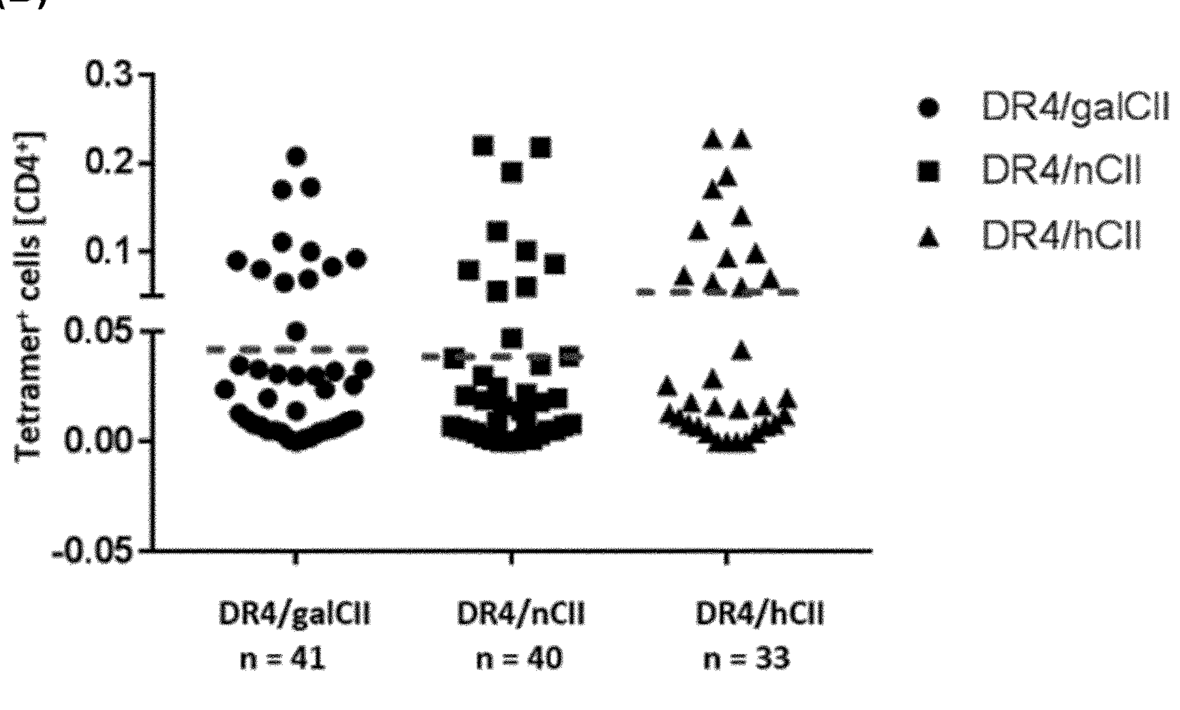
Figure 6:
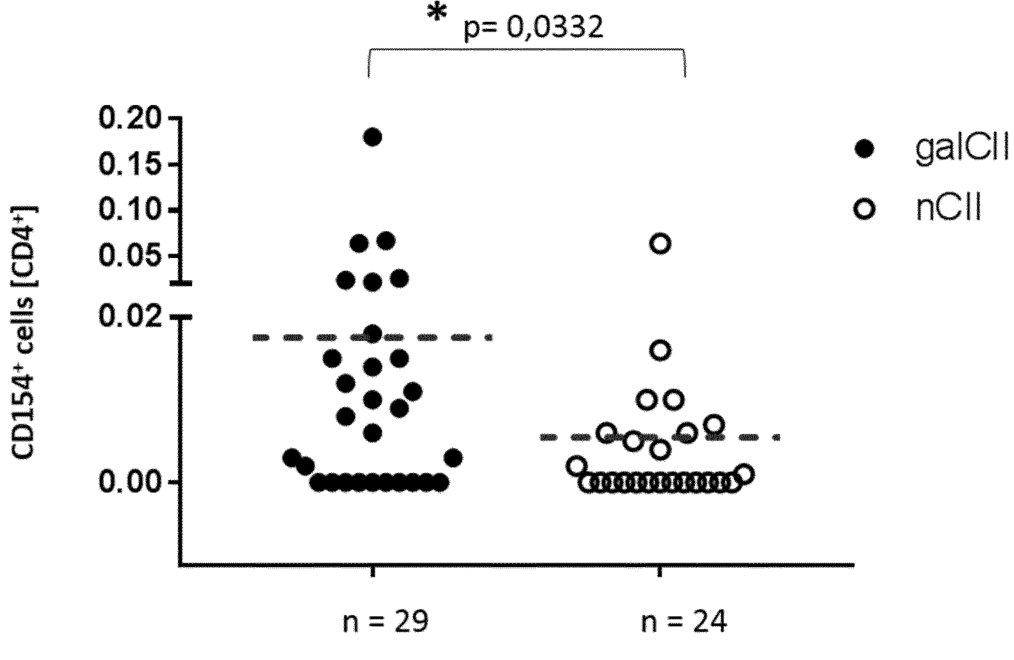
FIG. 6: Human T cell activation. Detection of antigen specific T cells in the peripheral blood of HLA-DRB1*0401 RA patients. T cells get activated upon galCII and to a lesser extent by non-modified CII peptide stimulation. The upregulation of CD154 was measured by flow cytometry (significance: p-Value=0.0332, Mann-Whitney-Test).

Activated CD4+ T cells were also detected in PBMCs of HLA-DRB1*0401 RA patients following galCII peptide stimulation by flow cytometry using CD154 (CD40L) surface staining as a marker for T cell activation (FIG. 6). As a positive control cells were also incubated with superantigen SEB, leading to strong upregulation of the activation marker CD154 (data not shown). In contrast, cells incubated only with an antibody against costimulatory CD28 were mainly negative (data not shown). Since the expected frequency of the antigen-specific T cell population is quite low in the peripheral blood, the detection of 0.01-0.1% CD154+ T cells (parent population: CD3/CD4 living T cells) is satisfying. Remarkable is the fact that T cells get less activated using the unmodified (naked) CII peptide. Since numbers of antigen specific T cells using DR4/galCII or DR4/nCII tetramer staining were similar in PBMCs of HLA-DRB1*0401 RA patients (FIG. 5), the difference observed following peptide activation seems to be due to a difference in activity or functional status of the respective T cells.

Figure 7:
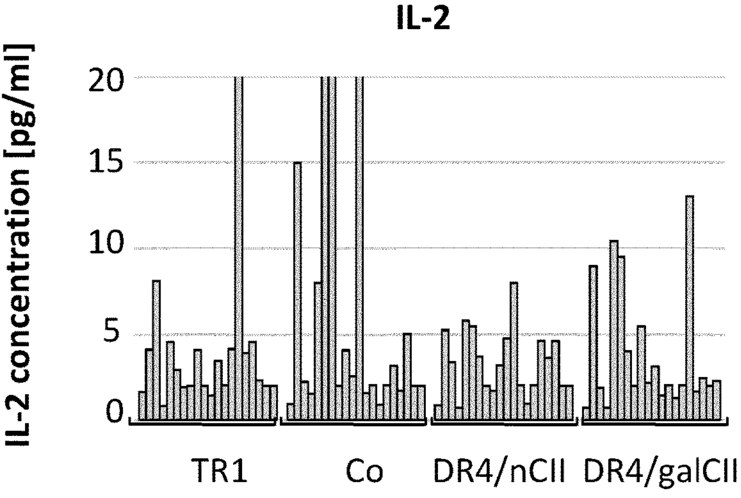
FIG. 7: Legendplex™ analysis of cytokine release by PBMCs from HLA-DRB1*0401 positive RA patients (n=20) stimulated in vitro. Shown is the specific induction of IL-2, IL-17f, IFN-γ IL-10, IL-17a and, TNF-α release by in vitro stimulation with DR4/nCII peptide complex or DR4/galCII peptide complex in comparison to stimulation with standard TR1 cell differentiating conditions (TR1) and negative control (CO).
Figure 7:
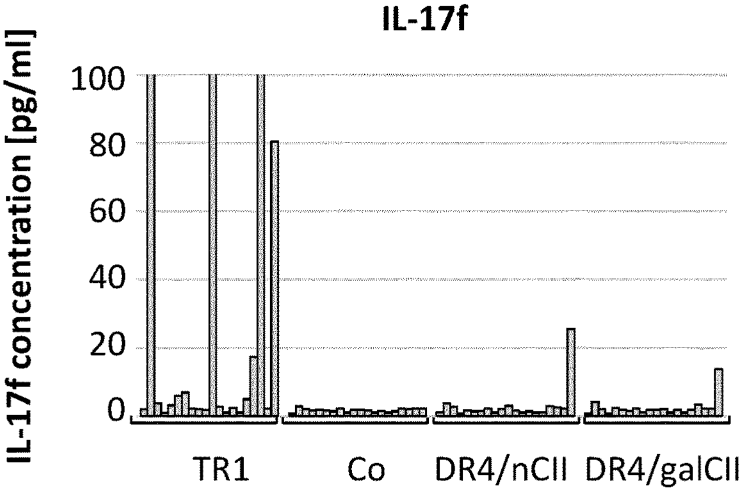
Figure 7:
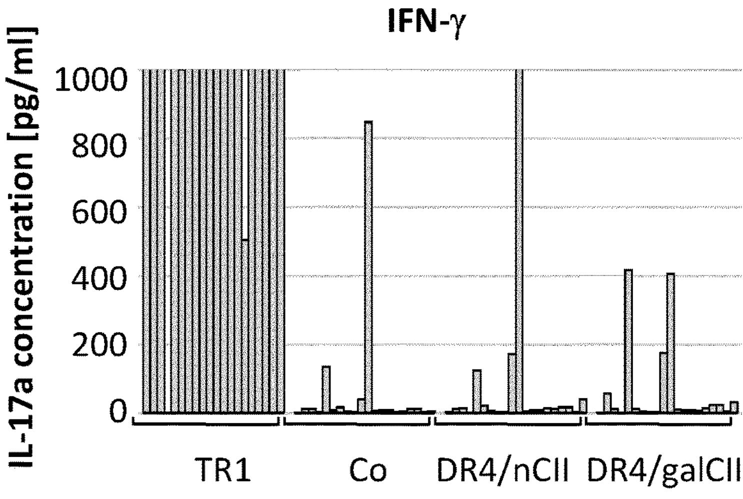
Figure 7:
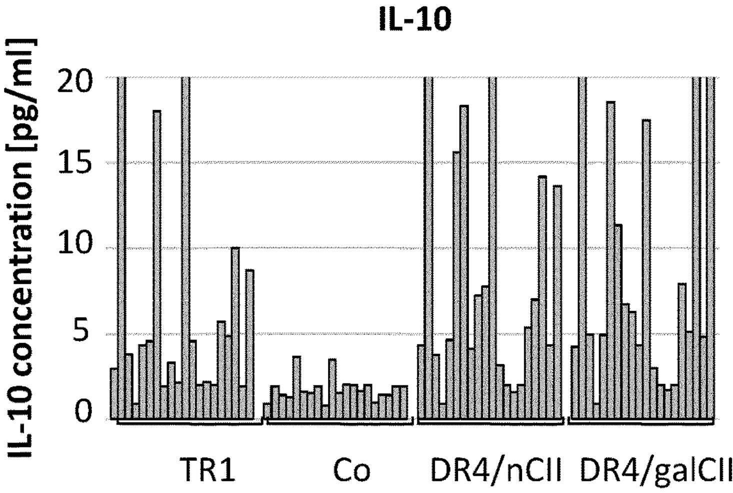
Figure 7:
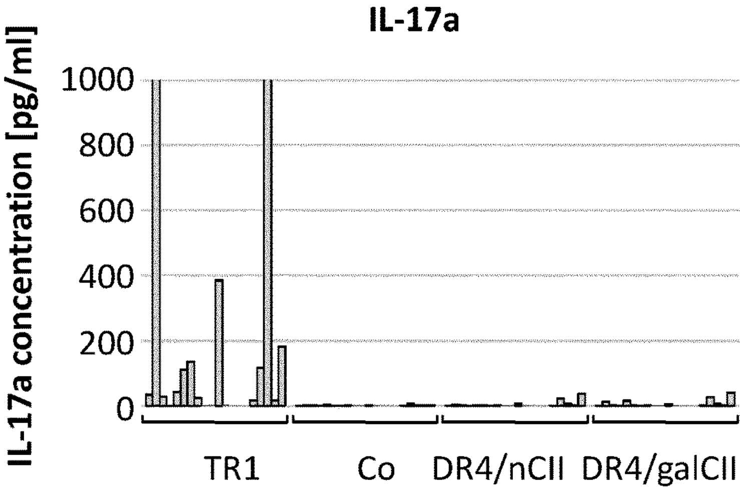
Figure 7:
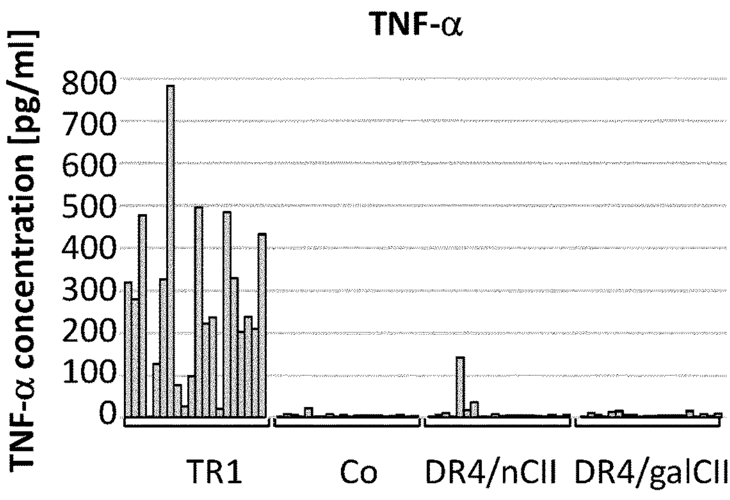

Example 5: In Vitro Stimulation/Differentiation of T Cells from the Peripheral Blood of HLA-DRB1*0401 Positive RA Patients In vitro studies were performed to investigate the induction/differentiation of regulatory T cell functions e.g. the upregulation of the Tr phenotype associated cytokine IL-10 upon stimulation with DR4/CII-monomers for a prolonged incubation period of eight days. Accordingly, isolated PBMCs from genotyped HLA-DRB1*0401 positive RA patients were either stimulated under Tr cell inducing conditions with anti-CD3 and IL-27 (positive control, T1), with DR4/nCII (3.6 μg/ml), DR4/galCII, (3.6 μg/ml), or without stimulation (negative control, K1) for 8 days. Stimulation was done in duplicates. At day 8 the culture supernatants were collected and analyzed for cytokine release using a custom-made panel for human cytokines in a multiplex bead-based LEGENDplex™ assay format according to the manufacture's protocol. The results shown in FIG. 7 clearly demonstrate the capacity of DR4/nCII and DR4/galCII to induce the release of the anti-inflammatory cytokine IL-10 in PBMCs from RA patients and at levels even slightly higher compared to positive controls incubated under conventional TR1 inducing conditions for 8 days. There is no evidence for a concomitant activation of pathways leading to an increased production of pro-inflammatory cytokines e.g. TNF-α, IL-2, IL-17a, IL-17f, or IFN-γ.

Figure 8:
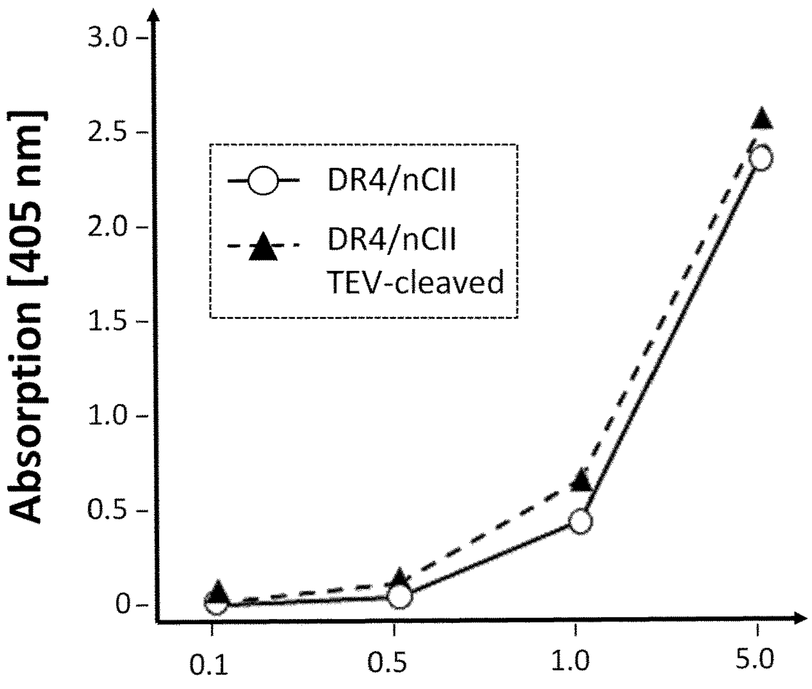
FIG. 8: Comparison of complexes with and without His-tag. (A) ELISA comparing the coating efficacy of microtiter wells by equimolar solutions of DR4/nCII vs. DR4/nCII Tev-cleaved complexes using a DR4-specific antibody and a peroxidase-coupled secondary antibody. Shown is the absorption at 405 nm at the indicated protein concentration of the DR4/nCII solutions used for coating to the microtiter plates [μg/ml]. (B) Activation of 3H8 hybridoma cells by DR4/nCII vs. DR4/nCII Tev-cleaved complexes pre-coated to microtiter wells at the indicated concentrations. Shown are IL-2 concentrations in the supernatant following activation at the indicated protein concentration of the DR4/nCII solutions used for coating to the microtiter plates [μg/ml].
Figure 8:
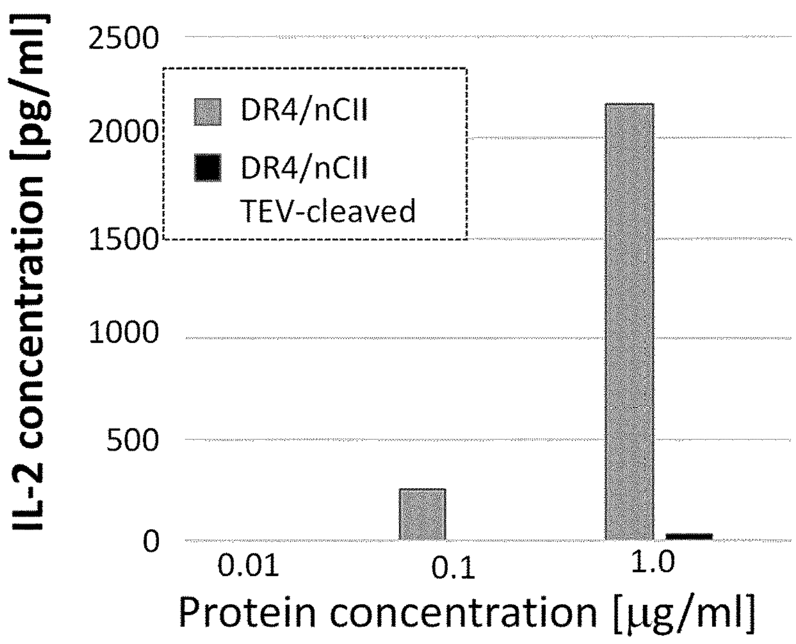

Example 6: The His-Tag in the DR4/CII Peptide Complex: Contribution to the Pharmacological Effect It has been investigated whether sequences not directly essential for the MHC II/CII complex can be omitted from the construct, including the contribution of the polyhistidine-tag (His-tag), the biotinylation site, the TEV cleavage site, the thrombin cleavage site and the strep-tag to the T cell activating properties of the recombinant complex. Typically the DR4/CII peptide complexes as well as the anti-CD3 antibody (positive control) are coated to the plastic surface of the microtiter wells in a standard hybridoma activation assay. In initial experiments we used the internal TEV-cleavage site of the DR4/nCII peptide complex to investigate the effect of proteolytic cleavage of the His-tag on activation of T-hybridoma cells (3H8) measured by IL-2 secretion in comparison to the uncleaved DR4/hCII peptide complex coated to microtiter wells. Efficacy of proteolytic cleavage was controlled by Western Blot analysis. Further, equivalent coating efficacy of the microtiter wells using equimolar solutions of the cleaved and uncleaved complex was confirmed by ELISA using a DR4-specific antibody and a peroxidase-coupled secondary antibody (FIG. 8). This also confirms that the complex did not dissociate and is present as a heterodimer. Our data show a strong decrease of the cleaved construct in activating the T hybridoma cells although the functional domain of the DR4/nCII complex recognized by the TCR of the T hybridoma cells is coated with a similar efficacy to the plastic surface (FIG. 8). It is highly unlikely that the zipper cleavage lead to a dissociation of the complex. The zipper is primarily needed for the formation of the complex during the biosynthetic process, whereas the formed MHC II-peptide-complex itself is rather stable at least in vitro due to the stabilizing effect of the peptide bound to the binding groove formed by the variable regions of both chains.

Figure 9:
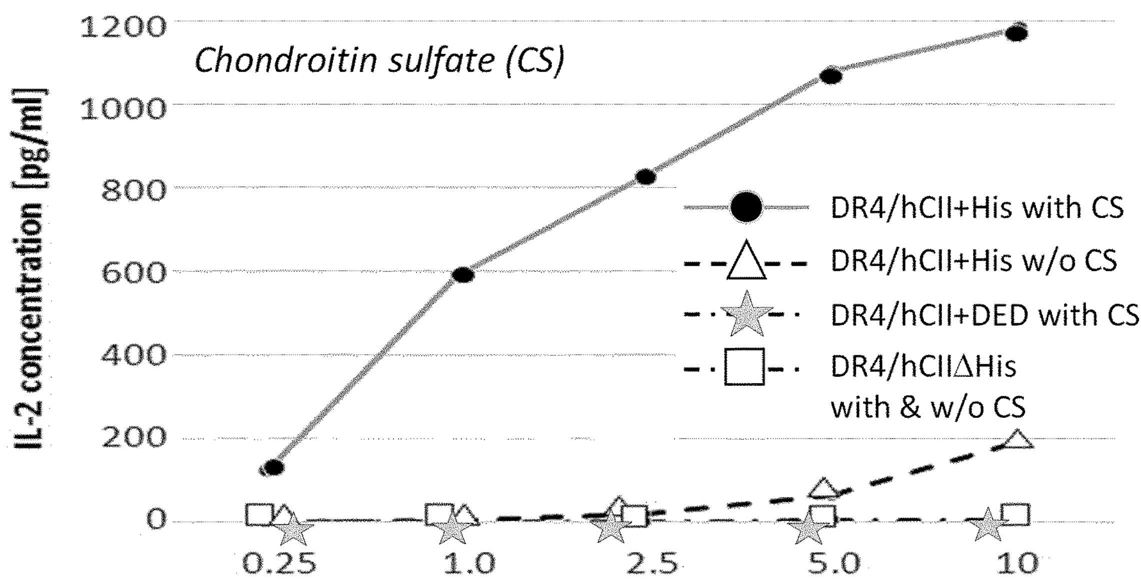
FIG. 9: Impact of the His-Tag in DR4/hCII peptide complexes and their interaction with A) chondroitin sulfate (CS) B) hyaluronan C) heparan sulfate (HS) on T cell activation: Induction of an IL-2 response in 3H8 hybridoma cells by DR4/hCII vs. DR4/hCIIb.His and in (A) also DR4/hCII_DED at the concentrations indicated in solute phase in microtiter wells either blocked or precoated with chondroitin sulfate. Shown are IL-2 concentrations in the supernatant following activation.
Figure 9:
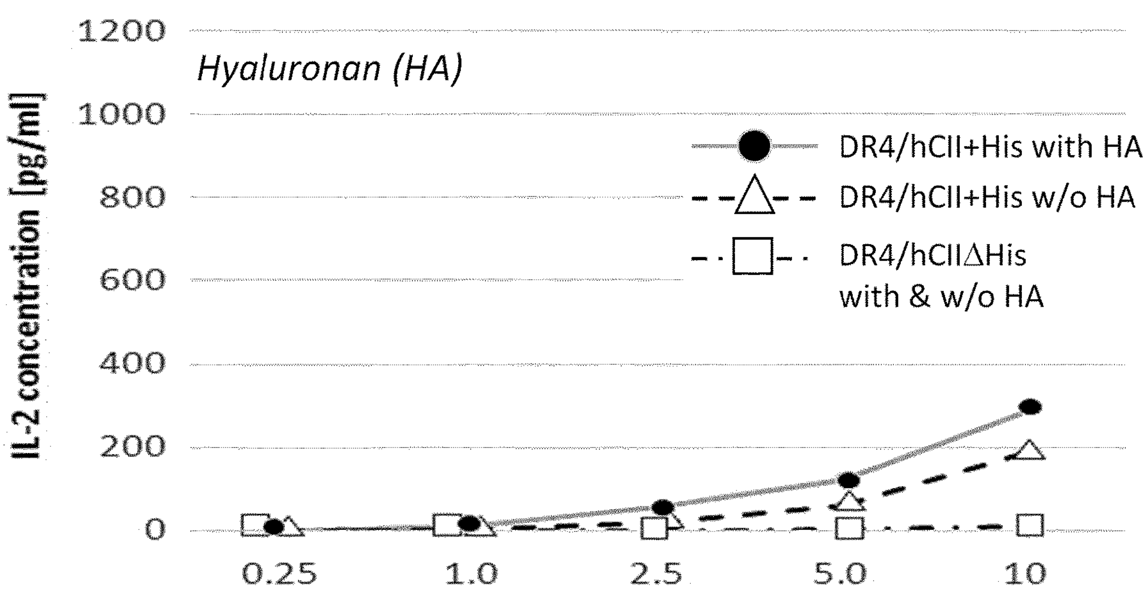
Figure 9:
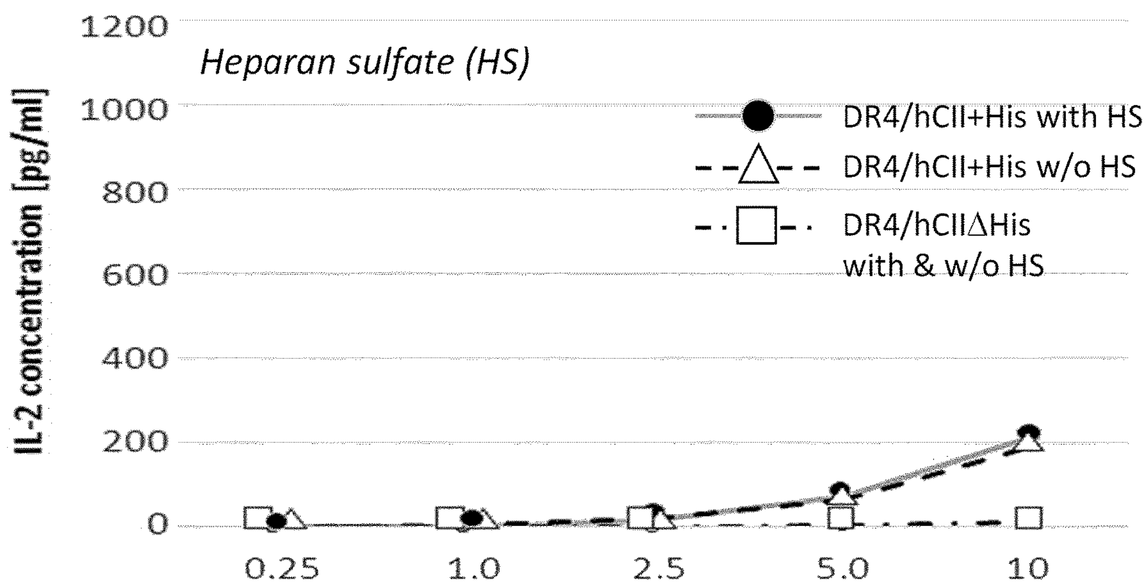

We concluded that the His-tag in the uncleaved DR4/nCII complex is required for the correct orientation of the complex on the surface in a multimerized alignment exposing the peptide binding groove towards the T cell by preferentially contacting charged contact areas on the plastic surface. To confirm this conclusion, DR4/hCIIb.His complex was produced that only lacks the His-tag (6His) at the carboxy-terminal end of the MHC class II beta chain, but is otherwise identical to the DR4/hCII complex, i.e., contains the JUN/FOS heterodimerization domains (compare FIG. 1). As an additional control for the involvement of electrostatic interactions by the positively charged functional imidazole group of histidine, a further mutated recombinant variant of the DR4/hCII complex was prepared, in which the His-tag was replaced with a triplet of negatively charged amino acid residues Asp-Glu-Asp (OED) (DR4/hCII_DED). Also, we exchanged the unphysiological material plastic with charged extracellular matrix (ECM) components (chondroitin sulfate, heparin sulfate, hyaluronan) present on cell surfaces, in extracellular body fluids such as synovial effusions or the lymph as well as in tissues, such as joint cartilage or synovial membranes. For this purpose we first coated microtiter wells with highly concentrated solutions of chondroitin sulfate, heparin sulfate and hyaluronan solutions (10 mg/ml). The coated surfaces were washed thoroughly and in vitro stimulation experiments of 3H8 hybridoma cells were performed by adding the DR4/CII peptide complexes to the fluid phase using IL-2 concentrations in the supernatant as a read-out. For control, parallel experiments were performed in microtiter plates with blocked surfaces in the absence of the ECM-components. The results shown in FIG. 9A demonstrate that under these conditions only the complex containing the His-tag induced a strong IL-2 response and that its ability to activate T cells seems to be critical dependent on chondroitin sulfate coated to the surface of the microtiter wells, whereas the impact of hyaluronan (HA) remained less pronounced (Fib. 9B) and hardly detectable for heparin sulfate (FIG. 9C). The soluble DR4/hCII_DED control complex did not induce an IL-2 response in the presence of chondroitin sulfate coated surface of microtiter wells (FIG. 9A). However, the observed effect of the His-tagged complexes cannot simply be explained by electrostatic interactions of polysulfated anionic glycosaminoglycans via the positively charged imidazole groups of the polyhistidine tag, since heparan sulfate likewise contains a high degree of negatively charged sulfate groups, but does not seem to significantly facilitate the IL-2 response of the 3H8 hybridoma cells stimulated by the solute His-tagged DR4/hCII complex. Accordingly, the results suggest a specific interaction of the polyhistidine tag with the chondroitin sulfate matrix to increase the IL-2 response by 3H8 hybridoma cells stimulated with the dissolved DR4/hCII complex.

Figure 10:
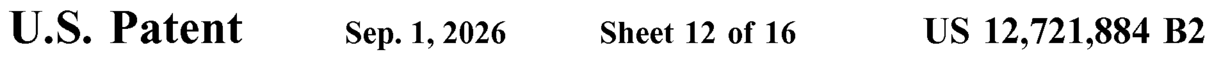
FIG. 10: Activation of 3H8 hybridoma cell by DR4/hCII vs. DR4/hCIIb.His vs. DR4/hCII_DED precoated to microtiter wells at the concentrations indicated. Shown are IL-2 concentrations in the supernatant following activation at the indicated protein concentration of the DR4/nCII solutions used for coating to the microtiter plates [μg/ml].
Figure 10:
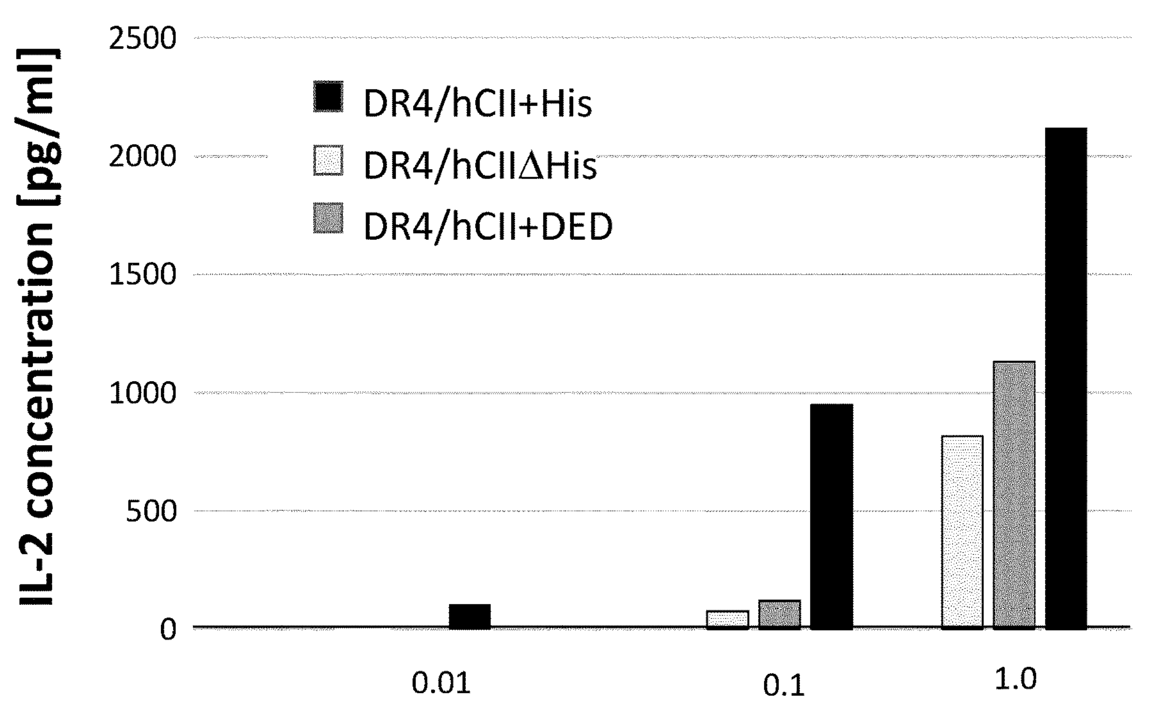
Figure 10:
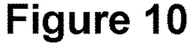

In parallel T hybridoma cell stimulation experiments using direct coating of the different DR4/hCII constructs to the plastic surfaces at three different concentrations (0.01 mg/ml, 0.1 mg/ml and 1 mg/ml), the initial results obtained with the Tev-cleaved DR4/nCII complexes were confirmed. The capacity to induce an IL-2 response by the DR4/hCIIb.His complex as well as the mutated DR4/hCII_DED complex is strongly reduced using 0.1 mg/ml and 1 mg/ml for coating. However, a response was observed using 1 mg/ml for coating at a level comparable to the unmodified complex (DR4/hCII) at a 10-fold lower coating concentration (FIG. 10).

Figure 11:
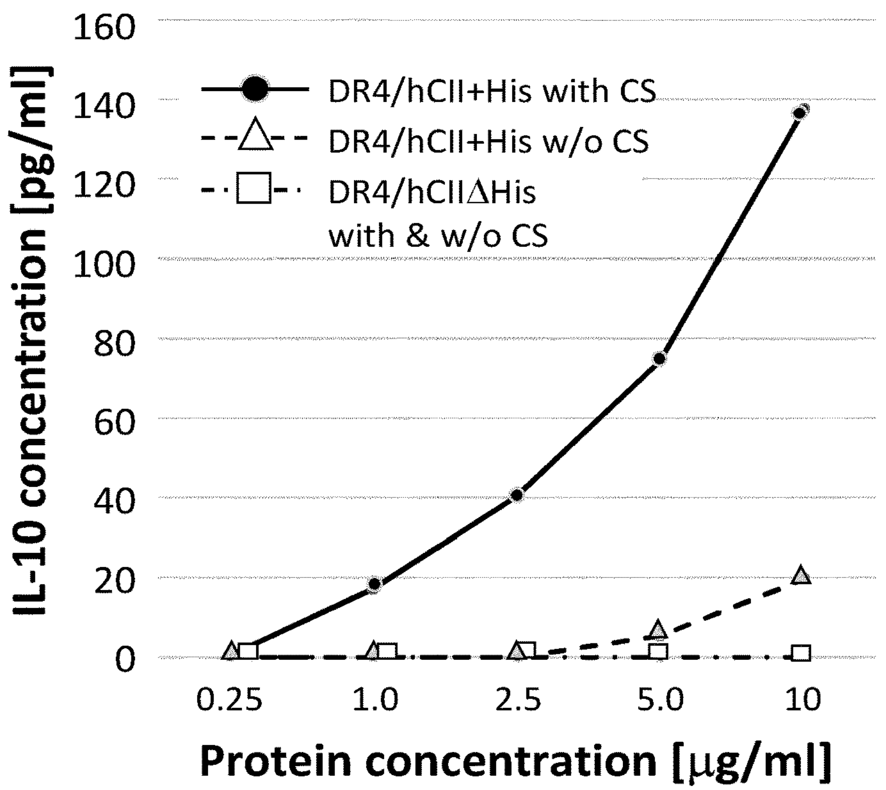
FIG. 11: Impact of the His-Tag in DR4/hCII peptide complexes and their interaction with chondroitin sulfate (CS) in solute phase to stimulate an IL-10 responses in 3H8 hybridoma cells: Activation of 3H8 hybridoma cells by DR4/nCII at the concentrations indicated in a solute phase with or without (w/o) chondroitin sulfate (2.5 mg/ml) in microtiter wells with a blocked plastic surface. Shown are IL-10 concentrations in the supernatant following activation at the indicated protein concentration of the DR4/nCII solutions used for coating to the microtiter plates [μg/ml].

However, the experiments also demonstrate that all constructs harbor the functional peptide in the DR4-binding groove as a requirement for TCR activation of the 3H8 hybridoma cells. Accordingly, our studies provide unequivocal evidence that the His-tag in the DR4/CII complex improves activity of the complex. Without being bound by theory, the His-tag seems to provide an improved spatial orientation of the peptide binding groove for TCR recognition via an impact on the interaction with the ECM component chondroitin sulfate. In addition, subsequent studies shown in FIG. 11 demonstrate that the interaction of the DR4/CII complex comprising a His-tag with chondroitin sulfate or with hyaluronan in the solid phase in a microtiter well with blocked plastic surfaces can enhance its capacity to stimulate an IL-10 response by the T hybridoma cells.

Figure 12:
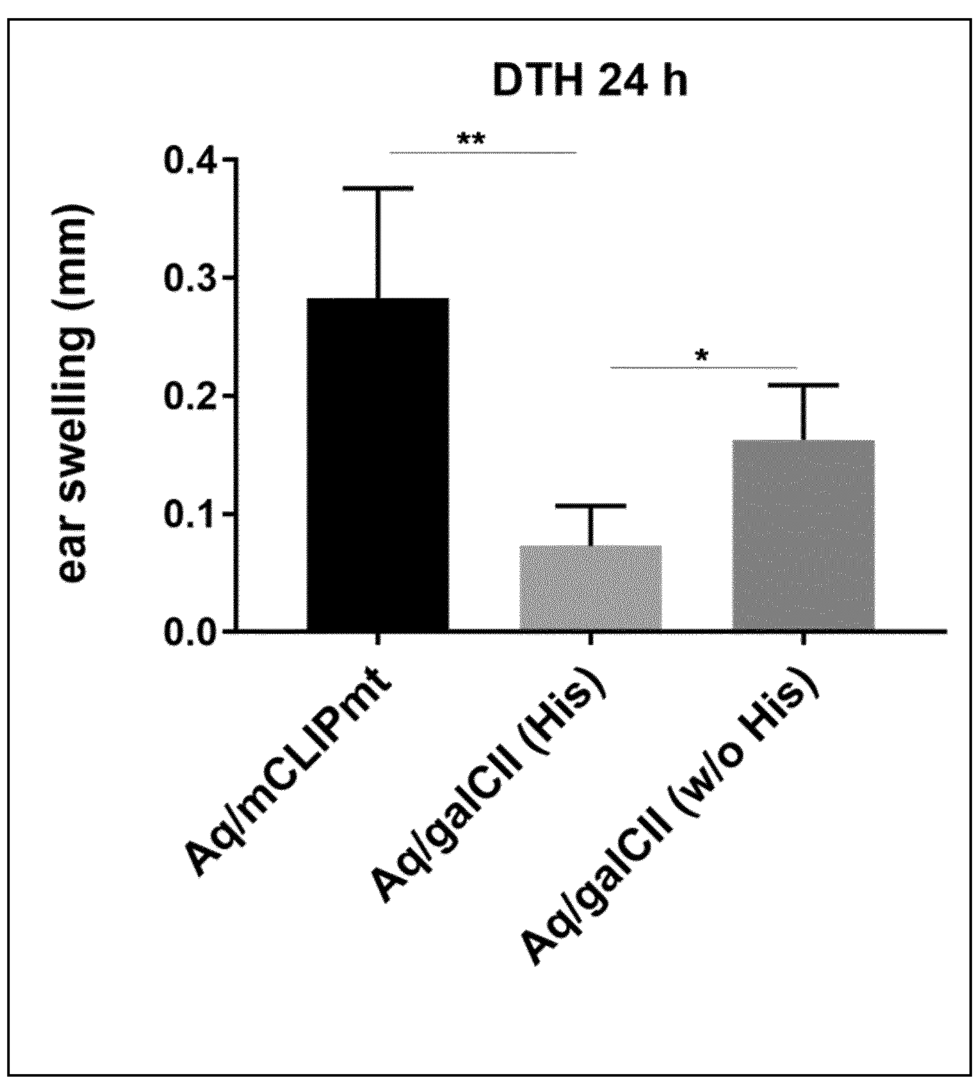
FIG. 12: Comparison of the therapeutic effect of Aq/galCII peptide complex either containing or lacking a His-tag on ear swelling induced by the DTH reaction to collagen II in vivo. The effect of the Aq/galCII construct with (His) and without the polyhistidine tag (w/o His) are shown in comparison to an Aq/mCLIPmt control construct containing a linked mouse mutated CLIP peptide in its binding groove (CLIPmt) (* indicates a p value of <0.05 and** indicates a p value of <0.01).

The in vitro data support a critical functional role of the His-tag in the DR4/CII complex for its immunomodulatory pharmacological effect. Furthermore an in vivo study using the model of the T cell dependent CII-induced hypersensitivity reaction in Aq expressing QB mice was performed. CII-preimmunized mice were triggered at day 8 post immunization by an intradermal CII injection into one ear to develop a T cell dependent inflammatory swelling controlled by a vehicle trigger applied to the contralateral ear. Prior the induction of the DTH reaction the mice received treatment on day 4 postimmunization by a 24 h sc. pump-infusion of either a His-tag containing Aq/galCII complex, an Aq/galCIIΔHis complex lacking the His-tag or a control Aq/CLIP complex containing a linked control peptide [class II associated invariant chain: CLIP] in its binding groove. The results shown in FIG. 12 provide clear evidence for the functional impact of the His-tag on the therapeutic reduction of the T cell dependent ear swelling induced by the experimental CII-specific DTH-reaction. Thus, our studies consistently demonstrate an improved function of the MHCII/CII peptide complexes comprising a polyhistidine sequence for the immunomodulatory therapeutic effect on T cells, which is most likely mediated via its impact on the interaction with ECM components that are abundantly available in the context of targeted structures on cell surfaces, tissue components and body fluids in vivo.

Figure 13:
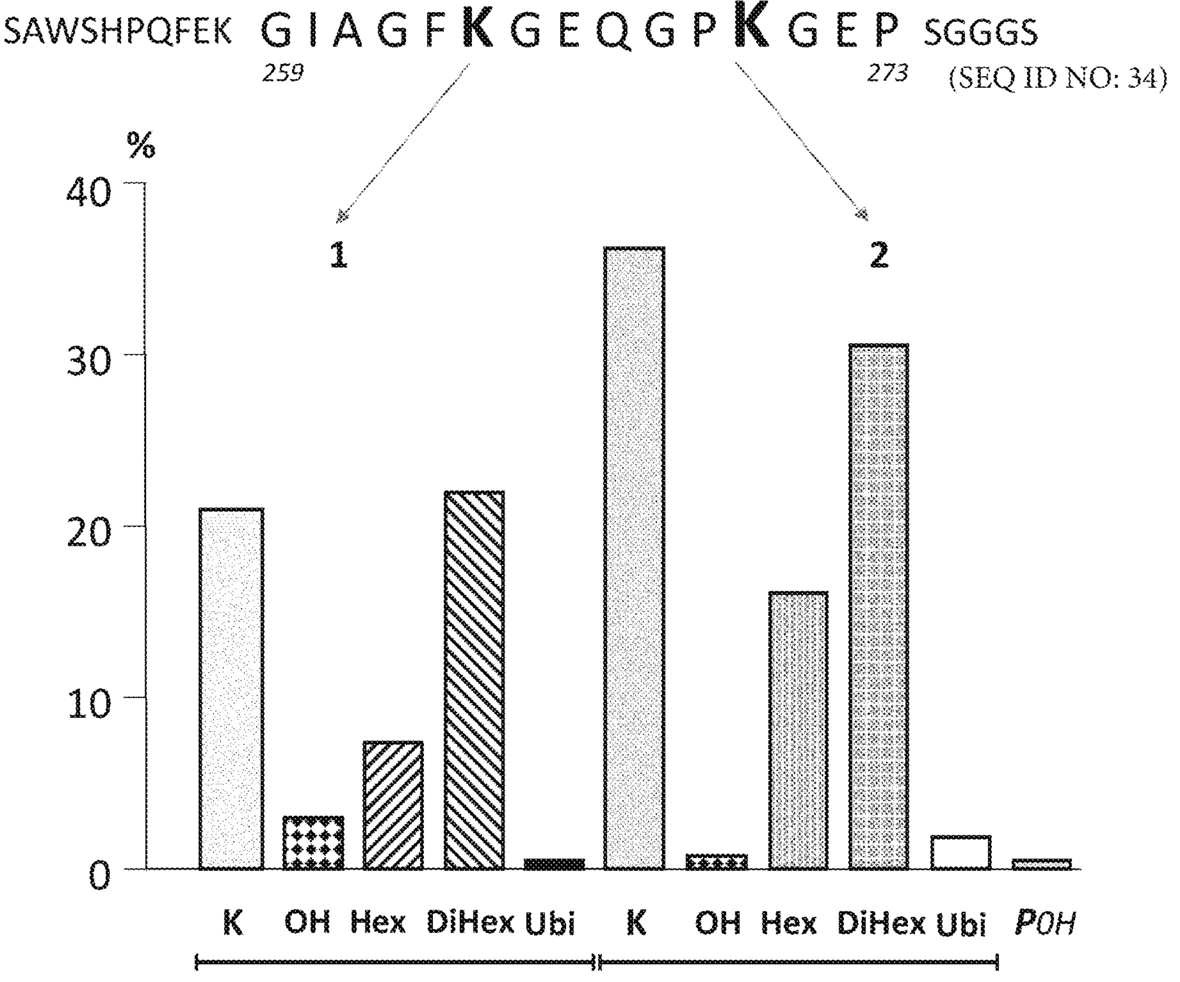
FIG. 13: Heterogeneity in the posttranslational modification of the CII-peptide in the recombinant DR4/hCII complex. The percentage of detectable modifications at the respective position at the indicated K position as analysed by mass spectrometric analysis is shown. [OH=hydroxylysine, Hex=galactosyl-hydroxylysine, DiHex=glucosyl-galactosyl-hydroxylysine, Ub=ubiquitine, POH=hydroxyproline.

Example 7: Obstacles of the Recombinant Production of the DR4/Gal CII Complex in HEK Cells The posttranslational modification of the CII sequence of the peptide in the binding groove of the recombinant DR4-complex involves several sequential steps by different enzymes. These collagen-specific posttranslational modifications preferentially affect the lysine residues at positions 264 and 270. The initial step is a lysyl hydroxylation mediated by a lysyl hydroxylase followed by a galactosyl transfer to the hydroxylated lysine mediated by a galactosyl transferase. Further, a single glucose residue may be added to the galactosylated hydroxylysine. All these steps occur during the biosynthetic process in cells with a post-translational machinery for collagen, such as in HEK cells, thereby leading to a heterogenous recombinant product comparable to the natural ECM-protein in cartilage in vivo. In humans, this mixture is likely advantageous for the purpose of increasing the spectrum of potential T cells that can be recruited from the entire repertoire for modulation into regulatory cells to produce anti-inflammatory mediators such as IL-10 to dampen the immune-mediated joint disease. The studies on the in vitro activation of IL-2 and IL-10 responses in T cells from peripheral blood of RA patients in response to recombinant DR4/CII complexes either containing the galactosylated (DR4/galCII) or the non-modified CII (DR4/nCII) peptide provide experimental support in this direction. However, mass spectrometric analysis of several batches of CR4/hCII produced in HEK cells revealed that a considerable amount of the recombinant proteins exhibit a high degree of disaccharide (Glc-Gal-Hyl) content at both lysine residues (FIG. 13), which is likely to be disadvantageous for TCR recognition due to the coverage of the peptide binding groove by bulky carbohydrate structures thereby disturbing TCR recognition.

The collagen specific post-translational galactosylation of the lysine residues in the CII peptide sequence of the recombinant DR4/hCII constructs especially that at the residue 264 is important for T cell recognition via the TCR and the resulting pharmacological effects. As the lysine residue in position 270 is located at the edge of the binding groove of the DR4 molecule its carbohydrate modification is generally considered not to be involved in TCR recognition. In order to reduce heterogeneity and the potential risk for negative interference with TCR-recognition of the CII-peptide in the DR4 binding groove by the carbohydrate attachment to a hydroxylated lysine residue in position 270 (K270), K270 may be mutated into an arginine residue (R). This mutation has previously been shown not to affect binding to the TCR of antigen-specific T cell hybridoma.

Figure 14:
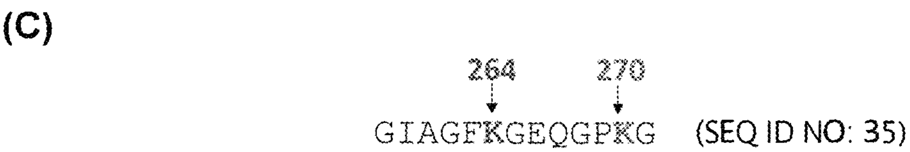
FIG. 14: Generation of Plod3 gene (LH3) knock-down Expi293 cell. (A) Schematic representation of the stepwise transfer from lysine to hydroxylysine to Gal-hydroxylysine and Glc-Gal hydroxyl mediated by the multifunctional collagen-modifying enzyme LH3. (B) Detection of PLOD3 by Western Blot. Lysates from different Expi293 HEK cell clones transduced with $1\times10^6$ lentiviral encoding Plod3 specific sh-RNA were loaded onto a SOS-PAGE and PLOD3 was detected on a Western Blot using an anti-PLOD3 antibody. PLOD3 has a theoretical molecular weight of 84 kDa. Clones #4, #18 and #20 were used for further expansion. (C) Glycan analysis by mass spectrometry. After lentiviral transduction with shRNA to knock-down the plod3 gene, a glycan analysis by mass spectrometry was performed to investigate the reduction of glucosylation of galactosylhydroxylysyl residues. Both lysines (K264 and K270) within the collagen type II epitope (SEQ ID NO: 1) shown at the top were analysed. A clear reduction of gluco-galactosylhydroxylysyl residues (DiHex) is demonstrated. Unmod=unmodified, OH=hydroxylated, DiOH=dihydroxylated, Hex=galactosylatedhydroxylysyl, DiHex=gluco-galactosylhydroxylysyl.
Figure 14:
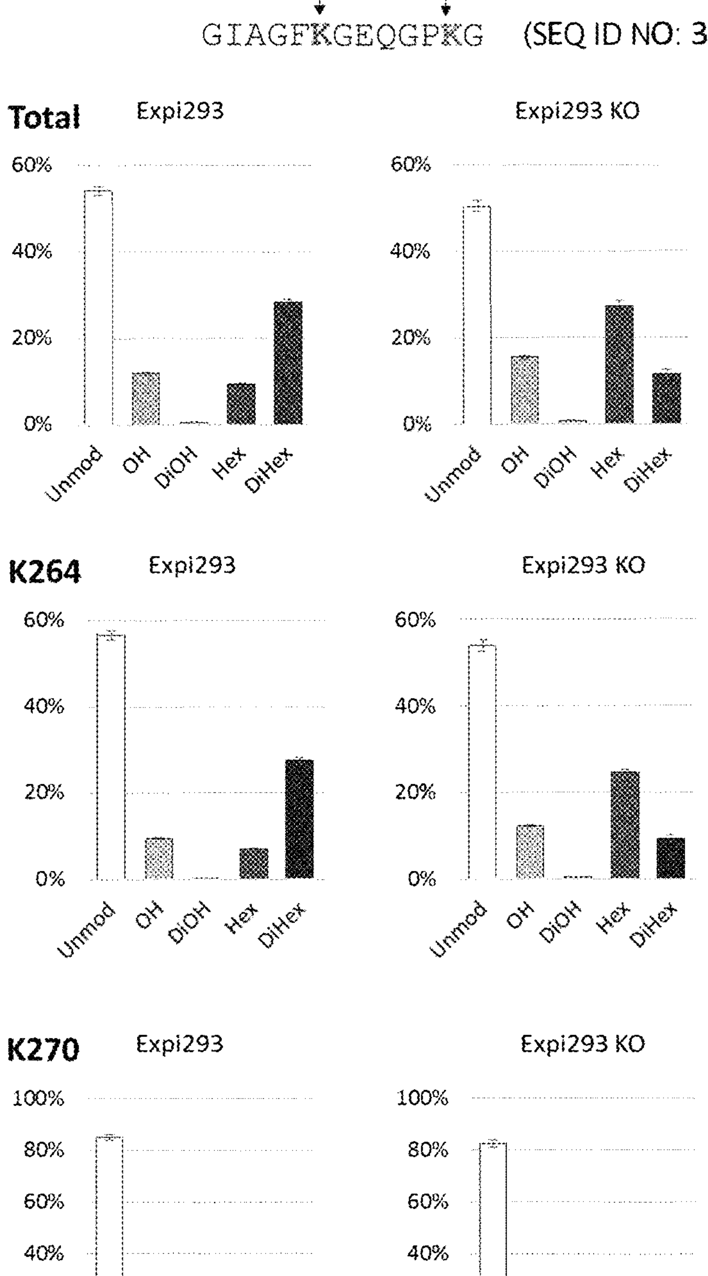

Even more relevant is the prevention of the final transfer of a glucose residue to the galactosylated hydroxylysine in position 264. This carbohydrate moiety is likely to have a negative effect on TCR recognition as the bulky and flexible disaccharide (Glc-Gal) may interfere with the TCR binding. In vitro stimulation of T cells from peripheral blood of RA patients have shown that the unmodified (nCII) as well as the monogalactosylated peptide (galCII) can be recognized. The reaction catalyzing the transfer of the glucose residue to the galactosylated hydroxylysine is the galactosylhydroxylysyl glucosyltransferase (synonymous name: procollagen lysyl-hydroxylase 3 (LH3)). LH3 is a multifunctional enzyme also capable of catalyzing the before mentioned initial steps of lysine modification, i.e., hydroxylation resulting in hydroxylysine (Hyl) and galactosyl transfer resulting in galactosyl-hydroxylysine (Gal-Hyl) (FIG. 14A). However, its non-redundant activity is the final glucose transfer to the galactosyl hydroxylysine.

We therefore genetically engineered Expi293F cells to knock-down the LH3 enzyme. A HEK cell line for the production of the DR4/hCII complex that is selectively made deficient for the final glucosyltransfer to the galactosyl hydroxylysine in the CII peptide is expected to be advantageous in order to improve efficacy of recombinantly produced DR4/hCII complex. This can be achieved by generating HEK293 IH3 knock-out cells, e.g., by introducing a gene disrupting mutation into the Plod3 gene encoding the lysylhydroxylase 3 gene using a CRISPR/CAS gene editing approach.

In a first step we generated Expi293F cells) with a Plod3 knock-down by lentiviral transfection of specific shRNA to investigate the potential of this strategy to obtain a less heterogenous product with an increased specific T cell activating activity by improvement of the recombinant expression system. For transduction Expi293 cells were plated using 200,000 cells/well in 12-well plates followed by shaking the plates at 37° C., 8% CO2 and 120 rpm for 3 hours. 200 ul lentiviral particles (customized lentiviral particles from Sigma) were mixed with 10 ul PEIpro transfection reagent (Polyplus) and add to the cells and incubated for another 4 h under shaking at 37° C., 120 rpm and 8% CO2, 1 ml fresh media was added and continued to incubate for 3 days before analyzing transduction efficiency.

Three days after lentivirus transduction with shRNA targeting Plod3, the cells were divided into two parts. To one-part puromycin was added to a final concentration of 2 μg/ml to kill the untransduced cells and the other part was analysed by flow cytometry to check the transduction efficiency. The cells were under antibiotic selection pressure until non-transduced cells were dead and the transduced cells divided for about 18 days to a viability above 90%. These stable transduced mixed pools were expanded to 500 ml and transfected with DR4/hCII as described above. After purification, glycan analysis by mass spectrometry was performed to investigate the reduction of glucosylation of galactosylhydroxylysyl residues in plod3 knock-down Expi293F cells and Expi293F control cells. Both lysines (K264 and K270) within the collagen type II epitope were analysed. A clear reduction of gluco-galactosylhydroxylysyl residues (DiHex) is visible in Expi293 KO cells (FIG. 14C).

Meanwhile, stably transduced cells were diluted and seeded on 96-well plates for mini pool generation. In the process of seeding, the cells were grown under selection pressure and 40 mini pools were isolated. The cells were expanded and PIOD3 expression was determined in cell lysates by Western Blot to verify efficient knock-down of Plod3. lysates from $1\times10^6$ lentiviral transduced Expi293F mini pools were loaded onto a SOS-PAGE. Western Blot analysis of successful knock-down was performed using an anti-PIOD3 antibody (Thermo Fisher PAS-48435) and a secondary anti-rabbit HRP antibody. PIOD3 has a theoretical molecular weight of 84 kDa. Clone #4, #18 and #20 showed efficient Plod3 knock-down and were therefore used for further expansion and experiments. Clone 18 was lost due to drop in viability, Clones 4 and 20 have been selected for further production and glycan analysis is underway.

Sequence listing:

SEQ ID NO: 1 AGFKGEQGPKG

SEQ ID NO: 2 AGFKGEQGPXG

SEQ ID NO: 3 AGFKGEX$_2$GPKG

SEQ ID NO: 4 AGFKGX$_3$QGPKG

SEQ ID NO: 5 AGFKX$_4$EQGPKG

SEQ ID NO: 6 AGFKGEX$_2$GPX$_1$G

SEQ ID NO: 7 AGFKGX$_3$QGPX$_1$G

SEQ ID NO: 8 AGFKX$_4$EQGPX$_1$G

SEQ ID NO: 9 AGFKGEQGPRG

SEQ ID NO: 10 AGFKGEQGPKGEP

SEQ ID NO: 11 AGFKGEQGPX$_1$GEP

SEQ ID NO: 12 AGFKGEQGPRGEP

SEQ ID NO: 13 GIAGFKGEQGPKGEP

SEQ ID NO: 14 GIAGFKGEQGPX$_1$GEP

SEQ ID NO: 15 GIAGFKGEQGPRGEP

SEQ ID NO: 16 DR4 construct α-chain

-continued

SEQ ID NO: 17 DR4 construct β-chain with hCI1259-273 peptide

SEQ ID NO: 18 Minimal DR4 construct α-chain

SEQ ID NO: 19 Minimal DR4 construct β-chain with hCI1259-273 peptide

SEQ ID NO: 20 DR4 construct β-chain with hCLIPmut

SEQ ID NO: 21 Aq construct α-chain

SEQ ID NO: 22 Aq construct β-chain with rat CI1259-273 peptide

SEQ ID NO: 23 Aq construct β-chain with rat CI1259-273 peptide without His-tag

SEQ ID NO: 24 Aq construct β-chain with mCLIP peptide

SEQ ID NO: 25 Aq construct β-chain with mCLIP peptide without His-tag

SEQ ID NO: 26 cFos domain

SEQ ID NO: 27 cJune domain

SEQ ID NO: 28 modified human CLIP-peptide

SEQ ID NO: 29 rat CII-peptide 259-273

SEQ ID NO: 30 streptavidin-tag

SEQ ID NO: 31 EKRIWFPYRRF

SEQ ID NO: 32 YKTNFRRYYRF

SEQ ID NO: 33 VLIRHFRKRYY

SEQ ID NO: 34 SAWSHPQFEKGIAGFKGEQGPKGEPSGGGS

The invention claimed is:

1. A composition comprising recombinant MHC II/CII peptide complexes comprising
   (a) an extracellular region of an MHC class II alpha chain comprising at least one alpha 1 domain;
   (b) an extracellular region of an MHC class II beta chain comprising at least one beta 1 domain; and
   (c) a collagen II peptide (CII peptide) fused to the N-terminus of the MHC class II alpha chain or the MHC class II beta chain by a linker peptide;
   wherein the CII peptide comprises the amino acid sequence selected from the group consisting of AGFKGEQGPKG (SEQ ID NO: 1) and AGFKGEQGPXG (SEQ ID NO: 2), wherein X is not lysine, and
   the CII peptide is post-translationally modified, wherein the first lysine residue of the CII peptide is O-glycosylated hydroxylysine (Hyl); and
   wherein the at least one alpha 1 domain is from DRA*0101 and the at least one beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303.

2. The composition of claim 1, wherein
   (a) the first lysine residue is galactosyl-hydroxylysine;
   (b) the CII peptide is fused to the N-terminus of the beta 1 domain by a linker peptide;
   (c) the at least one alpha 1 domain is from DRA*0101 and the at least one beta 1 domain is from DRB1*0401;
   (d) the CII peptide comprises the amino acid sequence of AGFKGEQGPKG (SEQ ID NO: 1);
   (e) the CII peptide comprises only the first lysine residue and any further K is mutated: and/or
   (f) the CII peptide comprises only the first lysine residue and any further K is mutated to R.

3. The composition of claim 1, wherein
   (a) the extracellular region of the MHC class II alpha chain comprising the at least an one alpha 1 domain;
   (b) the extracellular region of the MHC class II beta chain comprising the at least one beta 1 domain; and
   (c) the collagen II peptide (CII peptide) fused to the N-terminus of the MHC class II alpha chain or the MHC class II beta chain by a linker peptide;
   are expressed as a single fusion polypeptide.

4. The composition of claim 1 comprising
   (a) a first polypeptide comprising the extracellular region of the MHC class II alpha chain comprising the at least an one alpha 1 domain;
   (b) a second polypeptide comprising the extracellular region of the MHC class II beta chain comprising the at least one beta 1 domain; and
   (c) the collagen II peptide (CII peptide) fused to the N-terminus of the MHC class II alpha chain or the MHC class II beta chain by a linker peptide.

5. The composition of claim 4, wherein the MHC class II alpha chain is fused at its C-terminal end to a first leucine zipper and the MHC class II beta chain is fused at its C-terminal end to a second leucine zipper, wherein the first and second leucine zippers form together
   (a) an acidic and a basic leucine zipper; or
   (b) a jun-fos leucine zipper.

6. A method for producing a MHC II/CII peptide complex comprising a post-translationally modified CII peptide comprising
   (a) transfecting a mammalian cell with
      (i) a polynucleotide encoding an extracellular region of the MHC II alpha chain comprising at least an one alpha 1 domain;
      (ii) a polynucleotide encoding an extracellular region of the MHC II beta chain comprising at least one beta 1 domain; and
      (iii) a polynucleotide encoding a collagen II peptide (CII peptide) fused to the N-terminus of the MHC class II alpha chain or the MHC class II beta chain by a linker peptide, wherein the CII peptide comprises the amino acid sequence selected from the group consisting of AGFKGEQGPKG (SEQ ID NO: 1) and AGFKGEQGPXG (SEQ ID NO: 2), wherein X is not lysine;
   (b) cultivating the mammalian cell under conditions suitable to produce the MHC II/CII peptide complex; and
   (c) harvesting a cell supernatant and optionally cells comprising the MHC II/CII peptide complex comprising a post-translationally modified CII peptide, wherein the first lysine residue of the CII peptide is O-glycosylated hydroxylysine (Hyl) and wherein the at least one alpha 1 domain is from DRA*0101 and the at least one beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402, and DRB1*1303;
   optionally further comprising a step of analysing the post-translational modification of the CII peptide of the MHC II/CII peptide complex.

7. The method of claim 6, wherein
   (a) the first lysine residue is galactosyl-hydroxylysine;
   (b) the at least the alpha 1 domain is from DRA*0101 and the at least one beta 1 domain is from DRB1*0401;
   (c) the CII peptide comprises the amino acid sequence of AGFKGEQGPKG (SEQ ID NO: 1);
   (d) the CII peptide comprises only the first lysine residue and any further K is mutated; and/or
   (e) the CII peptide comprises only the first lysine residue and any further K is mutated to R.

8. The method of claim 6, wherein the mammalian cell
   (a) comprises enzymes to post-translationally modify lysine residues in collagen, comprising hydroxylating lysine to hydroxylysine (Hyl) and galactosylating Hyl to galactosylhydroxylysine (Gal-Hyl);

(b) comprises a lysylhydroxylase and a collagen galactosyltransferase;

(c) comprises lysylhydroxylase 1 (LH1) and/or lysylhydroxylase 2 (LH2) and collagen galactosyltransferase GLT25D1 and/or GLT25D2; or (d) comprises LH1 and/or LH2 and GLT25D1.

9. The method of claim 8, wherein the mammalian cell is (a) a kidney cell, a fibroblast cell or an osteoblast cell (b) a HEK 293 cell line; or (c) a genetically engineered cell recombinantly expressing a lysylhydroxylase and a collagen galactosyltransferase.

10. The method of claim 6, wherein the mammalian cell (a) lacks galactosylhydroxylysyl glucosyltransferase activity;

(b) lacks the multifunctional enzyme LH3; or (c) comprises a mutant LH3 enzyme lacking galactosylhydroxylysyl glucosyltransferase activity.

11. The method of claim 6, comprising (a) a first polynucleotide encoding the extracellular region of the MHC class II alpha chain comprising the at least one alpha 1 domain;

(b) a second polynucleotide encoding the extracellular region of the MHC class II beta chain comprising the at least one beta 1 domain; and (c) a polynucleotide encoding the collagen II peptide (CII peptide) fused to the N-terminus of the MHC class II alpha chain or the MHC class II beta chain by a linker peptide, wherein the MHC class II alpha chain is fused at its C-terminal end to a first leucine zipper and the MHC class II beta chain is fused at its C-terminal end to a second leucine zipper, wherein the first and second leucine zippers form together (a) an acidic and a basic leucine zipper; or (b) a jun-fos leucine zipper.

12. A recombinant MHC II/CII peptide complex comprising a post-translationally modified CII peptide, wherein the first lysine residue of the CII peptide is O-glycosylated hydroxylysine (Hyl), obtained by a method for producing a MHC II/CII peptide complex comprising a post-translationally modified CII peptide comprising (a) transfecting a mammalian cell with (i) a polynucleotide encoding an extracellular region of the MHC II alpha chain comprising at least one alpha 1 domain;

(ii) a polynucleotide encoding an extracellular region of the MHC II beta chain comprising at least one beta 1 domain; and (iii) a polynucleotide encoding a collagen II peptide (CII peptide) fused to the N-terminus of the MHC class II alpha chain or the MHC class II beta chain by a linker peptide, wherein the CII peptide comprises the amino acid sequence selected from the group consisting of AGFKGEQGPKG (SEQ ID NO: 1) and AGFKGEQGPXG (SEQ ID NO: 2), wherein X is not lysine;

(b) cultivating the mammalian cell under conditions suitable to produce the MHC II/CII peptide complex; and (c) harvesting a cell supernatant and optionally cells comprising the MHC II/CII peptide complex comprising a post-translationally modified CII peptide, wherein the first lysine residue of the CII peptide is O-glycosylated (Hyl) and wherein the at least one alpha 1 domain is from DRA*0101 and the at least one beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402, and DRB1*1303.

13. A method for treating rheumatoid arthritis in a human subject in need thereof comprising administering the composition of claim 1.

14. A MHC II/CII peptide complex tetramer comprising the recombinant MHC II/CII peptide complex(es) of the composition according to claim 1.

15. A method for treating rheumatoid arthritis in a human subject in need thereof comprising administering to said subject the recombinant MCH II/CII peptide complex according to claim 12.

16. A MHC II/CII peptide complex tetramer comprising the recombinant MHC II/CII peptide complex comprising a post-translationally modified CII peptide according to claim 12.

17. The composition of claim 1, wherein the collagen II peptide (CII peptide) is fused to the N-terminus of the MHC class II beta chain by a linker peptide.

18. The composition of claim 12, wherein the method further comprises a step of analysing the post-translational modification of the CII peptide of the MHC II/CII peptide complex.

* * * * *

SEQUENCE LISTING

```
<160> NUMBER OF SEQ ID NOS: 36

<210> SEQ ID NO 1
<211> LENGTH: 11
<212> TYPE: PRT
<213> ORGANISM: Homo sapiens
<220> FEATURE:
<221> NAME/KEY: UNSURE
<222> LOCATION: (1)..(11)
<223> OTHER INFORMATION: CII peptide 261-271

<400> SEQUENCE: 1

Ala Gly Phe Lys Gly Glu Gln Gly Pro Lys Gly
1               5                   10


<210> SEQ ID NO 2
<211> LENGTH: 11
<212> TYPE: PRT
<213> ORGANISM: Homo sapiens
<220> FEATURE:
<221> NAME/KEY: UNSURE
<222> LOCATION: (1)..(11)
<223> OTHER INFORMATION: CII peptide 261-271
<220> FEATURE:
<221> NAME/KEY: VARIANT
<222> LOCATION: (10)..(10)
<223> OTHER INFORMATION: Xaa = any proteinogenic amino acids except Lys;
      preferably Xaa = Arg, Ala, Gly or Gln

<400> SEQUENCE: 2

Ala Gly Phe Lys Gly Glu Gln Gly Pro Xaa Gly
1               5                   10


<210> SEQ ID NO 3
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (7)..(7)
<223> OTHER INFORMATION: Xaa = any proteinogenic amion acid except Gln;
      preferably Xaa = Ala, Arg, His or Gly

<400> SEQUENCE: 3

Ala Gly Phe Lys Gly Glu Xaa Gly Pro Lys Gly
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (6)..(6)
<223> OTHER INFORMATION: Xaa = any proteinogenic amino acid except Glu, preferably Xaa = Ala, Asp, Gln or Gly

<400> SEQUENCE: 4

Ala Gly Phe Lys Gly Xaa Gln Gly Pro Lys Gly
1 5 10

<210> SEQ ID NO 5
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (5)..(5)
<223> OTHER INFORMATION: Xaa = any proteinogenic amino acid expect Gly; preferably Xaa = Ala, Ser, Val or Leu

<400> SEQUENCE: 5

Ala Gly Phe Lys Xaa Glu Gln Gly Pro Lys Gly
1 5 10

<210> SEQ ID NO 6
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (7)..(7)
<223> OTHER INFORMATION: Xaa = any proteinogenic amino acid expect Gln; preferably Xaa = Ala, Arg, His or Gly
<220> FEATURE:
<221> NAME/KEY: VARIANT
<222> LOCATION: (10)..(10)
<223> OTHER INFORMATION: Xaa = any proteinogenic amino acid except Lys; preferably Xaa = Arg, Ala, Gly or Gln

<400> SEQUENCE: 6

Ala Gly Phe Lys Gly Glu Xaa Gly Pro Xaa Gly
1 5 10

<210> SEQ ID NO 7
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (6)..(6)
<223> OTHER INFORMATION: Xaa = any proteinogenic amino acid except Glu; preferably Xaa = Ala, Asp, Gln or Gly
<220> FEATURE:
<221> NAME/KEY: VARIANT
<222> LOCATION: (10)..(10)
<223> OTHER INFORMATION: Xaa = any proteinogenic amino acid expect Lys, preferably Xaa = Arg, Ala, Gly or Gln

<400> SEQUENCE: 7

Ala Gly Phe Lys Gly Xaa Gln Gly Pro Xaa Gly
1 5 10

<210> SEQ ID NO 8
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: VARIANT
<222> LOCATION: (5)..(5)
<223> OTHER INFORMATION: Xaa = any proteinogenic amino acid except Gly; preferably Xaa = Ala, Ser, Val or Leu
<220> FEATURE:
<221> NAME/KEY: VARIANT
<222> LOCATION: (10)..(10)
<223> OTHER INFORMATION: Xaa = any proteinogenic amino acids except Lys; preferably Xaa = Arg, Ala, Gly or Gln

<400> SEQUENCE: 8

Ala Gly Phe Lys Xaa Glu Gln Gly Pro Xaa Gly
1 5 10

<210> SEQ ID NO 9
<211> LENGTH: 11
<212> TYPE: PRT
<213> ORGANISM: Artificial Sequence
<220> FEATURE:
<223> OTHER INFORMATION: CII peptide 261-271

<400> SEQUENCE: 9

Ala Gly Phe Lys Gly Glu Gln Gly Pro Arg Gly
1 5 10

<210> SEQ ID NO 10
<211> LENGTH: 13
<212> TYPE: PRT
<213> ORGANISM: Homo sapiens
<220> FEATURE:
<221> NAME/KEY: UNSURE
<222> LOCATION: (1)..(13)
<223> OTHER INFORMATION: CII peptide 261-273

<400> SEQUENCE: 10

Ala Gly Phe Lys Gly Glu Gln Gly Pro Lys Gly Glu Pro
1 5 10

<210> SEQ ID NO 11
<211> LENGTH: 13
<212> TYPE: PRT
<213> ORGANISM: Artificial Sequence
<220> FEATURE:
<223> OTHER INFORMATION: CII peptide 261-273
<220> FEATURE:
<221> NAME/KEY: VARIANT
<222> LOCATION: (10)..(10)
<223> OTHER INFORMATION: Xaa = any proteinogenic amino acid except Lys; preferably Xaa = Arg, Ala, Gly or Gln

<400> SEQUENCE: 11

Ala Gly Phe Lys Gly Glu Gln Gly Pro Xaa Gly Glu Pro
1 5 10

<210> SEQ ID NO 12
<211> LENGTH: 13
<212> TYPE: PRT
<213> ORGANISM: Artificial Sequence
<220> FEATURE:

<223> OTHER INFORMATION: CII peptide 261-273

<400> SEQUENCE: 12

Ala Gly Phe Lys Gly Glu Gln Gly Pro Arg Gly Glu Pro
1 5 10

<210> SEQ ID NO 13
<211> LENGTH: 15
<212> TYPE: PRT
<213> ORGANISM: Homo sapiens
<220> FEATURE:
<221> NAME/KEY: UNSURE
<222> LOCATION: (1)..(15)
<223> OTHER INFORMATION: CII peptide 259-273

<400> SEQUENCE: 13

Gly Ile Ala Gly Phe Lys Gly Glu Gln Gly Pro Lys Gly Glu Pro
1 5 10 15

<210> SEQ ID NO 14
<211> LENGTH: 15
<212> TYPE: PRT
<213> ORGANISM: Artificial sequence
<220> FEATURE:
<223> OTHER INFORMATION: CII peptide 259-273
<220> FEATURE:
<221> NAME/KEY: VARIANT
<222> LOCATION: (12)..(12)
<223> OTHER INFORMATION: Xaa = any proteinogenic amino acid; preferably Xaa = Arg, Ala, Gly or Gln

<400> SEQUENCE: 14

Gly Ile Ala Gly Phe Lys Gly Glu Gln Gly Pro Xaa Gly Glu Pro
1 5 10 15

<210> SEQ ID NO 15
<211> LENGTH: 15
<212> TYPE: PRT
<213> ORGANISM: Artificial sequence
<220> FEATURE:
<223> OTHER INFORMATION: CII peptide 259-273

<400> SEQUENCE: 15

Gly Ile Ala Gly Phe Lys Gly Glu Gln Gly Pro Arg Gly Glu Pro
1 5 10 15

<210> SEQ ID NO 16
<211> LENGTH: 274
<212> TYPE: PRT
<213> ORGANISM: Artificial Sequence
<220> FEATURE:
<223> OTHER INFORMATION: DR4 construct alpha-chain

<400> SEQUENCE: 16

Met Lys Leu Cys Ile Leu Leu Ala Trp Ala Phe Val Gly Leu Ser Leu
1 5 10 15

Gly Ile Lys Glu Glu His Val Ile Ile Gln Ala Glu Phe Tyr Leu Asn
20 25 30

Pro Asp Gln Ser Gly Glu Phe Met Phe Asp Phe Asp Gly Asp Glu Ile
35 40 45

Phe His Val Asp Met Ala Lys Lys Glu Thr Val Trp Arg Leu Glu Glu
50 55 60

Phe Gly Arg Phe Ala Ser Phe Glu Ala Gln Gly Ala Leu Ala Asn Ile
65 70 75 80

Ala Val Asp Lys Ala Asn Leu Glu Ile Met Thr Lys Arg Ser Asn Tyr

```
                85                  90                  95

Thr Pro Ile Thr Asn Val Pro Pro Glu Val Thr Val Leu Thr Asn Ser
            100                 105                 110

Pro Val Glu Leu Arg Glu Pro Asn Val Leu Ile Cys Phe Ile Asp Lys
        115                 120                 125

Phe Thr Pro Pro Val Val Asn Val Thr Trp Leu Arg Asn Gly Lys Pro
    130                 135                 140

Val Thr Thr Gly Val Ser Glu Thr Val Phe Leu Pro Arg Glu Asp His
145                 150                 155                 160

Leu Phe Arg Lys Phe His Tyr Leu Pro Phe Leu Pro Ser Thr Glu Asp
                165                 170                 175

Val Tyr Asp Cys Arg Val Glu His Trp Gly Leu Asp Glu Pro Leu Leu
            180                 185                 190

Lys His Trp Glu Phe Asp Ala Ser Gly Gly Gly Glu Asn Leu Tyr Phe
        195                 200                 205

Gln Gly Gly Gly Gly Ser Leu Thr Asp Thr Leu Gln Ala Glu Thr Asp
    210                 215                 220

Gln Leu Glu Asp Glu Lys Ser Ala Leu Gln Thr Glu Ile Ala Asn Leu
225                 230                 235                 240

Leu Lys Glu Lys Glu Lys Leu Glu Phe Ile Leu Ala Ala His Gly Gly
                245                 250                 255

Gly Gly Ser Gly Leu Asn Asp Ile Phe Glu Ala Gln Lys Ile Glu Trp
            260                 265                 270

His Glu


<210> SEQ ID NO 17
<211> LENGTH: 310
<212> TYPE: PRT
<213> ORGANISM: Artificial Sequence
<220> FEATURE:
<223> OTHER INFORMATION: DR4 construct beta-chain with hCII259-273
      peptide

<400> SEQUENCE: 17

Met Lys Leu Cys Ile Leu Leu Ala Trp Ala Phe Val Gly Leu Ser Leu
1               5                   10                  15

Gly Ser Ala Trp Ser His Pro Gln Phe Glu Lys Gly Ile Ala Gly Phe
            20                  25                  30

Lys Gly Glu Gln Gly Pro Lys Gly Glu Pro Ser Gly Gly Gly Ser Leu
        35                  40                  45

Val Pro Arg Gly Ser Gly Gly Gly Gly Ser Gly Asp Thr Arg Pro Arg
    50                  55                  60

Phe Leu Glu Gln Val Lys His Glu Cys His Phe Phe Asn Gly Thr Glu
65                  70                  75                  80

Arg Val Arg Phe Leu Asp Arg Tyr Phe Tyr His Gln Glu Glu Tyr Val
                85                  90                  95

Arg Phe Asp Ser Asp Val Gly Glu Tyr Arg Ala Val Thr Glu Leu Gly
            100                 105                 110

Arg Pro Asp Ala Glu Tyr Trp Asn Ser Gln Lys Asp Leu Leu Glu Gln
        115                 120                 125

Lys Arg Ala Ala Val Asp Thr Tyr Cys Arg His Asn Tyr Gly Val Gly
    130                 135                 140

Glu Ser Phe Thr Val Gln Arg Arg Val Tyr Pro Glu Val Thr Val Tyr
145                 150                 155                 160

Pro Ala Lys Thr Gln Pro Leu Gln His His Asn Leu Leu Val Cys Ser
```

```
                165                 170                 175

Val Asn Gly Phe Tyr Pro Gly Ser Ile Glu Val Arg Trp Phe Arg Asn
            180                 185                 190

Gly Gln Glu Glu Lys Thr Gly Val Val Ser Thr Gly Leu Ile Gln Asn
        195                 200                 205

Gly Asp Trp Thr Phe Gln Thr Leu Val Met Leu Glu Thr Val Pro Arg
    210                 215                 220

Ser Gly Glu Val Tyr Thr Cys Gln Val Glu His Pro Ser Leu Thr Ser
225                 230                 235                 240

Pro Leu Thr Val Glu Trp Arg Ala Arg Ser Gly Gly Gly Glu Asn Leu
                245                 250                 255

Tyr Phe Gln Gly Gly Gly Gly Ser Arg Ile Ala Arg Leu Glu Glu Lys
            260                 265                 270

Val Lys Thr Leu Lys Ala Gln Asn Ser Glu Leu Ala Ser Thr Ala Asn
        275                 280                 285

Met Leu Arg Glu Gln Val Ala Gln Leu Lys Gln Lys Val Met Asn His
    290                 295                 300

His His His His His His
305                 310


<210> SEQ ID NO 18
<211> LENGTH: 247
<212> TYPE: PRT
<213> ORGANISM: Artificial Sequence
<220> FEATURE:
<223> OTHER INFORMATION: Minimal DR4 construct alpha-chain

<400> SEQUENCE: 18

Met Lys Leu Cys Ile Leu Leu Ala Trp Ala Phe Val Gly Leu Ser Leu
1               5                   10                  15

Gly Ile Lys Glu Glu His Val Ile Ile Gln Ala Glu Phe Tyr Leu Asn
            20                  25                  30

Pro Asp Gln Ser Gly Glu Phe Met Phe Asp Phe Asp Gly Asp Glu Ile
        35                  40                  45

Phe His Val Asp Met Ala Lys Lys Glu Thr Val Trp Arg Leu Glu Glu
    50                  55                  60

Phe Gly Arg Phe Ala Ser Phe Glu Ala Gln Gly Ala Leu Ala Asn Ile
65                  70                  75                  80

Ala Val Asp Lys Ala Asn Leu Glu Ile Met Thr Lys Arg Ser Asn Tyr
                85                  90                  95

Thr Pro Ile Thr Asn Val Pro Pro Glu Val Thr Val Leu Thr Asn Ser
            100                 105                 110

Pro Val Glu Leu Arg Glu Pro Asn Val Leu Ile Cys Phe Ile Asp Lys
        115                 120                 125

Phe Thr Pro Pro Val Val Asn Val Thr Trp Leu Arg Asn Gly Lys Pro
    130                 135                 140

Val Thr Thr Gly Val Ser Glu Thr Val Phe Leu Pro Arg Glu Asp His
145                 150                 155                 160

Leu Phe Arg Lys Phe His Tyr Leu Pro Phe Leu Pro Ser Thr Glu Asp
                165                 170                 175

Val Tyr Asp Cys Arg Val Glu His Trp Gly Leu Asp Glu Pro Leu Leu
            180                 185                 190

Lys His Trp Glu Phe Asp Ala Ser Gly Gly Gly Gly Gly Gly Ser Leu
        195                 200                 205

Thr Asp Thr Leu Gln Ala Glu Thr Asp Gln Leu Glu Asp Glu Lys Ser
```

```
    210                 215                 220

Ala Leu Gln Thr Glu Ile Ala Asn Leu Leu Lys Glu Lys Glu Lys Leu
225                 230                 235                 240

Glu Phe Ile Leu Ala Ala His
                245


<210> SEQ ID NO 19
<211> LENGTH: 286
<212> TYPE: PRT
<213> ORGANISM: Artificial Sequence
<220> FEATURE:
<223> OTHER INFORMATION: Minimal DR4 construct beta-chain with hCII259-
      273 peptide

<400> SEQUENCE: 19

Met Lys Leu Cys Ile Leu Leu Ala Trp Ala Phe Val Gly Leu Ser Leu
1               5                   10                  15

Gly Gly Ile Ala Gly Phe Lys Gly Glu Gln Gly Pro Lys Gly Glu Pro
            20                  25                  30

Ser Gly Gly Gly Ser Gly Gly Gly Gly Ser Gly Asp Thr Arg Pro Arg
        35                  40                  45

Phe Leu Glu Gln Val Lys His Glu Cys His Phe Phe Asn Gly Thr Glu
    50                  55                  60

Arg Val Arg Phe Leu Asp Arg Tyr Phe Tyr His Gln Glu Glu Tyr Val
65                  70                  75                  80

Arg Phe Asp Ser Asp Val Gly Glu Tyr Arg Ala Val Thr Glu Leu Gly
                85                  90                  95

Arg Pro Asp Ala Glu Tyr Trp Asn Ser Gln Lys Asp Leu Leu Glu Gln
            100                 105                 110

Lys Arg Ala Ala Val Asp Thr Tyr Cys Arg His Asn Tyr Gly Val Gly
        115                 120                 125

Glu Ser Phe Thr Val Gln Arg Arg Val Tyr Pro Glu Val Thr Val Tyr
    130                 135                 140

Pro Ala Lys Thr Gln Pro Leu Gln His His Asn Leu Leu Val Cys Ser
145                 150                 155                 160

Val Asn Gly Phe Tyr Pro Gly Ser Ile Glu Val Arg Trp Phe Arg Asn
                165                 170                 175

Gly Gln Glu Glu Lys Thr Gly Trp Ser Thr Gly Leu Ile Gln Asn Gly
            180                 185                 190

Asp Trp Thr Phe Gln Thr Leu Val Met Leu Glu Thr Val Pro Arg Ser
        195                 200                 205

Gly Glu Val Tyr Thr Cys Gln Val Glu His Pro Ser Leu Thr Ser Pro
    210                 215                 220

Leu Thr Val Glu Trp Arg Ala Arg Ser Gly Gly Gly Gly Gly Gly Ser
225                 230                 235                 240

Arg Ile Ala Arg Leu Glu Glu Lys Val Lys Thr Leu Lys Ala Gln Asn
                245                 250                 255

Ser Glu Leu Ala Ser Thr Ala Asn Met Leu Arg Glu Gln Val Ala Gln
            260                 265                 270

Leu Lys Gln Lys Val Met Asn His His His His His His His
        275                 280                 285


<210> SEQ ID NO 20
<211> LENGTH: 310
<212> TYPE: PRT
<213> ORGANISM: Artificial Sequence
<220> FEATURE:
```

<223> OTHER INFORMATION: DR4 construct beta-chain with hCLIPmu

<400> SEQUENCE: 20

Met Lys Leu Cys Ile Leu Leu Ala Trp Ala Phe Val Gly Leu Ser Leu
1 5 10 15

Gly Ser Ala Trp Ser His Pro Gln Phe Glu Lys Pro Val Ser Lys Ala
20 25 30

Arg Met Ala Thr Gly Ala Leu Ala Gln Ala Ser Gly Gly Gly Ser Leu
35 40 45

Val Pro Arg Gly Ser Gly Gly Gly Gly Ser Gly Asp Thr Arg Pro Arg
50 55 60

Phe Leu Glu Gln Val Lys His Glu Cys His Phe Phe Asn Gly Thr Glu
65 70 75 80

Arg Val Arg Phe Leu Asp Arg Tyr Phe Tyr His Gln Glu Glu Tyr Val
85 90 95

Arg Phe Asp Ser Asp Val Gly Glu Tyr Arg Ala Val Thr Glu Leu Gly
100 105 110

Arg Pro Asp Ala Glu Tyr Trp Asn Ser Gln Lys Asp Leu Leu Glu Gln
115 120 125

Lys Arg Ala Ala Val Asp Thr Tyr Cys Arg His Asn Tyr Gly Val Gly
130 135 140

Glu Ser Phe Thr Val Gln Arg Arg Val Tyr Pro Glu Val Thr Val Tyr
145 150 155 160

Pro Ala Lys Thr Gln Pro Leu Gln His His Asn Leu Leu Val Cys Ser
165 170 175

Val Asn Gly Phe Tyr Pro Gly Ser Ile Glu Val Arg Trp Phe Arg Asn
180 185 190

Gly Gln Glu Glu Lys Thr Gly Val Val Ser Thr Gly Leu Ile Gln Asn
195 200 205

Gly Asp Trp Thr Phe Gln Thr Leu Val Met Leu Glu Thr Val Pro Arg
210 215 220

Ser Gly Glu Val Tyr Thr Cys Gln Val Glu His Pro Ser Leu Thr Ser
225 230 235 240

Pro Leu Thr Val Glu Trp Arg Ala Arg Ser Gly Gly Gly Glu Asn Leu
245 250 255

Tyr Phe Gln Gly Gly Gly Gly Ser Arg Ile Ala Arg Leu Glu Glu Lys
260 265 270

Val Lys Thr Leu Lys Ala Gln Asn Ser Glu Leu Ala Ser Thr Ala Asn
275 280 285

Met Leu Arg Glu Gln Val Ala Gln Leu Lys Gln Lys Val Met Asn His
290 295 300

His His His His His His
305 310

<210> SEQ ID NO 21
<211> LENGTH: 289
<212> TYPE: PRT
<213> ORGANISM: Artificial Sequence
<220> FEATURE:
<223> OTHER INFORMATION: Aq construct alpha-chain

<400> SEQUENCE: 21

Met Lys Leu Cys Ile Leu Leu Ala Trp Ala Phe Val Gly Leu Ser Leu
1 5 10 15

Gly Glu Asp Asp Ile Glu Ala Asp His Val Gly Phe Tyr Gly Ile Val
20 25 30

```
Val Tyr Gln Ser Pro Gly Asp Ile Gly Gln Tyr Thr His Glu Phe Asp
        35                  40                  45

Gly Asp Glu Trp Phe Tyr Val Asp Leu Asp Lys Lys Glu Thr Val Trp
    50                  55                  60

Met Leu Pro Glu Phe Gly Gln Leu Thr Ser Phe Asp Pro Gln Gly Gly
65                  70                  75                  80

Leu Gln Asn Ile Ala Thr Gly Lys His Asn Leu Gly Gly Trp Thr Lys
                85                  90                  95

Arg Ser Asn Phe Thr Pro Ala Thr Asn Glu Ala Pro Gln Ala Thr Val
            100                 105                 110

Phe Pro Lys Ser Pro Val Leu Leu Gly Gln Pro Asn Thr Leu Ile Cys
        115                 120                 125

Phe Val Asp Asn Ile Phe Pro Pro Val Ile Asn Ile Thr Trp Leu Arg
    130                 135                 140

Asn Ser Lys Ser Val Thr Asp Gly Val Tyr Glu Thr Ser Phe Leu Val
145                 150                 155                 160

Asn Arg Asp His Ser Phe His Lys Leu Ser Tyr Leu Thr Phe Ile Pro
                165                 170                 175

Ser Asp Asp Asp Ile Tyr Asp Cys Lys Val Glu His Trp Gly Leu Asp
            180                 185                 190

Glu Pro Val Leu Lys His Trp Glu Pro Glu Ile Pro Ala Thr Met Ser
        195                 200                 205

Glu Leu Thr Glu Thr Val Ser Gly Gly Gly Glu Asn Leu Tyr Phe Gln
    210                 215                 220

Gly Gly Gly Gly Ser Leu Thr Asp Thr Leu Gln Ala Glu Thr Asp Gln
225                 230                 235                 240

Leu Glu Asp Glu Lys Ser Ala Leu Gln Thr Glu Ile Ala Asn Leu Leu
                245                 250                 255

Lys Glu Lys Glu Lys Leu Glu Phe Ile Leu Ala Ala His Gly Gly Gly
            260                 265                 270

Gly Ser Gly Leu Asn Asp Ile Phe Glu Ala Gln Lys Ile Glu Trp His
        275                 280                 285

Glu


<210> SEQ ID NO 22
<211> LENGTH: 314
<212> TYPE: PRT
<213> ORGANISM: Artificial Sequence
<220> FEATURE:
<223> OTHER INFORMATION: Aq construct beta-chain with rat CII259-273
      peptide

<400> SEQUENCE: 22

Met Lys Leu Cys Ile Leu Leu Ala Trp Ala Phe Val Gly Leu Ser Leu
1               5                   10                  15

Gly Ser Ala Trp Ser His Pro Gln Phe Glu Lys Gly Ile Ala Gly Phe
            20                  25                  30

Lys Gly Glu Gln Gly Pro Lys Gly Glu Thr Ser Gly Gly Gly Ser Leu
        35                  40                  45

Val Pro Arg Gly Ser Gly Gly Gly Gly Ser Glu Arg His Phe Val Ala
    50                  55                  60

Gln Leu Lys Gly Glu Cys Tyr Phe Thr Asn Gly Thr Gln Arg Ile Arg
65                  70                  75                  80

Ser Val Asn Arg Tyr Ile Tyr Asn Arg Glu Glu Trp Val Arg Phe Asp
                85                  90                  95
```

Ser Asp Val Gly Glu Tyr Arg Ala Val Thr Glu Leu Gly Arg Pro Asp
100 105 110

Ala Glu Tyr Trp Asn Ser Gln Pro Glu Ile Leu Glu Arg Thr Arg Ala
115 120 125

Glu Val Asp Thr Val Cys Arg His Asn Tyr Glu Gly Val Glu Thr His
130 135 140

Thr Ser Leu Arg Arg Leu Glu Gln Pro Asn Val Ala Ile Ser Leu Ser
145 150 155 160

Arg Thr Glu Ala Leu Asn His His Asn Thr Leu Val Cys Ser Val Thr
165 170 175

Asp Phe Tyr Pro Ala Lys Ile Lys Val Arg Trp Phe Arg Asn Gly Gln
180 185 190

Glu Glu Thr Val Gly Val Ser Ser Thr Gln Leu Ile Arg Asn Gly Asp
195 200 205

Thr Phe Gln Val Leu Val Met Leu Glu Met Thr Pro His Gln Gly Glu
210 215 220

Val Tyr Thr Cys His Val Glu His Pro Ser Leu Lys Ser Pro Ile Thr
225 230 235 240

Val Glu Trp Arg Ala Gln Ser Glu Ser Ala Arg Ser Lys Ser Gly Gly
245 250 255

Gly Glu Asn Leu Tyr Phe Gln Gly Gly Gly Gly Ser Arg Ile Ala Arg
260 265 270

Leu Glu Glu Lys Val Lys Thr Leu Lys Ala Gln Asn Ser Glu Leu Ala
275 280 285

Ser Thr Ala Asn Met Leu Arg Glu Gln Val Ala Gln Leu Lys Gln Lys
290 295 300

Val Met Asn His His His His His His His
305 310

<210> SEQ ID NO 23
<211> LENGTH: 308
<212> TYPE: PRT
<213> ORGANISM: Artificial Sequence
<220> FEATURE:
<223> OTHER INFORMATION: Aq construct beta-chain with rat CII259-273 peptide without His-tag

<400> SEQUENCE: 23

Met Lys Leu Cys Ile Leu Leu Ala Trp Ala Phe Val Gly Leu Ser Leu
1 5 10 15

Gly Ser Ala Trp Ser His Pro Gln Phe Glu Lys Gly Ile Ala Gly Phe
20 25 30

Lys Gly Glu Gln Gly Pro Lys Gly Glu Thr Ser Gly Gly Gly Ser Leu
35 40 45

Val Pro Arg Gly Ser Gly Gly Gly Gly Ser Glu Arg His Phe Val Ala
50 55 60

Gln Leu Lys Gly Glu Cys Tyr Phe Thr Asn Gly Thr Gln Arg Ile Arg
65 70 75 80

Ser Val Asn Arg Tyr Ile Tyr Asn Arg Glu Glu Trp Val Arg Phe Asp
85 90 95

Ser Asp Val Gly Glu Tyr Arg Ala Val Thr Glu Leu Gly Arg Pro Asp
100 105 110

Ala Glu Tyr Trp Asn Ser Gln Pro Glu Ile Leu Glu Arg Thr Arg Ala
115 120 125

Glu Val Asp Thr Val Cys Arg His Asn Tyr Glu Gly Val Glu Thr His

```
    130                 135                 140

Thr Ser Leu Arg Arg Leu Glu Gln Pro Asn Val Ala Ile Ser Leu Ser
145                 150                 155                 160

Arg Thr Glu Ala Leu Asn His His Asn Thr Leu Val Cys Ser Val Thr
                165                 170                 175

Asp Phe Tyr Pro Ala Lys Ile Lys Val Arg Trp Phe Arg Asn Gly Gln
            180                 185                 190

Glu Glu Thr Val Gly Val Ser Ser Thr Gln Leu Ile Arg Asn Gly Asp
        195                 200                 205

Thr Phe Gln Val Leu Val Met Leu Glu Met Thr Pro His Gln Gly Glu
    210                 215                 220

Val Tyr Thr Cys His Val Glu His Pro Ser Leu Lys Ser Pro Ile Thr
225                 230                 235                 240

Val Glu Trp Arg Ala Gln Ser Glu Ser Ala Arg Ser Lys Ser Gly Gly
                245                 250                 255

Gly Glu Asn Leu Tyr Phe Gln Gly Gly Gly Gly Ser Arg Ile Ala Arg
            260                 265                 270

Leu Glu Glu Lys Val Lys Thr Leu Lys Ala Gln Asn Ser Glu Leu Ala
        275                 280                 285

Ser Thr Ala Asn Met Leu Arg Glu Gln Val Ala Gln Leu Lys Gln Lys
    290                 295                 300

Val Met Asn His
305


<210> SEQ ID NO 24
<211> LENGTH: 314
<212> TYPE: PRT
<213> ORGANISM: Artificial Sequence
<220> FEATURE:
<223> OTHER INFORMATION: Aq construct beta-chain with mCLIP peptide

<400> SEQUENCE: 24

Met Lys Leu Cys Ile Leu Leu Ala Trp Ala Phe Val Gly Leu Ser Leu
1               5                   10                  15

Gly Ser Ala Trp Ser His Pro Gln Phe Glu Lys Pro Val Ser Gln Ala
            20                  25                  30

Arg Met Ala Thr Pro Leu Leu Met Arg Pro Ser Gly Gly Gly Ser Leu
        35                  40                  45

Val Pro Arg Gly Ser Gly Gly Gly Gly Ser Glu Arg His Phe Val Ala
    50                  55                  60

Gln Leu Lys Gly Glu Cys Tyr Phe Thr Asn Gly Thr Gln Arg Ile Arg
65                  70                  75                  80

Ser Val Asn Arg Tyr Ile Tyr Asn Arg Glu Glu Trp Val Arg Phe Asp
                85                  90                  95

Ser Asp Val Gly Glu Tyr Arg Ala Val Thr Glu Leu Gly Arg Pro Asp
            100                 105                 110

Ala Glu Tyr Trp Asn Ser Gln Pro Glu Ile Leu Glu Arg Thr Arg Ala
        115                 120                 125

Glu Val Asp Thr Val Cys Arg His Asn Tyr Glu Gly Val Glu Thr His
    130                 135                 140

Thr Ser Leu Arg Arg Leu Glu Gln Pro Asn Val Ala Ile Ser Leu Ser
145                 150                 155                 160

Arg Thr Glu Ala Leu Asn His His Asn Thr Leu Val Cys Ser Val Thr
                165                 170                 175

Asp Phe Tyr Pro Ala Lys Ile Lys Val Arg Trp Phe Arg Asn Gly Gln
```

```
            180                 185                 190

Glu Glu Thr Val Gly Val Ser Ser Thr Gln Leu Ile Arg Asn Gly Asp
        195                 200                 205

Thr Phe Gln Val Leu Val Met Leu Glu Met Thr Pro His Gln Gly Glu
    210                 215                 220

Val Tyr Thr Cys His Val Glu His Pro Ser Leu Lys Ser Pro Ile Thr
225                 230                 235                 240

Val Glu Trp Arg Ala Gln Ser Glu Ser Ala Arg Ser Lys Ser Gly Gly
                245                 250                 255

Gly Glu Asn Leu Tyr Phe Gln Gly Gly Gly Gly Ser Arg Ile Ala Arg
            260                 265                 270

Leu Glu Glu Lys Val Lys Thr Leu Lys Ala Gln Asn Ser Glu Leu Ala
        275                 280                 285

Ser Thr Ala Asn Met Leu Arg Glu Gln Val Ala Gln Leu Lys Gln Lys
    290                 295                 300

Val Met Asn His His His His His His His
305                 310


<210> SEQ ID NO 25
<211> LENGTH: 309
<212> TYPE: PRT
<213> ORGANISM: Artificial Sequence
<220> FEATURE:
<223> OTHER INFORMATION: Aq construct beta-chain with mCLIP peptide
      without His-tag

<400> SEQUENCE: 25

Met Lys Leu Cys Ile Leu Leu Ala Val Val Ala Phe Val Gly Leu Ser
1               5                   10                  15

Leu Gly Ser Ala Trp Ser His Pro Gln Phe Glu Lys Pro Val Ser Gln
            20                  25                  30

Ala Arg Met Ala Thr Pro Leu Leu Met Arg Pro Ser Gly Gly Gly Ser
        35                  40                  45

Leu Val Pro Arg Gly Ser Gly Gly Gly Gly Ser Glu Arg His Phe Val
    50                  55                  60

Ala Gln Leu Lys Gly Glu Cys Tyr Phe Thr Asn Gly Thr Gln Arg Ile
65                  70                  75                  80

Arg Ser Val Asn Arg Tyr Ile Tyr Asn Arg Glu Glu Trp Val Arg Phe
                85                  90                  95

Asp Ser Asp Val Gly Glu Tyr Arg Ala Val Thr Glu Leu Gly Arg Pro
            100                 105                 110

Asp Ala Glu Tyr Trp Asn Ser Gln Pro Glu Ile Leu Glu Arg Thr Arg
        115                 120                 125

Ala Glu Val Asp Thr Val Cys Arg His Asn Tyr Glu Gly Val Glu Thr
    130                 135                 140

His Thr Ser Leu Arg Arg Leu Glu Gln Pro Asn Val Ala Ile Ser Leu
145                 150                 155                 160

Ser Arg Thr Glu Ala Leu Asn His His Asn Thr Leu Val Cys Ser Val
                165                 170                 175

Thr Asp Phe Tyr Pro Ala Lys Ile Lys Val Arg Trp Phe Arg Asn Gly
            180                 185                 190

Gln Glu Glu Thr Val Gly Val Ser Ser Thr Gln Leu Ile Arg Asn Gly
        195                 200                 205

Asp Thr Phe Gln Val Leu Val Met Leu Glu Met Thr Pro His Gln Gly
    210                 215                 220
```

-continued

Glu Val Tyr Thr Cys His Val Glu His Pro Ser Leu Lys Ser Pro Ile
225 230 235 240

Thr Val Glu Trp Arg Ala Gln Ser Glu Ser Ala Arg Ser Lys Ser Gly
245 250 255

Gly Gly Glu Asn Leu Tyr Phe Gln Gly Gly Gly Gly Ser Arg Ile Ala
260 265 270

Arg Leu Glu Glu Lys Val Lys Thr Leu Lys Ala Gln Asn Ser Glu Leu
275 280 285

Ala Ser Thr Ala Asn Met Leu Arg Glu Gln Val Ala Gln Leu Lys Gln
290 295 300

Lys Val Met Asn His
305

<210> SEQ ID NO 26
<211> LENGTH: 40
<212> TYPE: PRT
<213> ORGANISM: Homo sapiens

<400> SEQUENCE: 26

Leu Thr Asp Thr Leu Gln Ala Glu Thr Asp Gln Leu Glu Asp Glu Lys
1 5 10 15

Ser Ala Leu Gln Thr Glu Ile Ala Asn Leu Leu Lys Glu Lys Glu Lys
20 25 30

Leu Glu Phe Ile Leu Ala Ala His
35 40

<210> SEQ ID NO 27
<211> LENGTH: 40
<212> TYPE: PRT
<213> ORGANISM: Homo sapiens

<400> SEQUENCE: 27

Arg Ile Ala Arg Leu Glu Glu Lys Val Lys Thr Leu Lys Ala Gln Asn
1 5 10 15

Ser Glu Leu Ala Ser Thr Ala Asn Met Leu Arg Glu Gln Val Ala Gln
20 25 30

Leu Lys Gln Lys Val Met Asn His
35 40

<210> SEQ ID NO 28
<211> LENGTH: 15
<212> TYPE: PRT
<213> ORGANISM: Homo sapiens

<400> SEQUENCE: 28

Pro Val Ser Lys Ala Arg Met Ala Thr Gly Ala Leu Ala Gln Ala
1 5 10 15

<210> SEQ ID NO 29
<211> LENGTH: 15
<212> TYPE: PRT
<213> ORGANISM: Homo sapiens

<400> SEQUENCE: 29

Gly Ile Ala Gly Phe Lys Gly Glu Gln Gly Pro Lys Gly Glu Thr
1 5 10 15

<210> SEQ ID NO 30
<211> LENGTH: 10
<212> TYPE: PRT
<213> ORGANISM: Artificial Sequence

```
<220> FEATURE:
<223> OTHER INFORMATION: streptavidin-tag

<400> SEQUENCE: 30

Ser Ala Trp Ser His Pro Gln Phe Glu Lys
1               5                   10


<210> SEQ ID NO 31
<211> LENGTH: 11
<212> TYPE: PRT
<213> ORGANISM: Artificial Sequence
<220> FEATURE:
<223> OTHER INFORMATION: Chondroitin-binding peptide

<400> SEQUENCE: 31

Glu Lys Arg Ile Trp Phe Pro Tyr Arg Arg Phe
1               5                   10


<210> SEQ ID NO 32
<211> LENGTH: 11
<212> TYPE: PRT
<213> ORGANISM: Artificial Sequence
<220> FEATURE:
<223> OTHER INFORMATION: chondroitin-binding peptide

<400> SEQUENCE: 32

Tyr Lys Thr Asn Phe Arg Arg Tyr Tyr Arg Phe
1               5                   10


<210> SEQ ID NO 33
<211> LENGTH: 11
<212> TYPE: PRT
<213> ORGANISM: Artificial Sequence
<220> FEATURE:
<223> OTHER INFORMATION: chondroitin-binding peptide

<400> SEQUENCE: 33

Val Leu Ile Arg His Phe Arg Lys Arg Tyr Tyr
1               5                   10


<210> SEQ ID NO 34
<211> LENGTH: 29
<212> TYPE: PRT
<213> ORGANISM: Artificial Sequence
<220> FEATURE:
<223> OTHER INFORMATION: hCII259-273 with N-terminal and C-terminal
      sequence

<400> SEQUENCE: 34

Ser Ala Trp Ser His Pro Gln Phe Glu Lys Gly Ile Ala Gly Phe Lys
1               5                   10                  15

Gly Glu Gln Gly Pro Lys Gly Glu Pro Ser Gly Gly Gly
            20                  25


<210> SEQ ID NO 35
<211> LENGTH: 13
<212> TYPE: PRT
<213> ORGANISM: Homo sapiens

<400> SEQUENCE: 35

Gly Ile Ala Gly Phe Lys Gly Glu Gln Gly Pro Lys Gly
1               5                   10


<210> SEQ ID NO 36
<211> LENGTH: 15
<212> TYPE: PRT
```

-continued

```
<213> ORGANISM: Homo sapiens
<220> FEATURE:
<221> NAME/KEY: MOD_RES
<222> LOCATION: (6)..(6)
<223> OTHER INFORMATION: Xaa = galactosyl-Hyl

<400> SEQUENCE: 36

Gly Ile Ala Gly Phe Xaa Gly Glu Gln Gly Pro Lys Gly Glu Pro
1               5                   10                  15
```